US007928225B2

(12) United States Patent
Björe et al.

(10) Patent No.: US 7,928,225 B2
(45) Date of Patent: *Apr. 19, 2011

(54) OXABISPIDINE COMPOUNDS FOR THE TREATMENT OF CARDIAC ARRHYTHMIAS

(75) Inventors: Annika Björe, Mölndal (SE); David Cladingboel, Loughborough (GB); Gareth Ensor, Loughborough (GB); Adam Herring, Loughborough (GB); Johan Kajanus, Mölndal (SE); Robert Lundqvist, Mölndal (SE); Christina Olsson, Mölndal (SE); Carl-Gustav Sigfridsson, Mölndal (SE); Gert Strandlund, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 534 days.
This patent is subject to a terminal disclaimer.

(21) Appl. No.: 11/917,195

(22) PCT Filed: Jun. 12, 2006

(86) PCT No.: PCT/SE2006/000688
§ 371 (c)(1),
(2), (4) Date: May 29, 2008

(87) PCT Pub. No.: WO2006/135316
PCT Pub. Date: Dec. 21, 2006

(65) Prior Publication Data
US 2009/0054422 A1 Feb. 26, 2009

(30) Foreign Application Priority Data

Jun. 13, 2005 (SE) .................. PCT/SE2005/000891
Dec. 15, 2005 (SE) ....................... 0502775

(51) Int. Cl.
C07D 265/36 (2006.01)
C07D 498/02 (2006.01)
A61K 31/535 (2006.01)

(52) U.S. Cl. .................... 544/105; 514/230.5
(58) Field of Classification Search .............. 544/105; 514/230.5
See application file for complete search history.

(56) References Cited

U.S. PATENT DOCUMENTS

| 3,196,154 | A | 7/1965 | Steck et al. |
| 3,503,939 | A | 3/1970 | Williams et al. |
| 3,962,449 | A | 6/1976 | Binnig et al. |
| 4,459,301 | A | 7/1984 | Binnig et al. |
| 4,533,713 | A | 8/1985 | Howells |
| 4,550,112 | A | 10/1985 | Schoen et al. |
| 4,556,662 | A | 12/1985 | Binnig et al. |
| 5,140,033 | A | 8/1992 | Schriewer et al. |
| 5,468,858 | A | 11/1995 | Berlin et al. |
| 5,831,099 | A | 11/1998 | Dave et al. |
| 6,559,143 | B1 * | 5/2003 | Bjore et al. ............... 214/230.5 |
| 6,936,712 | B1 | 8/2005 | Pavey |
| 7,164,017 | B2 | 1/2007 | Cladingboel et al. |
| 7,169,921 | B2 | 1/2007 | Cheema et al. |
| 7,217,708 | B2 | 5/2007 | Barnwell et al. |
| 7,354,917 | B2 | 4/2008 | Bjore et al. |
| 7,648,985 | B2 * | 1/2010 | Bjore et al. ............... 514/230.5 |
| 2004/0133000 | A1 | 7/2004 | Cheema et al. |
| 2007/0197519 | A1 | 8/2007 | Cheema et al. |

FOREIGN PATENT DOCUMENTS

| EP | 306871 | 9/1988 |
| EP | 308843 | 9/1988 |
| EP | 655228 | 5/1995 |
| EP | 1330461 | 4/2002 |
| EP | 1330462 | 4/2002 |
| EP | 1235831 | 3/2005 |
| EP | 1559717 | 3/2005 |
| GB | 1256850 | 12/1971 |
| HU | 8200945 | 4/1988 |
| JP | 5772977 | 5/1982 |
| JP | 6284070 | 10/1994 |
| JP | 6284071 | 10/1994 |
| JP | 2003512352 | 4/2003 |
| WO | 9107405 | 5/1991 |
| WO | 9931100 | 6/1999 |
| WO | 0061569 | 10/2000 |
| WO | 0128992 | 4/2001 |
| WO | 0228863 | 4/2002 |
| WO | 0228864 | 4/2002 |
| WO | 02083688 | 10/2002 |
| WO | 02083690 | 10/2002 |
| WO | 02083691 | 10/2002 |
| WO | 2002083687 | 10/2002 |
| WO | 03101956 | 11/2003 |
| WO | 2004035592 | 4/2004 |
| WO | WO2005/123747 | 6/2005 |
| WO | 2005123748 | 12/2005 |

OTHER PUBLICATIONS

Yoshidome et al., "Infrared spectroscopic analyses of transformations of chemical species on the silica highly-reacted with gaseous BF3," (2003) 19:429-435.

Bogousslavsky et al., "Pure midbrain infarction: clinical syndromes, MRI, and etiologic patterns," (1994) Neurology 44:2032-2040.

[No Authors Listed] "Preliminary report: effect of encainide and flecainide on mortality in a randomized trial of arrhythmia suppression after myocardial infarction. The Cardiac Arrhythmia Suppression Trial (CAST) Investgators," New England Journal of Medicine (1989) 321(6): 406-412.

Chapman et al., "Nitrolysis of a Highly Deactivated Amide by Protonitronium. Synthesis and Structure of HNFX(1)," J Org Chem (1999) 64(3):960-965.

Chapman et al., "Difluoramination of Heterocyclic Ketones: Control of Microbasicity," J Org Chem (1998) 63 (5):1566-1570.

Chen et al., "High-Performance Liquid Chromatographic Determination of SAZ-VII-22, a Novel Antiarrhythmic Agent, in Dog Plasma and Urine," Anal Sci (1993) 9(3):429-431.

Dave et al., "Facile Preparation of 3,7-Diazabicyclo[3.3.0]octane and 3,7,10-Triheterocyclic [3.3.3]Propellane Ring Systems from 1,5-Diazacyclooctane 3,7-Derivatives," J Org Chem (1996) 61(25):8897-8903.

(Continued)

Primary Examiner — Kahsay T Habte
(74) Attorney, Agent, or Firm — Pepper Hamilton LLP

(57) ABSTRACT

There is provided compounds of formula I, wherein $R^1$, $R^2$, $R^3$, $R^{41}$ to $R^{46}$, X, Y and Z have meanings given in the description, which compounds are useful in the prophylaxis and in the treatment of arrhythmias, in particular atrial and ventricular arrhythmias.

16 Claims, No Drawings

OTHER PUBLICATIONS

Jeyaraman et al., "Chemistry of 3-azabicyclo[3.3.1]nonanes," Chem Rev (1981) 81(2):149-174.

Garrison et al., "Novel 3,7-diheterabicyclo[3.3.1]nonanes that possess predominant class III antiarrhythmic activity in 1-4 day post infarction dog models: X-ray diffraction analysis of 3-[4-(1H-imidazol-1-yl)benzoyl]-7-isopropyl-3,7-diazabicyclo[3.3.1]nona ne dihydroperchlorate," J Med Chem (1996) 39(13):2559-2570.

Lange et al., "Facile Conversion of Primary and Secondary Alcohols to Alkyl Iodides," Synthetic Communication (1990) 20(10):1473-1479.

Nemec et al., "Pharmacotherapy of atrial fibrillation," Expert Opinion of Pharmacotherapy (1999) 1(1):81-96.

Nelson et al., "Synthesis of 2,5- and 2,6-bis(bromomethyl)-1,4-diphenylpiperazines and their conversion into 2,5-diphenyl-2,5-diazabicyclo[2.2.2]octane," J Org Chem (1971) 36(22):3361-3365.

Paroczai et al., "Investigations to characterize a new antiarrhythmic drug bisaramil," Pharmacol Res (1991) 24 (2):149-162.

Paudler et al., "3,7-Disubstituted octahydro-1,5-diazocines. Their conversion into tetrahydro-1,5-diazocines and to ring-contracted products," J Org Chem (1967) 32(8):2425-2430.

Paudler et al., "1,5-Bis(p-toluenesulfonyl)-3,7-Dihydroxyoctahydro-1,5-diazocine," J Org Chem (1966) 31(1):277-281.

Steck et al., "3-Substituted 9-Methyl-3,9-Diazabicyclo[3.3.1]nonanes," J Org Chem (1963) 28(9):2233-2238.

Stetter et al., "Synthese des 1,3-Diaza-6-oxa-adamantans," Chem Ber (1963) 96(11):2827-2830.

Villa et al., "3,8-diazabicyclo—[3.2.1]-octane derivatives as analogues of ambasilide, a Class III antiarrhythmic agent," Eur J. Med Chem (2001) 36(6):495-506.

Wang et al., "Class III antiarrhythmic drug action in experimental atrial fibrillation. Differences in reverse use dependence and effectiveness between d-sotalol and the new antiarrhythmic drug ambasilide," Circulation (1994) 90 (4):2032-2040.

Chemical Abstracts, vol. 56, (1962), No. 154911, Nikitskya et al., Zh. Obshich 31:3202-3205 (1961).

Chemical Abstracts, vol. 59, (1963) No. 7474h, Cignarelli et al., Gazz. Chim. Ital. 93(4):320-328 (1963).

Chemical Abstracts, vol. 59, (1963) No. 2822c, Cignarelli et al., Gazz. Chim. Ital. 93(4):226-237 (1963).

Chemical Abstracts, vol. 46 (1952) No. 992f, Zu-Yoong Kyi et al., J Chem Soc pp. 1706-1708 (1963).

Chemical Abstracts, vol. 48, (1954) No. 2068d, Barnes et al., J Am Chem Soc 75:975-977 (1953).

Chemical Abstracts, vol. 55, (1961) No. 19010d, Rubstov et al., J Med Pharm Chem 3:441-460 (1961).

Tsukerman et al., "Basicity and Structure of Heterocyclic Alpha, Beta- Unsaturated Ketones," Zh Obshch Khim (1963) 33(9):3110-3112.

Notice of Allowance dated Nov. 9, 2007 for copending U.S. Appl. No. 11/570,439.

Office Action dated Oct. 2, 2007 received in Copending U.S. Appl. No. 11/612,826.

Notice of Allowance dated Mar. 2, 2005 for copending U.S. Appl. No. 10/474,585.

Notice of Allowance dated Feb. 14, 2006 for copending U.S. Appl. No. 10/474,593.

Office Action dated Mar. 20, 2006 for copending U.S. Appl. No. 10/474,593.

Office Action dated Jun. 23, 2006 for copending U.S. Appl. No. 10/474,593.

Weinges et al., "[Uber den mechanismus der saurekatalysierten Kondensations-reaktionen der Hydroxy-flavane und Hydroxy-flavanole-(3)]," (1963) 96:2870-2878.

Rubtsov et al., "Synthesis and pharmacological investigation of derivatives of 9-methyl-3,9-diazabicyclo-(3,3,1)-nonane," J Med Pharm Chem (1961) 3(3):441-459.

Kyi et al., "Synethic analgesics and related compounds. Part II. Some derivatives of 3:7-diazabicyclo[3:3:1]nonane (Bispidine)," J. Chem Soc. (1951) 1706-1705.

Nikitskaya et al., "Bicyclic systems based on 2,6-lutidine. V. Bisquaternary salts of—bis(9-methyl-3,9-diazabicyclo [3.3.1]nonan-3-yl)alkanes," Zh. Obshich. Khim. (1961) 31:3202-3205; Chemical Abstracts, vol. 56 (1962), Abstract No. 15491.

Cignarella et al., "Intramolecular acyl migration in the 3.9-diazabicycla [3.3.1]-nonane series," Gazz. Chim. Ital., (1963) 93(4):320-328; chemcial abstracts, vol. 59 (1963), Abstract No. 7474.

Cignarella et al., "Investigation on 3,9-diazabicyclo[3.3.1]nonanes. Sterochemistry and analgesic activity of 3,9-diazabicyclo [3.3.1]octane derivatives," Gazz Chim Ital (1963) 93:226-37; Chemical Abstracts, vol. 59 (1963), Abstract No. 2822.

Notice of Allowance dated Mar. 2, 2009 received in copending U.S. Appl. No. 12/029,483.

Office Action dated Mar. 24, 2010, received in copending U.S. Appl. No. 12/497,792.

U.S. Office Action dated Jan. 7, 2009 cited in copending U.S. Appl. No. 12/028,955.

Nonfinal office action dated Apr. 16, 2009 received in copending U.S. Appl. No. 11/570,451.

Abstract No. 1987:637909, CA, vol. 107 (1987).

Abstract No. 1987:146842, CA, vol. 107 (1987).

Office Action dated Nov. 17, 2008 cited in copending U.S. Appl. No. 12/029,483.

Office Action dated Dec. 15, 2008 cited in copending U.S. Appl. No. 12/029,501.

* cited by examiner

OXABISPIDINE COMPOUNDS FOR THE TREATMENT OF CARDIAC ARRHYTHMIAS

CROSS-REFERENCE TO RELATED APPLICATIONS

This application is the U.S. National Stage filing of International Application Serial No. PCT/SE2006/000688 filed Jun. 12, 2006, which claims priority to International Application Serial No. PCT/SE2005/000891 filed Jun. 13, 2005 and to Swedish Application Serial No. 0502775-0 filed Dec. 15, 2005, each of which is incorporated herein by reference in its entirety.

FIELD OF THE INVENTION

This invention relates to novel pharmaceutically useful compounds, in particular compounds which are useful in the treatment of cardiac arrhythmias.

BACKGROUND AND PRIOR ART

Cardiac arrhythmias may be defined as abnormalities in the rate, regularity, or site of origin of the cardiac impulse or as disturbances in conduction which causes an abnormal sequence of activation. Arrhythmias may be classified clinically by means of the presumed site of origin (i.e. as supraventricular, including atrial and atrioventricular, arrhythmias and ventricular arrhythmias) and/or by means of rate (i.e. bradyarrhythmias (slow) and tachyarrhytimias (fast)).

In the treatment of cardiac arrhythmias, the negative outcome in clinical trials (see, for example, the outcome of the Cardiac Arrhythmia Suppression Trial (CAST) reported in *New England Journal of Medicine*, 321, 406 (1989)) with "traditional" antiarrhytric drugs, which act primarily by slowing the conduction velocity (class I antiarrhythmic drugs), has prompted drug development towards compounds which selectively delay cardiac repolarization, thus prolonging the QT interval. Class III antiarrhythmic drugs may be defined as drugs which prolong the trans-membrane action potential duration (which can be caused by a block of outward K currents or from an increase of inward ion currents) and refractoriness, without affecting cardiac conduction.

One of the key disadvantages of hitherto known drugs which act by delaying repolarization (class III or otherwise) is that they all are known to exhibit a unique form of proarrhythmia known as torsades de pointes (turning of points), which may, on occasion be fatal. From the point of view of safety, the minimisation of this phenomenon (which has also been shown to be exhibited as a result of administration of non-cardiac drugs such as phenothiazines, tricyclic antidepressants, antihistamines and antibiotics) is a key problem to be solved in the provision of effective antiarrhythmic drugs.

Antiarrhythmic drugs based on bispidines (3,7-diazabicyclo[3.3.1]nonanes), are known from inter alia international patent applications WO 91/07405 and WO 99/31100, European patent applications 306 871, 308 843 and 655 228 and U.S. Pat. Nos. 3,962,449, 4,556,662, 4,550,112, 4,459,301 and 5,468,858, as well as journal articles including, inter alia, *J. Med. Chem.* 39, 2559, (1996), *Pharmacol. Res.*, 24, 149 (1991), *Circulation*, 90, 2032 (1994) and *Anal. Sci.* 9, 429 (1993).

Certain oxabispidine compounds are disclosed as chemical curiosities in *Chem. Ber.*, 96, 2872 (1963). The use of certain other oxabispidine compounds in the treatment of cardiac arrhythmias is disclosed in WO 01/28992. Methods for the preparation of such oxabispidine compounds are disclosed in WO 02/28863, WO 02/28864, WO 02/83690 and WO 02/83691. Further, acid addition salts that are useful in such methods of preparation are disclosed in WO 04/035592.

Further groups of oxabispidine compounds that are useful in the treatment of cardiac arrhythmias are disclosed in unpublished international patent application numbers PCT/SE2005/000890 and PCT/SE2005/000891.

We have surprisingly found that a sub-group of oxabispidine-based compounds comprising a carbamate-substituted alkyl group exhibit unexpectedly beneficial properties that render them particularly suitable for use in the treatment of cardiac arrhythmias.

DISCLOSURE OF THE INVENTION

According to the invention there is provided a compound of formula I,

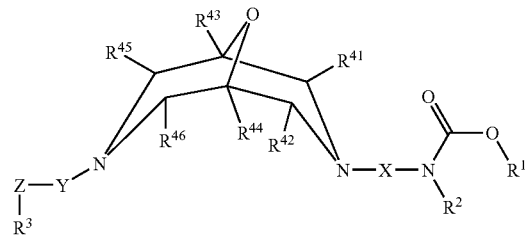

I wherein
R$^1$ represents C$_{1-6}$ alkyl optionally substituted by one or more groups selected from halo and aryl;
R$^2$ represents H or C$_{1-4}$ alkyl (which latter group is optionally substituted by one or more halo atoms);
X represents C$_{2-4}$ n-alkylene optionally substituted by one or more groups selected from C$_{1-4}$ alkyl and halo;
Y represents C$_{1-6}$ n-alkylene, which alkylene group is
(a) optionally interrupted by —O—, —C(O)—, —S(O)$_{0-2}$—, —N(R$^{5a}$)-J$^1$-, -J$^1$-N(R$^{5b}$)— or —N(-J$^2$-R$^{5c}$)—,
(b) optionally substituted by one or more groups selected from halo and methyl and/or by a single C$_{1-6}$ alkyl group that is substituted by one or more groups selected from halo, —O-G-R$^{6a}$, -J$^1$-N(R$^{6b}$)R$^{6c}$, —N(R$^{6d}$)-J$^2$-R$^{6e}$ and —N(R$^{6f}$)C(NH)NH$_2$), and/or
(c) optionally substituted, on a C-atom that is not attached to another heteroatom (N—, O— or S-atom), by a substituent selected from —O-G-R$^{6a}$, J$^1$-N(R$^{6b}$)R$^{6c}$—, —N(R$^{6d}$)-J$^2$-R$^{6e}$, and —N(R$^{6f}$)C(NH)NH$_2$);
J$^1$ and J$^2$ independently represent, independently at each occurrence —C(O)—, —S(O)$_2$— or —OC(O)—, in which latter group the C(O) moiety is attached to the N-atom to which the group J$^1$ or J$^2$ is linked,
or J$^1$ may alternatively represent a direct bond,
or J$^2$ may alternatively represent —[C(O)]$_{1-2}$—N(R$^{6g}$)—, in which latter group —N(R$^{6g}$)— is attached to R$^{5c}$ or R$^{6e}$;
G represents a direct bond, —C(O)— or —C(O)O—, in which latter group the C(O) moiety is attached to the O-atom to which the group G is linked;
R$^{5a}$ and R$^{5b}$ independently represent H or C$_{1-6}$ alkyl;
R$^{5c}$ and R$^{6a}$ to R$^{6g}$ represent, independently at each occurrence, C$_{1-6}$ alkyl (optionally substituted by one or more groups selected from halo, aryl and Het$^1$), aryl or Het$^2$,
or R$^{6a}$ to R$^{6d}$, R$^{6f}$ and R$^{6g}$ represent, independently at each occurrence, H, or $R^{5c}$ or $R^{6e}$, when $J^2$ represents —C(O)—, may alternatively represent H;

Het$^1$ and Het$^2$ independently represent five- to twelve-membered heterocyclic groups containing one or more heteroatoms selected from oxygen, nitrogen and/or sulfur, which groups are optionally substituted by one or more groups selected from —OH, oxo, halo, cyano, nitro, $C_{1-6}$ alkyl, $C_{1-6}$ alkoxy, aryl, aryloxy, —N($R^{7a}$)$R^{7b}$, —C(O)$R^{7c}$, —C(O)O$R^{7d}$, —C(O)N($R^{7e}$)$R^{7f}$, —N($R^{7g}$)C(O)$R^{7h}$, —S(O)$_2$N($R^{7i}$)$R^{7j}$ and —N($R^{7k}$)S(O)$_2$$R^{7m}$;

Z represents a direct bond, —O—, —C(O)—, —S(O)$_{0-2}$—, —S(O)$_2$—N($R^{7n}$)— or —N($R^{7p}$)—S(O)$_2$—;

$R^{7a}$ to $R^{7p}$ independently represent $C_{1-6}$ alkyl or aryl, or $R^{7a}$ to $R^{7k}$, $R^{7n}$ and $R^{7p}$ independently represent H;

$R^3$ represents phenyl or Het$^a$, which latter two groups are optionally substituted by one or more $R^8$ groups;

Het$^a$ represents a five- to twelve-membered heterocyclic group containing one or more heteroatoms selected from oxygen, nitrogen and/or sulfur;

$R^8$ represents —OH, cyano, halo, nitro, $C_{1-6}$ alkyl (optionally terminated by —N(H)C(O)O$R^{9a}$), $C_{1-6}$ alkoxy, —N($R^{10a}$)$R^{10b}$, C(O)$R^{10c}$, C(O)O$R^{10d}$, —C(O)N($R^{10e}$)$R^{10f}$, —N($R^{10g}$)C(O)$R^{10h}$, —N($R^{10i}$)C(O)N($R^{10j}$)$R^{10k}$, —N($R^{10m}$)S(O)$_2$$R^{9b}$, —S(O)$_2$N($R^{10n}$)$R^{10p}$, —S(O)$_2$$R^{9c}$, —OS(O)$_2$$R^{9d}$, —Si($R^{9e}$)$_3$ and aryl;

$R^{9a}$ to $R^{9e}$ represent, independently at each occurrence, $C_{1-6}$ alkyl or phenyl, which latter group is optionally substituted by one or more groups selected from —OH, halo, cyano, $C_{1-4}$ alkyl and $C_{1-4}$ alkoxy;

$R^{10a}$ and $R^{10b}$ independently represent H, $C_{1-6}$ alkyl or together represent $C_{3-6}$ alkylene, resulting in a four- to seven-membered nitrogen-containing ring;

$R^{10c}$ to $R^{10p}$ independently represent H or $C_{1-6}$ alkyl; and $R^{41}$ to $R^{46}$ independently represent H or $C_{1-3}$ alkyl;

wherein each aryl group, unless otherwise specified, is optionally substituted;

or a pharmaceutically acceptable derivative thereof, provided that the compound is not:
(a) tert-butyl {2-[7-(2-{4-[(methylsulfonyl)amino] phenoxy}ethyl)-9-oxa-3,7-diazabicyclo[3.3.1]non-3-yl]ethyl}carbamate;
(b) tert-butyl (2-{7-[2-(4-nitrophenoxy)ethyl]-9-oxa-3,7-diazabicyclo[3.3.1]non-3-yl}ethyl)carbamate;
(c) tert-butyl {2-[7-(4-pyridin-4-ylbutyl)-9-oxa-3,7-diazabicyclo[3.3.1]non-3-yl]ethyl}carbamate;
(d) tert-butyl (2-{7-[3-(4-cyanophenoxy)propyl]-9-oxa-3,7-diazabicyclo[3.3.1]-non-3-yl}ethyl)carbamate;
(e) tert-butyl (2-{7-[2-(4-cyanophenoxy)ethyl]-9-oxa-3,7-diazabicyclo[3.3.1]non-3-yl}ethyl)carbamate;
(f) tert-butyl (2-{7-[4-(4-cyanophenyl)butyl]-9-oxa-3,7-diazabicyclo[3.3.1]non-3-yl}ethyl)carbamate;
(g) tert-butyl (2-{7-[2-(2,4-dicyanophenoxy)ethyl]-9-oxa-3,7-diazabicyclo[3.3.1]-non-3-yl}ethyl)carbamate;
(h) tert-butyl (2-{7-[(2S)-3-(4-cyanophenoxy)-2-hydroxypropyl]-9-oxa-3,7-diazabicyclo[3.3.1]non-3-yl}ethyl)carbamate;
(i) tert-butyl[2-(7-{3-[(4-cyanophenyl)amino]propyl}-9-oxa-3,7-diazabicyclo-[3.3.1]non-3-yl)ethyl]carbamate;
(j) tert-butyl 2-{7-[2-(4-aminophenoxy)ethyl]-9-oxa-3,7-diazabicyclo[3.3.1]-non-3-yl}ethylcarbamate;
(k) tert-butyl{2-[7-(2-{[(4-fluorophenyl)sulfonyl]amino}ethyl)-9-oxa-3,7-diazabicyclo[3.3.1]non-3-yl]ethyl}carbamate;
(l) {2-[7-Benzyl-9-oxa-3,7-diazabicyclo[3.3.1]non-3-yl]ethyl}tert-butyl-carbamate;
(m) tert-butyl[2-(7-{2-[[2-(4-cyanophenoxy)ethyl](methylsulfonyl)amino]ethyl}-9-oxa-3,7-diazabicyclo[3.3.1]non-3-yl)ethyl]carbamate;
(n) tert-butyl {2-[7-(2-{(aminocarbonyl)[2-(4-cyanophenoxy)ethyl]amino}ethyl)-9-oxa-3,7-diazabicyclo[3.3.1] non-3-yl]ethyl}carbamate; or
(o) tert-butyl[2-(7-{2-[[3-(4-cyanophenyl)propyl](methylsulfonyl)amino]ethyl}-9-oxa-3,7-diazabicyclo[3.3.1]non-3-yl)ethyl]carbamate.

Compounds of formula I, as defined above, may hereinafter be referred to as "compounds of the invention".

Unless otherwise specified, alkyl groups and alkoxy groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes $C_{6-10}$ aryl groups such as phenyl, naphthyl and the like. The term "aryloxy", when used herein includes $C_{6-10}$ aryloxy groups such as phenoxy, naphthoxy and the like. For the avoidance of doubt, aryloxy groups referred to herein are attached to the rest of the molecule via the O-atom of the oxy-group. Unless otherwise specified, aryl and aryloxy groups may be substituted by one or more groups including —OH, halo, cyano, nitro, $C_{1-6}$ alkyl, $C_{1-6}$ alkoxy, —N($R^{10a}$)$R^{10b}$, C(O)$R^{10c}$, —C(O)O$R^{10d}$, —C(O)N($R^{10e}$)$R^{10f}$, —N($R^{10g}$)C(O)$R^{10h}$, —N($R^{10m}$)S(O)$_2$$R^{9b}$, —S(O)$_2$N($R^{10n}$)$R^{10p}$, —S(O)$_2$$R^{9c}$, —OS(O)$_2$$R^{9d}$ and/or —Si($R^{9e}$)$_3$ (wherein $R^{9b}$ to $R^{9e}$ and $R^{10a}$ to $R^{10p}$ are as hereinbefore defined). When substituted, aryl groups are preferably substituted by between one and three substituents.

The term "halo", when used herein, includes fluoro, chloro, bromo and iodo.

Heterocyclic (Het$^1$, Het$^2$ and Het$^a$) groups that may be mentioned include those containing 1 to 4 heteroatoms (selected from the group oxygen, nitrogen and/or sulfur) and in which the total number of atoms in the ring system are between five and twelve. Heterocyclic (Het$^1$, Het$^2$ and Het$^a$) groups may be fully saturated, partly unsaturated, wholly aromatic or partly aromatic in character. Values of heterocyclic (Het$^1$, Het$^2$ and Het$^a$) groups that may be mentioned include 1-azabicyclo[2.2.2]octanyl, benzimidazolyl, benzo [c]isoxazolidinyl, benzisoxazolyl, benzodioxanyl, benzodioxepanyl, benzodioxolyl, benzofuranyl, benzofurazanyl, benzomorpholinyl, 2,1,3-benzoxadiazolyl, benzoxazolidinyl, benzoxazolyl, benzopyrazolyl, benzo[e]pyrimidine, 2,1,3-benzothiadiazolyl, benzothiazolyl, benzothienyl, benzotriazolyl, chromanyl, chromenyl, cinnolinyl, 2,3-dihydrobenzimidazolyl, 2,3-dihydrobenzo[b]furanyl, 1,3-dihydrobenzo[c]-furanyl, 1,3-dihydro-2,1-benzisoxazolyl 2,3-dihydropyrrolo[2,3-b]pyridinyl, dioxanyl, furanyl, hexahydropyrimidinyl, hydantoinyl, imidazolyl, imidazo[1,2-a]pyridinyl, imidazo[2,3-b]thiazolyl, indolyl, isoquinolinyl, isoxazolidinyl, isoxazolyl, maleimido, morpholinyl, naphtho[1,2-b]furanyl, oxadiazolyl, 1,2- or 1,3-oxazinanyl, oxazolyl, phthalazinyl, piperazinyl, piperidinyl, purinyl, pyranyl, pyrazinyl, pyrazolyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, sulfolanyl, 3-sulfolenyl, 4,5,6,7-tetrahydrobenzimidazolyl, 4,5,6,7-tetrahydrobenzopyrazolyl, 5,6,7,8-tetra-hydrobenzo[e]pyrimidine, tetrahydrofuranyl, tetrahydropyranyl, 3,4,5,6-tetra-hydropyridinyl, 1,2,3,4-tetrahydropyrimidinyl, 3,4,5,6-tetrahydropyrimidinyl, thiadiazolyl, thiazolidinyl, thiazolyl, thienyl, thieno[5,1-c]pyridinyl, thiochromanyl, triazolyl, 1,3,4-triazolo[2,3-b]pyrimidinyl, xanthenyl and the like.

Values of Het$^a$ that may be mentioned include pyridinyl.

Substituents on heterocyclic (Het$^1$, Het$^2$ and Het$^a$) groups may, where appropriate, be located on any atom in the ring system including a heteroatom. The point of attachment of heterocyclic (Het$^1$, Het$^2$ and Het$^a$) groups may be via any atom in the ring system including (where appropriate) a heteroatom, or an atom on any fused carbocyclic ring that may be present as part of the ring system. Heterocyclic (Het$^1$, Het$^2$ and Het$^a$) groups may also be in the N— or S-oxidised form.

Pharmaceutically acceptable derivatives include salts and solvates. Salts which may be mentioned include acid addition salts. Pharmaceutically acceptable derivatives also include, at the oxabispidine or other heterocyclic nitrogen atoms, $C_{1-4}$ alkyl quaternary ammonium salts and N-oxides.

The compounds of the invention may exhibit tautomerism. All tautomeric forms and mixtures thereof are included within the scope of the invention.

The compounds of the invention may also contain one or more asymmetric carbon atoms and may therefore exist as enantiomers or diastereoisomers, and may exhibit optical activity. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimensation, or by derivatisation, for example with a homochiral acid followed by separation of the diastereomeric esters by conventional means (e.g. HPLC, chromatography over silica). All stereoisomers are included within the scope of the invention.

Abbreviations are listed at the end of this specification.

Compounds of the invention that may be mentioned include those in which J$^1$ and J$^2$ do not represent —C(O)—.

Compounds of formula I that may be mentioned include those that either (a) are or (b) are not benzyl-{2-[7-(4-cyanobenzyl)-9-oxa-3,7-diazabicyclo[3.3.1]non-3-yl]ethyl}-carbamic acid tert-butyl ester.

Further compounds of formula I that may be mentioned include those in which:
R$^1$ represents $C_{1-5}$ alkyl optionally substituted by phenyl;
R$^2$ represents H or $C_{1-3}$ alkyl;
X represents $C_{2-4}$ n-alkylene optionally substituted by halo (e.g. F);
Y represents $C_{1-5}$ n-alkylene, which alkylene group is
(a) optionally interrupted, between C-atoms that are not attached to other heteroatoms (N—, O— or S-atoms), by O or —N(S(O)$_2$R$^{5c}$)—,
(b) optionally substituted by halo (e.g. F), and/or
(c) optionally substituted, on a C-atom that is not attached to another heteroatom (N—, O— or S-atom), by a substituent selected from —O—R$^{6a}$, —N(H)R$^{6c}$ and —N(H)-J$^2$-R$^{6e}$;
J$^2$ represents —OC(O)—, in which latter group the C(O) moiety is attached to the N-atom to which the group J$^2$ is linked;
R$^{5c}$ and R$^{6a}$ to leg independently represent $C_{1-4}$ alkyl (optionally substituted by one or more groups selected from halo (e.g. F) and phenyl),
or R$^{1a}$ to R$^{6d}$, R$^{6f}$ and R$^{6g}$ represent, independently at each occurrence, H,
or R$^{5c}$ or R$^{6e}$, when J$^2$ represents —C(O)—, may alternatively represent H;
Z represents a direct bond, —O—, —S— or —S(O)$_2$—;
R$^3$ represents phenyl substituted by one or more R$^8$ groups;
R$^8$ represents cyano or halo (e.g. F or Cl);
R$^{41}$ to R$^{46}$ all represent H.

Still further compounds of formula I that may be mentioned include those in which:
R$^1$ represents $C_{1-5}$ branched alkyl (e.g. tert-butyl);
R$^2$ represents H or methyl;
X represents $C_{2-4}$ n-alkylene (e.g. $C_2$ or $C_3$ n-alkylene) optionally substituted by F;
Y represents $C_{1-4}$ n-alkylene, which alkylene group is
(a) optionally interrupted, between C-atoms that are not attached to other heteroatoms (N—, O— or S-atoms), by O,
(b) optionally substituted by F, and/or
(c) optionally substituted, on a C-atom that is not attached to another heteroatom (N—, O— - or S-atom), by a substituent selected from —OH and methoxy;
Z represents a direct bond, —S(O)$_2$— or, particularly, —O—;
R$^3$ represents phenyl substituted, at the 2-, the 6-, and/or, particularly, the 4-position by one to three groups selected from halo (e.g. F or Cl) and cyano.

Two particular embodiments of the invention relate to compounds of formula I that either (a) are or (b) are not compounds of formula Ia, wherein compounds of formula Ia are compounds of formula I in which X represents $C_3$ n-alkylene optionally substituted by one or more groups selected from $C_{1-4}$ alkyl and halo.

Compounds of formula Ia that may be mentioned include those in which:
R$^1$ represents tert-butyl;
R$^2$ represents methyl or, particularly, H;
X represents —(CH$_2$)$_3$—;
Y represents $C_2$ or, particularly, $C_3$ n-alkylene;
Z represents —O—;
R$^3$ represents phenyl substituted at the 4-position by cyano and optionally substituted at the 2- and/or 6-positions by F.

Further compounds of formula Ia that may be mentioned include those in which R$^3$ represents phenyl substituted at the 4-position by cyano and optionally substituted at the 2-position by F (e.g. phenyl substituted at the 4-position by cyano).

Further particular embodiments of the invention relate to compounds of formula I and Ia that either (a) are or (b) are not compounds of formula Ib, wherein compounds of formula Ib are compounds of formula I or Ia in which R³ is represented by the structural fragment

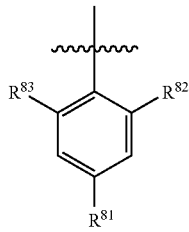

wherein the wavy line indicates the position of attachment to the group Z and
R⁸¹ represents F, Cl or, particularly, cyano,
R⁸² represents halo (e.g. F or Cl) and
R⁸³ represents halo (e.g. F or Cl) or, particularly, H.

Compounds of formula Ib that may be mentioned include those in which:
R¹ represents tert-butyl;
R² represents methyl or, particularly, H;
X represents C₃ or, particularly, C₂ n-alkylene;
Y represents C₃ or, particularly, C₂ n-alkylene;
Z represents —O—.

Compounds of formula Ib that may be mentioned include those that either (a) are or (b) are not compounds of formula Ia, as hereinbefore defined.

Compounds of formula Ia and Ib may also hereinafter be referred to as "compounds of the invention".

Compounds of the invention that may be mentioned include the compounds of the examples below, such as:
(a) tert-butyl (3-{7-[2-(4-cyano-2,6-difluorophenoxy)ethyl]-9-oxa-3,7-diazabicyclo[3.3.1]non-3-yl}propyl)carbamate;
(b) tert-butyl (2-{7-[2-(4-cyano-2-fluorophenoxy)ethyl]-9-oxa-3,7-diazabicyclo-[3.3.1]non-3-yl}ethyl)carbamate;
(c) tert-butyl (3-{7-[2-(4-cyano-2-fluorophenoxy)ethyl]-9-oxa-3,7-diazabicyclo-[3.3.1]non-3-yl}propyl)carbamate;
(d) tert-butyl (3-{7-[3-(4-cyano-2-fluorophenoxy)propyl]-9-oxa-3,7-diazabicyclo-[3.3.1]non-3-yl}propyl)carbamate;
(e) tert-butyl (3-{7-[3-(4-cyanophenoxy)propyl]-9-oxa-3,7-diazabicyclo[3.3.1]-non-3-yl}propyl)carbamate;
(f) tert-butyl (2-{7-[2-(4-cyanophenoxy)ethyl]-9-oxa-3,7-diazabicyclo[3.3.1]non-3-yl}ethyl)methylcarbamate;
(g) tert-butyl (2-{7-[3-(4-cyanophenoxy)-2-fluoropropyl]-9-oxa-3,7-diazabicyclo-[3.3.1]non-3-yl}ethyl)carbamate;
(h) (3-{7-[2-(4-cyanophenoxy)ethyl]-9-oxa-3,7-diazabicyclo[3.3.1]non-3-yl}-propyl)carbamic acid tert-butyl ester;
(i) {3-[7-(4-cyanobenzyl)-9-oxa-3,7-diazabicyclo[3.3.1]non-3-yl]propyl}-carbamic acid tert-butyl ester;
(j) tert-butyl{2-[7-(4-cyanobenzyl)-9-oxa-3,7-diazabicyclo[3.3.1]non-3-yl]ethyl}-carbamate;
(k) tert-butyl [3-(7-benzyl-9-oxa-3,7-diazabicyclo[3.3.1]non-3-yl)propyl]-carbamate;
(l) tert-butyl (3-{7-[3-(2,4-dicyanophenoxy)propyl]-9-oxa-3,7-diazabicyclo-[3.3.1]non-3-yl}propyl)carbamate;
(m) tert-butyl ((2R)-3-{7-[(2S)-3-(4-cyanophenoxy)-2-hydroxypropyl]-9-oxa-3,7-diazabicyclo[3.3.1]non-3-yl}-2-fluoropropyl)carbamate;
(n) tert-butyl (3-{7-[(2S)-3-(4-cyanophenoxy)-2-hydroxypropyl]-9-oxa-3,7-diazabicyclo[3.3.1]non-3-yl}propyl) methylcarbamate;
(o) tert-butyl (3-{7-[3-(4-cyanophenoxy)propyl]-9-oxa-3,7-diazabicyclo[3.3.1]-non-3-yl}propyl)methylcarbamate;
(p) tert-butyl (3-{7-[2-(4-cyanophenoxy)ethyl]-9-oxa-3,7-diazabicyclo[3.3.1]non-3-yl}propyl)methylcarbamate;
(q) tert-butyl (2-{7-[2-(4-cyanophenoxy)ethyl]-9-oxa-3,7-diazabicyclo[3.3.1]non-3-yl}ethyl)methylcarbamate;
(r) tert-butyl (2-{7-[3-(4-cyanophenoxy)propyl]-9-oxa-3,7-diazabicyclo[3.3.1]-non-3-yl}ethyl)methylcarbamate;
(s) tert-butyl (3-{7-[3-(4-cyano-2,6-difluorophenoxy)propyl]-9-oxa-3,7-diazabicyclo[3.3.1]non-3-yl}propyl)carbamate;
(t) tert-butyl (2-{7-[2-(4-cyano-2,6-difluorophenoxy)ethyl]-9-oxa-3,7-diazabicyclo[3.3.1]non-3-yl}ethyl)carbamate;
(u) tert-butyl (2-{7-[3-(4-cyano-2,6-difluorophenoxy)propyl]-9-oxa-3,7-diazabicyclo[3.3.1]non-3-yl}ethyl)carbamate;
(v) tert-butyl (2-{7-[3-(4-cyano-2-fluorophenoxy)propyl]-9-oxa-3,7-diazabicyclo-[3.3.1]non-3-yl}ethyl)carbamate;
(w) tert-butyl (2-{7-[(2S)-3-(4-cyano-2,6-difluorophenoxy)-2-hydroxypropyl]-9-oxa-3,7-diazabicyclo[3.3.1]non-3-yl}ethyl)carbamate;
(x) tert-butyl (2-{7-[(2S)-3-(4-cyano-2-fluorophenoxy)-2-hydroxypropyl]-9-oxa-3,7-diazabicyclo[3.3.1]non-3-yl}ethyl)carbamate;
(y) tert-butyl (3-{7-[2-(4-cyanophenoxy)ethyl]-9-oxa-3,7-diazabicyclo[3.3.1]non-3-yl}propyl)carbamate;
(z) tert-butyl [2-(7-{2-[(4-cyanobenzyl)oxy]ethyl}-9-oxa-3,7-diazabicyclo-[3.3.1]non-3-yl)ethyl]carbamate;
(aa) tert-butyl (2-{7-[3-(4-cyanophenoxy)-2-fluoropropyl]-9-oxa-3,7-diazabicyclo[3.3.1]non-3-yl}ethyl)carbamate;
(ab) tert-butyl (2-{7-[2-(4-cyanophenyl)ethyl]-9-oxa-3,7-diazabicyclo[3.3.1]non-3-yl}ethyl)carbamate;
(ac) tert-butyl (2-{7-[(2S)-3-(4-cyanophenoxy)-2-methoxypropyl]-9-oxa-3,7-diazabicyclo[3.3.1]non-3-yl}ethyl)carbamate;
(ad) tert-butyl (2-{7-[(2S)-3-(4-cyanophenoxy)-2-hydroxypropyl]-9-oxa-3,7-diazabicyclo[3.3.1]non-3-yl}ethyl) methylcarbamate;
(ae) tert-butyl [2-(7-{3-[(4-cyanophenyl)sulfonyl]propyl}-9-oxa-3,7-diazabicyclo-[3.3.1]non-3-yl)ethyl]carbamate;
(af) tert-butyl [2-(7-{2-[2-(4-cyanophenyl)ethoxy]ethyl}-9-oxa-3,7-diazabicyclo-[3.3.1]non-3-yl)ethyl]carbamate;
(ag) tert-butyl (3-{7-[(2S)-3-(4-cyanophenoxy)-2-hydroxypropyl]-9-oxa-3,7-diazabicyclo[3.3.1]non-3-yl}propyl) carbamate;
(ah) tert-butyl (2-{7-[3-(4-fluorophenoxy)-2-hydroxypropyl]-9-oxa-3,7-diazabicyclo[3.3.1]non-3-yl}ethyl)carbamate;
(ai) tert-butyl (2-{7-[3-(4-chlorophenoxy)-2-hydroxypropyl]-9-oxa-3,7-diazabicyclo[3.3.1]non-3-yl}ethyl)carbamate;
(aj) tert-butyl [2-(7-{2-[2-(4-cyanophenoxy)ethoxy]ethyl}-9-oxa-3,7-diazabicyclo[3.3.1]non-3-yl)ethyl]carbamate;
(ak) tert-butyl (2-{7-[2-(4-bromo-2-fluorophenoxy)ethyl]-9-oxa-3,7-diazabicyclo[3.3.1]non-3-yl}ethyl)carbamate;
(al) tert-butyl (2-{7-[3-(2,4-dicyanophenoxy)propyl]-9-oxa-3,7-diazabicyclo[3.3.1]non-3-yl}ethyl)carbamate;
(am) tert-butyl (3-{7-[3-(4-cyano-2-hydroxyphenoxy)propyl]-9-oxa-3,7-diazabicyclo[3.3.1]non-3-yl}propyl)carbamate,
and salts and/or solvates thereof.

Particular compounds of the invention that may be mentioned include:
(i) compounds (a) to (aj) above;
(ii) compounds (a) to (aj) above, other than compound (k) above;
(iii) compounds (a) to (g) above; or
(iv) compounds (a) to (e) above,
and salts and/or solvates thereof.

In this respect, particular compounds that may be mentioned include:

tert-butyl (3-{7-[3-(4-cyanophenoxy)propyl]-9-oxa-3,7-diazabicyclo[3.3.1]non-3-yl}propyl)carbamate; or, particularly, tert-butyl (2-{7-[2-(4-cyano-2-fluorophenoxy)ethyl]-9-oxa-3,7-diazabicyclo-[3.3.1]non-3-yl}ethyl)carbamate, and salts and/or solvates thereof.

Particular forms of tert-butyl (2-{7-[2-(4-cyano-2-fluorophenoxy)ethyl]-9-oxa-3,7-diazabicyclo[3.3.1]non-3-yl}ethyl)carbamate that may be mentioned include crystalline forms characterised by the presence, in X-ray powder diffraction (XRPD) measurements, of peaks at about the 2-Theta and relative intensity values detailed in either Table 1 or Table 2 below.

TABLE 1

XRPD Peaks for Form A of tert-butyl (2-{7-[2-(4-cyano-2-fluorophenoxy)ethyl]-9-oxa-3,7-diazabicyclo[3.3.1]non-3-yl}ethyl)carbamate

| Peak label | Angle (2-Theta, °) | Relative Intensity (%) |
|---|---|---|
| a | 4.280 | 79.2 |
| b | 8.513 | 100.0 |
| c | 11.259 | 27.1 |
| d | 12.770 | 7.8 |
| e | 14.120 | 25.7 |
| f | 15.652 | 2.4 |
| g | 17.020 | 4.4 |
| h | 17.217 | 7.7 |
| i | 17.570 | 28.2 |
| j | 18.576 | 8.8 |
| k | 18.780 | 12.3 |
| l | 19.041 | 12.7 |
| m | 19.608 | 3.9 |
| n | 20.514 | 18.5 |
| o | 20.940 | 3.7 |
| p | 21.295 | 2.8 |
| q | 22.583 | 25.8 |
| r | 23.006 | 3.9 |
| s | 23.501 | 4.5 |
| t | 23.759 | 3.6 |
| u | 24.018 | 4.4 |
| v | 24.480 | 3.9 |
| w | 25.354 | 5.1 |
| x | 25.637 | 3.0 |
| y | 26.599 | 3.0 |
| z | 34.379 | 3.4 |

TABLE 2

XRPD Peaks for Form B of tert-butyl (2-{7-[2-(4-cyano-2-fluorophenoxy)ethyl]-9-oxa-3,7-diazabicyclo[3.3.1]non-3-yl}ethyl)carbamate

| Peak label | Angle (2-Theta, °) | Relative Intensity (%) |
|---|---|---|
| A | 8.012 | 100.0 |
| B | 9.459 | 27.3 |
| C | 9.995 | 1.9 |
| D | 10.782 | 2.4 |
| E | 13.049 | 3.0 |
| F | 15.542 | 9.9 |
| G | 15.616 | 10.4 |
| H | 16.073 | 7.2 |
| I | 16.820 | 32.2 |
| J | 17.716 | 4.4 |
| K | 17.903 | 3.7 |
| L | 18.693 | 2.3 |
| M | 19.306 | 3.1 |
| N | 20.030 | 7.5 |
| O | 20.728 | 6.2 |
| P | 21.637 | 5.7 |
| Q | 22.008 | 2.4 |
| R | 22.518 | 4.4 |
| S | 23.026 | 4.2 |

TABLE 2-continued

XRPD Peaks for Form B of tert-butyl (2-{7-[2-(4-cyano-2-fluorophenoxy)ethyl]-9-oxa-3,7-diazabicyclo[3.3.1]non-3-yl}ethyl)carbamate

| Peak label | Angle (2-Theta, °) | Relative Intensity (%) |
|---|---|---|
| T | 24.322 | 2.5 |
| U | 24.717 | 3.6 |
| V | 25.768 | 4.1 |
| W | 28.556 | 3.8 |
| X | 32.430 | 9.1 |

Other forms of tert-butyl (2-{7-[2-(4-cyano-2-fluorophenoxy)ethyl]-9-oxa-3,7-diazabicyclo[3.3.1]non-3-yl}ethyl)carbamate that may be mentioned include crystalline forms characterised by the presence, in X-ray powder diffraction (XRPD) measurements, of:

(a) peaks at the 2-Theta values of either Table 1 or Table 2 above having a relative intensity of above 25% (i.e. peaks a, b, c, e, i and q of Table 1 or peaks A, B and I of Table 2);

(b) peaks at the 2-Theta values of either Table 1 or Table 2 above having a relative intensity of above 10% (i.e. peaks a, b, c, e, i, k, l, n and q of Table 1 or peaks A, B, G and I of Table 2); or (c) peaks at the 2-Theta values of either Table 1 or Table 2 above having a relative intensity of above 5% (i.e. peaks a, b, c, e, h, i, j, k, l, n, q and w of Table 1 or peaks A, B, F, G, H, I, N, O, P and X of Table 2).

The crystalline forms of tert-butyl (2-{7-[2-(4-cyano-2-fluorophenoxy)ethyl]-9-oxa-3,7-diazabicyclo[3.3.1]non-3-yl}ethyl)carbamate mentioned above, i.e. either Form A (that characterised by the presence, in XRPD measurements, of all peaks, or only certain selected peaks, from Table 1 above) or Form B (that characterised by the presence, in XRPD measurements, of all peaks, or only certain selected peaks, from Table 1 above) may be further characterised by the presence of one or more of the additional properties listed below:

(i) for Form A (I) when characterised by thermogravimetric analysis, a weight loss of less than 0.1% up to 110° C., and/or (II) when characterised by differential scanning calorimetry, at a heating rate of 10° C. per minute in a closed cup with a pinhole under flowing nitrogen, a melting temperature (Tm) having an onset at about 90° C. and/or an associated endotherm of melting of about 79 J/g;

(i) for Form B (I) when characterised by thermogravimetric analysis, a weight loss of less than 0.2% up to 10° C., and/or (II) when characterised by differential scanning calorimetry, at a heating rate of 10° C. per minute in a closed cup with a pinhole under flowing nitrogen, a melting temperature (Tm) having an onset at about 90° C. and/or an associated endotherm of melting of about 89 J/g.

Particular forms of tert-butyl (3-{7-[3-(4-cyanophenoxy)propyl]-9-oxa-3,7-diazabicyclo[3.3.1]non-3-yl}propyl)carbamate that may be mentioned include crystalline forms characterised by the presence, in X-ray powder diffraction (XRPD) measurements, of peaks at about the 2-Theta and relative intensity values detailed in either Table 3 or Table 4 below.

TABLE 3

XRPD Peaks for Form A of tert-butyl (3-{7-[3-(4-cyanophenoxy)propyl]-9-oxa-3,7-diazabicyclo[3.3.1]non-3-yl}propyl)carbamate

| Peak label | Angle (2-Theta, °) | Relative Intensity (%) |
|---|---|---|
| i | 5.281 | 23.4 |
| ii | 10.640 | 100.0 |
| iii | 12.469 | 2.4 |
| iv | 13.220 | 1.3 |
| v | 13.831 | 5.1 |
| vi | 14.583 | 2.3 |
| vii | 17.505 | 5.4 |
| viii | 18.495 | 7.8 |
| ix | 19.124 | 5.2 |
| x | 19.660 | 5.8 |
| xi | 20.665 | 7.2 |
| xii | 21.165 | 4.1 |
| xiii | 22.022 | 2.0 |
| xiv | 22.801 | 2.2 |
| xv | 23.462 | 3.2 |
| xvi | 23.778 | 4.2 |
| xvii | 25.033 | 3.8 |
| xviii | 32.368 | 1.9 |

TABLE 4

XRPD Peaks for Form B of tert-butyl (3-{7-[3-(4-cyanophenoxy)-propyl]-9-oxa-3,7-diazabicyclo[3.3.1]non-3-yl}propyl)carbamate

| Peak label | Angle (2-Theta, °) | Relative Intensity (%) |
|---|---|---|
| 1 | 5.466 | 11.3 |
| 2 | 6.772 | 10.4 |
| 3 | 8.499 | 22.0 |
| 4 | 9.580 | 7.4 |
| 5 | 10.387 | 8.7 |
| 6 | 10.940 | 35.7 |
| 7 | 11.064 | 39.4 |
| 8 | 11.643 | 33.8 |
| 9 | 12.166 | 27.2 |
| 10 | 13.226 | 28.7 |
| 11 | 13.560 | 16.4 |
| 12 | 13.762 | 12.0 |
| 13 | 14.339 | 14.4 |
| 14 | 14.804 | 13.9 |
| 15 | 15.479 | 19.7 |
| 16 | 15.644 | 26.3 |
| 17 | 15.944 | 54.3 |
| 18 | 16.221 | 12.2 |
| 19 | 16.928 | 48.0 |
| 20 | 17.681 | 11.6 |
| 21 | 17.884 | 11.8 |
| 22 | 18.376 | 12.3 |
| 23 | 18.586 | 62.2 |
| 24 | 19.124 | 100.0 |
| 25 | 19.457 | 19.2 |
| 26 | 20.081 | 14.8 |
| 27 | 20.358 | 58.9 |
| 28 | 20.880 | 16.3 |
| 29 | 21.116 | 15.0 |
| 30 | 21.537 | 19.9 |
| 31 | 21.824 | 35.7 |
| 32 | 21.979 | 20.2 |
| 33 | 22.172 | 16.5 |
| 34 | 22.399 | 14.7 |
| 35 | 23.279 | 14.1 |
| 36 | 23.764 | 11.8 |
| 37 | 23.996 | 14.8 |
| 38 | 24.860 | 11.9 |
| 39 | 25.632 | 8.9 |
| 40 | 25.979 | 8.6 |
| 41 | 27.453 | 9.6 |
| 42 | 28.952 | 12.9 |
| 43 | 29.644 | 12.1 |

Other forms of tert-butyl (3-{7-[3-(4-cyanophenoxy)propyl]-9-oxa-3,7-diazabicyclo[3.3.1]non-3-yl}propyl)carbamate that may be mentioned include crystalline forms characterised by the presence, in X-ray powder diffraction (XRPD) measurements, of:
(a) peaks at the 2-Theta values of either Table 3 or Table 4 above having a relative intensity of above 25% (i.e. peak ii of Table 3 or peaks 6 to 10, 17, 19, 23, 24, 27 and 31 of Table 4); or
(b) peaks at the 2-Theta values of either Table 3 or Table 4 above having a relative intensity of above 10% (i.e. peaks i and ii of Table 3 or peaks 1 to 3, 6 to 38, 42 and 43 of Table 4).

The crystalline forms of tert-butyl (3-{7-[3-(4-cyanophenoxy)propyl]-9-oxa-3,7-diazabicyclo[3.3.1]non-3-yl}propyl)carbamate mentioned above, i.e. either Form A (that characterised by the presence, in XRPD measurements, of all peaks, or only certain selected peaks, from Table 3 above) or Form B (that characterised by the presence, in XRPD measurements, of all peaks, or only certain selected peaks, from Table 4 above) may be further characterised by the presence of one or more of the additional properties listed below:
(I) when characterised by thermogravimetric analysis, display a weight loss of less than 0.2% up to 110° C., and/or
(II) when characterised by differential scanning calorimetry, at a heating rate of 10° C. per minute in a closed cup with a pinhole under flowing nitrogen, display a melting temperature (Tm) having an onset at:
(i) for Form A, about 48° C.; and
(ii) for Form B, at about 66° C.

Particular salts of tert-butyl (2-{7-[2-(4-cyano-2-fluorophenoxy)ethyl]-9-oxa-3,7-diazabicyclo[3.3.1]non-3-yl}ethyl)carbamate that may be mentioned include salts with fumaric acid or maleic acid.

Particular forms of tert-butyl (2-{7-[2-(4-cyano-2-fluorophenoxy)ethyl]-9-oxa-3,7-diazabicyclo[3.3.1]non-3-yl}ethyl)carbamate, fumaric acid salt that may be mentioned include crystalline forms characterised by the presence, in X-ray powder diffraction (XRPD) measurements, of peaks at about the 2-Theta and relative intensity values detailed in Table 5 below.

TABLE 5

XRPD Peaks for tert-butyl (2-{7-[2-(4-cyano-2-fluorophenoxy)ethyl]-9-oxa-3,7-diazabicyclo[3.3.1]non-3-yl}ethyl)carbamate, fumaric acid salt

| Peak label | Angle (2-Theta, °) | Relative Intensity (%) |
|---|---|---|
| I | 5.180 | 58.2 |
| II | 7.785 | 49.9 |
| III | 8.429 | 13.1 |
| IV | 9.363 | 5.1 |
| V | 10.397 | 53.4 |
| VI | 10.694 | 4.6 |
| VII | 11.899 | 14.8 |
| VIII | 12.337 | 24.2 |
| IX | 13.048 | 9.5 |
| X | 13.314 | 11.4 |
| XI | 13.912 | 5.6 |
| XII | 14.282 | 8.1 |
| XIII | 14.973 | 37.9 |
| XIV | 15.687 | 8.5 |
| XV | 16.584 | 12.2 |
| XVI | 17.022 | 71.5 |
| XVII | 17.427 | 22.4 |
| XVIII | 17.529 | 19.2 |
| XIX | 18.886 | 20.5 |
| XX | 20.759 | 46.4 |
| XXI | 20.936 | 100.0 |
| XXII | 21.849 | 16.3 |
| XXIII | 21.971 | 18.9 |
| XXIV | 22.405 | 11.8 |

TABLE 5-continued

XRPD Peaks for tert-butyl (2-{7-[2-(4-cyano-2-fluorophenoxy)ethyl]-9-oxa-3,7-diazabicyclo[3.3.1]non-3-yl}ethyl)carbamate, fumaric acid salt

| Peak label | Angle (2-Theta, °) | Relative Intensity (%) |
|---|---|---|
| XXV | 22.680 | 13.6 |
| XXVI | 23.014 | 30.5 |
| XXVII | 24.705 | 9.3 |
| XXVIII | 26.299 | 13.6 |
| XXIX | 26.877 | 12.0 |
| XXX | 27.143 | 13.2 |
| XXXI | 27.462 | 19.0 |
| XXXII | 29.424 | 9.7 |

Other forms of tert-butyl (2-{7-[2-(4-cyano-2-fluorophenoxy)ethyl]-9-oxa-3,7-diazabicyclo[3.3.1]non-3-yl}ethyl)carbamate, fumaric acid salt that may be mentioned include crystalline forms characterised by the presence, in X-ray powder diffraction (XRPD) measurements, of:
(a) peaks at the 2-Theta values of Table 5 above having a relative intensity of above 25% (i.e. peaks I, II, V, XIII, XVI, XX, XXI and XXVI of Table 5); or
(b) peaks at the 2-Theta values of Table 5 above having a relative intensity of above 10% (i.e. peaks I to III, V, VII, VIII, XIII, XV to XXVI and XXVIII to XXXI of Table 5).

The crystalline forms of tert-butyl (2-{7-[2-(4-cyano-2-fluorophenoxy)ethyl]-9-oxa-3,7-diazabicyclo[3.3.1]non-3-yl}ethyl)carbamate, fumaric acid salt mentioned above, i.e. those characterised by the presence, in XRPD measurements, of all peaks, or only certain selected peaks, from Table 5 above may be further characterised by the presence of one or more of the additional properties listed below:
(I) when characterised by thermogravimetric analysis, display a weight loss of about 1.4% up to 110° C., and/or
(II) when characterised by differential scanning calorimetry, at a heating rate of 10° C. per minute in a closed cup with a pinhole under flowing nitrogen, display a melting temperature (Tm) having an onset at about 120° C.

Particular forms of tert-butyl (2-{7-[2-(4-cyano-2-fluorophenoxy)ethyl]-9-oxa-3,7-diazabicyclo[3.3.1]non-3-yl}ethyl)carbamate, maleic acid salt that may be mentioned include crystalline forms characterised by the presence, in X-ray powder diffraction (XRPD) measurements, of peaks at about the 2-Theta and relative intensity values detailed in Table 6 below.

TABLE 6

XRPD Peaks for tert-butyl (2-{7-[2-(4-cyano-2-fluorophenoxy)ethyl]-9-oxa-3,7-diazabicyclo[3.3.1]non-3-yl}ethyl)carbamate, maleic acid salt

| Peak label | Angle (2-Theta, °) | Relative Intensity (%) |
|---|---|---|
| (a) | 5.978 | 51.9 |
| (b) | 8.600 | 100.0 |
| (c) | 11.918 | 44.2 |
| (d) | 12.071 | 99.2 |
| (e) | 13.795 | 18.8 |
| (f) | 15.632 | 25.3 |
| (g) | 15.810 | 35.7 |
| (h) | 16.169 | 51.9 |
| (i) | 17.065 | 36.1 |
| (j) | 17.241 | 89.4 |
| (k) | 18.016 | 73.6 |
| (l) | 19.699 | 96.0 |
| (m) | 20.211 | 16.1 |
| (n) | 20.660 | 53.2 |
| (o) | 21.569 | 18.4 |
| (p) | 22.021 | 13.8 |
| (q) | 22.586 | 44.0 |
| (r) | 22.878 | 68.0 |

TABLE 6-continued

XRPD Peaks for tert-butyl (2-{7-[2-(4-cyano-2-fluorophenoxy)ethyl]-9-oxa-3,7-diazabicyclo[3.3.1]non-3-yl}ethyl)carbamate, maleic acid salt

| Peak label | Angle (2-Theta, °) | Relative Intensity (%) |
|---|---|---|
| (s) | 23.654 | 31.9 |
| (t) | 24.028 | 51.4 |
| (u) | 24.097 | 54.2 |
| (v) | 24.438 | 36.8 |
| (w) | 24.702 | 28.3 |
| (x) | 27.079 | 28.3 |
| (y) | 27.759 | 34.8 |
| (z) | 28.395 | 42.1 |
| (aa) | 29.192 | 15.1 |
| (ab) | 30.247 | 34.5 |
| (ac) | 32.061 | 14.1 |
| (ad) | 34.348 | 18.7 |
| (ae) | 39.290 | 15.4 |

Other forms of tert-butyl (2-{7-[2-(4-cyano-2-fluorophenoxy)ethyl]-9-oxa-3,7-diazabicyclo[3.3.1]non-3-yl}ethyl)carbamate, maleic acid salt that may be mentioned include crystalline forms characterised by the presence, in X-ray powder diffraction (XRPD) measurements, of peaks at the 2-Theta values of Table 6 above having a relative intensity of above 25% (i.e. peaks (a) to (d), (f) to (l), (n), (q) to (z) and (ab) of Table 6).

The crystalline forms of tert-butyl (2-{7-[2-(4-cyano-2-fluorophenoxy)ethyl]-9-oxa-3,7-diazabicyclo[3.3.1]non-3-yl}ethyl)carbamate, maleic acid salt mentioned above, i.e. those characterised by the presence, in XRPD measurements, of all peaks, or only certain selected peaks, from Table 6 above may be further characterised by the presence of one or more of the additional properties listed below:
(I) when characterised by thermogravimetric analysis, display a weight loss of about 1.2% up to 110° C., and/or
(II) when characterised by differential scanning calorimetry, at a heating rate of 10° C. per minute in a closed cup with a pinhole under flowing nitrogen, display a melting temperature (Tm) having an onset at about 90° C.

Particular salts of tert-butyl (3-{7-[3-(4-cyanophenoxy)propyl]-9-oxa-3,7-diazabicyclo[3.3.1]non-3-yl}propyl)carbamate that may be mentioned include salts with tartaric acid (e.g. L-tartaric acid) or hydrobromic acid.

Particular forms of tert-butyl (3-{7-[3-(4-cyanophenoxy)propyl]-9-oxa-3,7-diazabicyclo[3.3.1]non-3-yl}propyl)carbamate, L-tartaric acid salt that may be mentioned include crystalline forms characterised by the presence, in X-ray powder diffraction (XRPD) measurements, of peaks at about the 2-Theta and relative intensity values detailed in either Table 7, Table 8, Table 9 or Table 10 below.

TABLE 7

XRPD Peaks for Form A of tert-butyl (3-{7-[3-(4-cyanophenoxy)-propyl]-9-oxa-3,7-diazabicyclo[3.3.1]non-3-yl}propyl)carbamate, L-tartaric acid salt

| Peak label | Angle (2-Theta, °) | Relative Intensity (%) |
|---|---|---|
| (A) | 5.346 | 100.0 |
| (B) | 7.175 | 44.4 |
| (C) | 8.222 | 50.2 |
| (D) | 10.682 | 11.8 |
| (E) | 13.800 | 8.9 |
| (F) | 14.373 | 16.6 |
| (G) | 15.200 | 12.3 |
| (H) | 15.920 | 12.6 |
| (I) | 16.126 | 27.6 |
| (J) | 16.458 | 86.5 |

TABLE 7-continued

XRPD Peaks for Form A of tert-butyl (3-{7-[3-(4-cyanophenoxy)-propyl]-9-oxa-3,7-diazabicyclo[3.3.1]non-3-yl}propyl)carbamate, L-tartaric acid salt

| Peak label | Angle (2-Theta, °) | Relative Intensity (%) |
|---|---|---|
| (K) | 16.721 | 29.1 |
| (L) | 18.670 | 44.8 |
| (M) | 19.723 | 62.7 |
| (N) | 19.996 | 38.1 |
| (O) | 20.264 | 8.2 |
| (P) | 21.442 | 26.8 |
| (Q) | 21.599 | 40.5 |
| (R) | 22.081 | 11.2 |
| (S) | 22.505 | 60.7 |
| (T) | 24.519 | 12.6 |
| (U) | 24.654 | 16.6 |
| (V) | 25.687 | 9.9 |
| (W) | 26.851 | 7.4 |
| (X) | 27.481 | 14.5 |
| (Y) | 28.544 | 14.1 |
| (Z) | 29.202 | 8.4 |

TABLE 8

XRPD Peaks for Form B of tert-butyl (3-{7-[3-(4-cyanophenoxy)-propyl]-9-oxa-3,7-diazabicyclo[3.3.1]non-3-yl}propyl)carbamate, L-tartaric acid salt

| Peak label | Angle (2-Theta, °) | Relative Intensity (%) |
|---|---|---|
| (i) | 5.059 | 100.0 |
| (ii) | 7.346 | 13.3 |
| (iii) | 8.091 | 7.8 |
| (iv) | 9.712 | 3.5 |
| (v) | 10.124 | 14.5 |
| (vi) | 13.608 | 3.0 |
| (vii) | 13.931 | 3.9 |
| (viii) | 14.380 | 11.7 |
| (ix) | 15.220 | 7.4 |
| (x) | 15.587 | 24.3 |
| (xi) | 16.211 | 5.0 |
| (xii) | 16.475 | 24.1 |
| (xiii) | 17.396 | 4.2 |
| (xiv) | 18.164 | 15.5 |
| (xv) | 18.901 | 9.8 |
| (xvi) | 19.078 | 18.9 |
| (xvii) | 19.360 | 5.8 |
| (xviii) | 19.480 | 5.3 |
| (xix) | 20.329 | 18.3 |
| (xx) | 21.488 | 9.4 |
| (xxi) | 21.760 | 12.4 |
| (xxii) | 22.164 | 10.2 |
| (xxiii) | 22.570 | 5.8 |
| (xxiv) | 23.183 | 3.9 |
| (xxv) | 25.221 | 4.5 |
| (xxvi) | 25.748 | 5.4 |
| (xxvii) | 27.593 | 5.1 |
| (xxviii) | 29.150 | 3.6 |

TABLE 9

XRPD Peaks for Form C of tert-butyl (3-{7-[3-(4-cyanophenoxy)-propyl]-9-oxa-3,7-diazabicyclo[3.3.1]non-3-yl}propyl)carbamate, L-tartaric acid salt

| Peak label | Angle (2-Theta, °) | Relative Intensity (%) |
|---|---|---|
| (I) | 5.111 | 100.0 |
| (II) | 7.139 | 6.6 |
| (III) | 7.662 | 8.9 |
| (IV) | 7.800 | 6.4 |
| (V) | 8.355 | 21.3 |
| (VI) | 10.195 | 28.9 |
| (VII) | 10.929 | 3.8 |

TABLE 9-continued

XRPD Peaks for Form C of tert-butyl (3-{7-[3-(4-cyanophenoxy)-propyl]-9-oxa-3,7-diazabicyclo[3.3.1]non-3-yl}propyl)carbamate, L-tartaric acid salt

| Peak label | Angle (2-Theta, °) | Relative Intensity (%) |
|---|---|---|
| (VIII) | 13.788 | 8.6 |
| (IX) | 14.379 | 13.6 |
| (X) | 14.847 | 10.0 |
| (XI) | 15.294 | 9.0 |
| (XII) | 15.543 | 7.3 |
| (XIII) | 16.280 | 33.6 |
| (XIV) | 16.787 | 17.1 |
| (XV) | 17.320 | 9.0 |
| (XVI) | 17.510 | 14.4 |
| (XVII) | 18.461 | 16.1 |
| (XVIII) | 18.805 | 11.8 |
| (XIX) | 19.501 | 13.5 |
| (XX) | 19.958 | 26.2 |
| (XXI) | 20.502 | 22.3 |
| (XXII) | 21.058 | 13.6 |
| (XXIII) | 21.361 | 9.2 |
| (XXIV) | 21.783 | 12.3 |
| (XXV) | 23.104 | 6.4 |
| (XXVI) | 23.602 | 9.4 |
| (XXVII) | 24.832 | 9.0 |
| (XXVIII) | 25.439 | 8.5 |
| (XXIX) | 28.599 | 6.7 |

TABLE 10

XRPD Peaks for Form D of tert-butyl (3-{7-[3-(4-cyanophenoxy)-propyl]-9-oxa-3,7-diazabicyclo[3.3.1]non-3-yl}propyl)carbamate, L-tartaric acid salt

| Peak label | Angle (2-Theta, °) | Relative Intensity (%) |
|---|---|---|
| (1) | 5.315 | 100.0 |
| (2) | 7.231 | 19.9 |
| (3) | 8.304 | 39.0 |
| (4) | 10.652 | 7.9 |
| (5) | 13.770 | 9.9 |
| (6) | 14.331 | 14.2 |
| (7) | 15.138 | 10.6 |
| (8) | 15.837 | 10.4 |
| (9) | 16.236 | 16.5 |
| (10) | 16.553 | 74.0 |
| (11) | 16.718 | 33.2 |
| (12) | 18.627 | 32.5 |
| (13) | 18.785 | 29.1 |
| (14) | 19.696 | 7.2 |
| (15) | 19.976 | 32.2 |
| (16) | 21.546 | 24.4 |
| (17) | 21.849 | 33.7 |
| (18) | 22.647 | 15.3 |
| (19) | 22.816 | 22.7 |
| (20) | 24.597 | 6.8 |
| (21) | 24.834 | 10.5 |
| (22) | 27.764 | 8.7 |

Other forms of tert-butyl (3-{7-[3-(4-cyanophenoxy)propyl]-9-oxa-3,7-diazabicyclo[3.3.1]non-3-yl}propyl)carbamate, L-tartaric acid salt that may be mentioned include crystalline forms characterised by the presence, in X-ray powder diffraction (XRPD) measurements, of:

(a) peaks at the 2-Theta values of Table 7, Table 8, Table 9 or Table 10 above having a relative intensity of above 25% (i.e. peaks (A) to (C), (I) to (N), (P), (Q) and (S) of Table 7, peak (i) of Table 8, peaks (I), (VI), (XIII) and (XX) of Table 9 or peaks (1), (3), (10) to (13), (15) and (17) of Table 10; or (b) peaks at the 2-Theta values of Table 7, Table 8, Table 9 or Table 10 above having a relative intensity of above 10% (i.e. peaks (A) to (D), (F) to (N), (P) to (V), (X) and (Y) of Table 7, peaks (i), (ii), (v), (viii), (x), (xii), (xiv), (xvi), (xix), (xxi) and (xxii) of Table 8, peaks (I), (VI), (VI), (IX), (X), (XIII), (XIV), (XVI) to (XXII) and (XXIV) of Table 9 or peaks (1) to (3), (6) to (13), (15) to (19) and (21) of Table 10).

Crystalline forms of tert-butyl (3-{7-[3-(4-cyanophenoxy)propyl]-9-oxa-3,7-diazabicyclo[3.3.1]non-3-yl}propyl)carbamate, L-tartaric acid salt mentioned above, i.e. either Form A (that characterised by the presence, in XRPD measurements, of all peaks, or only certain selected peaks, from Table 7 above), Form B (that characterised by the presence, in XRPD measurements, of all peaks, or only certain selected peaks, from Table 8 above) or Form C (that characterised by the presence, in XRPD measurements, of all peaks, or only certain selected peaks, from Table 9 above) may be further characterised by the presence of one or more of the additional properties listed below:
(i) for Form A
  (I) when characterised by thermogravimetric analysis, a weight loss of about 1.0% up to 110° C., and/or
  (II) when characterised by differential scanning calorimetry, at a heating rate of 10° C. per minute in a closed cup with a pinhole under flowing nitrogen, a melting temperature (Tm) having an onset at about 134° C.;
(i) for Form B
  (I) when characterised by thermogravimetric analysis, a weight loss of about 1.8% up to 60° C., and/or
  (II) when characterised by differential scanning calorimetry, at a heating rate of 110° C. per minute in a closed cup with a pinhole under flowing nitrogen, a melting temperature (Tm) having an onset at about 90° C.;
(iii) for Form C, when characterised by differential scanning calorimetry, at a heating rate of 10° C. per minute in a closed cup with a pinhole under flowing nitrogen, a melting temperature (Tm) having an onset at about 86° C.

Particular forms of tert-butyl (3-{7-[3-(4-cyanophenoxy)propyl]-9-oxa-3,7-diazabicyclo[3.3.1]non-3-yl}propyl)carbamate, hydrobromic acid salt that may be mentioned include crystalline forms characterised by the presence, in X-ray powder diffraction (XRPD) measurements, of peaks at about the 2-Theta and relative intensity values detailed in Table 11 below.

TABLE 11

XRPD Peaks for tert-butyl (3-{7-[3-(4-cyanophenoxy)propyl]-9-oxa-3,7-diazabicyclo[3.3.1]non-3-yl}propyl)carbamate, hydrobromic acid salt

| Peak label | Angle (2-Theta, °) | Relative Intensity (%) |
|---|---|---|
| a | 3.077 | 28.8 |
| b | 6.102 | 100.0 |
| c | 9.140 | 29.6 |
| d | 12.190 | 51.6 |
| e | 13.555 | 4.3 |
| f | 13.978 | 4.5 |
| g | 14.902 | 6.7 |
| h | 15.238 | 12.2 |
| i | 15.751 | 9.7 |
| j | 17.702 | 9.9 |
| k | 18.320 | 26.0 |
| l | 18.873 | 7.7 |
| m | 19.573 | 13.0 |
| n | 19.944 | 8.1 |
| o | 20.201 | 22.8 |
| p | 20.336 | 13.5 |
| q | 20.971 | 14.8 |
| r | 21.771 | 25.5 |
| s | 22.482 | 12.1 |
| t | 22.633 | 13.4 |
| u | 25.204 | 6.4 |

TABLE 11-continued

XRPD Peaks for tert-butyl (3-{7-[3-(4-cyanophenoxy)propyl]-9-oxa-3,7-diazabicyclo[3.3.1]non-3-yl}propyl)carbamate, hydrobromic acid salt

| Peak label | Angle (2-Theta, °) | Relative Intensity (%) |
|---|---|---|
| v | 25.755 | 5.8 |
| w | 26.123 | 7.7 |
| x | 26.344 | 11.8 |
| y | 26.537 | 14.5 |
| z | 27.889 | 7.0 |
| aa | 29.254 | 10.9 |
| ab | 31.930 | 6.0 |
| ac | 32.320 | 6.0 |
| ad | 33.594 | 7.4 |
| ae | 40.281 | 8.2 |

Other forms of tert-butyl (3-{7-[3-(4-cyanophenoxy)propyl]-9-oxa-3,7-diazabicyclo[3.3.1]non-3-yl}propyl)carbamate, hydrobromic acid salt that may be mentioned include crystalline forms characterised by the presence, in X-ray powder diffraction (XRPD) measurements, of:
(a) peaks at the 2-Theta values of Table 11 above having a relative intensity of above 25% (i.e. peaks a to d, k, o and r of Table 11); or
(b) peaks at the 2-Theta values of Table 11 above having a relative intensity of above 10% (i.e. peaks a to d, h, k, m, o to t, x, y and aa of Table 11).

The crystalline forms of tert-butyl (3-{7-[3-(4-cyanophenoxy)propyl]-9-oxa-3,7-diazabicyclo[3.3.1]non-3-yl}propyl)carbamate, hydrobromic acid salt mentioned above, i.e. those characterised by the presence, in XRPD measurements, of all peaks, or only certain selected peaks, from Table 11 above may be further characterised by the presence of one or more of the additional properties listed below:
(I) when characterised by thermogravimetric analysis, display a weight loss of about 1.9% up to 110° C., and/or
(II) when characterised by differential scanning calorimetry, at a heating rate of 10° C. per minute in a closed cup with a pinhole under flowing nitrogen, display a melting temperature (Tm) having an onset at about 114° C.

Preparation

Compounds of formulae I, Ia and Ib may be prepared by analogy with procedures known to those skilled in the art (e.g. the procedures outlined in WO 01/28992, WO 02/83690, WO 02/83691, WO 02/28863, WO 02/28864 and WO 2004/035592, the disclosures of which documents are hereby incorporated by reference). Thus, according to the invention there is also provided a process for the preparation of compounds of formulae I, Ia and Ib which comprises:
(a) reaction of a compound of formula II,

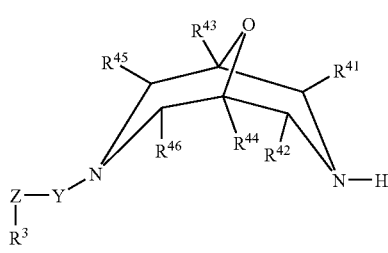

II wherein $R^3$, $R^{41}$ to $R^{46}$, Y and Z are as hereinbefore defined, with a compound of formula III,

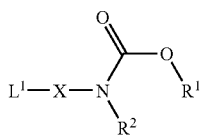

wherein $L^1$ represents a suitable leaving group (such as halo (e.g. chloro or bromo) or $R^aS(O)_2O$—, wherein $R^W$ represents $C_{1-8}$ alkane, $C_{1-8}$ perfluoroalkane or phenyl, which latter group is optionally substituted by one or more substituents selected from $C_{1-4}$ alkyl (e.g. methyl), halo and nitro), and X, $R^1$ and $R^2$ are as hereinbefore defined, for example at between room and reflux temperature (e.g. about 60° C.) in the presence of a suitable base (e.g. triethylamine, potassium carbonate or a bicarbonate, such as sodium bicarbonate) and an appropriate solvent (e.g. dichloromethane, chloroform, acetonitrile, N,N-dimethylformamide, THP, toluene, MIBK, water, a lower alkyl alcohol (e.g. ethanol) or mixtures thereof (e.g. a mixture of toluene or MIBK and water));

(b) reaction of a compound of formula IV,

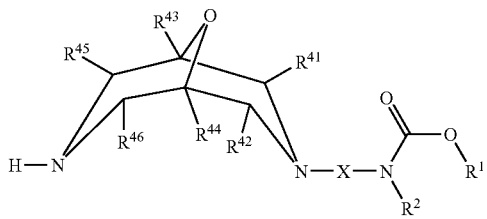

wherein $R^1$, $R^2$, $R^{41}$ to $R^{46}$ and X are as hereinbefore defined, with a compound of formula V,

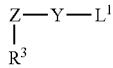

wherein $L^1$, $R^3$, Y and Z are as hereinbefore defined, for example at between room and reflux temperature (e.g. about 60° C.) in the presence of a suitable base (e.g. an alkali metal carbonate (e.g. sodium or potassium carbonate), an alkali metal hydrogencarbonate (e.g. $NaHCO_3$) or an alkali metal hydroxide (e.g. NaOH)) and an appropriate solvent (e.g. a $C_{1-4}$ alkyl alcohol (e.g. IPA), water, an aromatic hydrocarbon (e.g. toluene), a ketone (e.g. MIBK), acetonitrile, or mixtures thereof (e.g. a mixture of a $C_{1-4}$ alkyl alcohol, toluene or MIBK and water));

(c) for compounds of formula I in which the group X comprises a $CH_2$ moiety at the point of attachment to the oxabispidine N-atom, reaction of a compound of formula II, as hereinbefore defined, with a compound of formula VI,

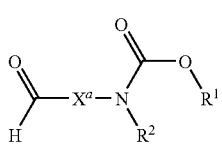

wherein $X^a$ represents $C_{1-3}$ n-alkylene optionally substituted by one or more groups selected from $C_{1-4}$ alkyl and halo and $R^1$ and $R^2$ are as hereinbefore defined, for example under conditions known to those skilled in the art (such as at ambient temperature (e.g. 15 to 25° C.) in the presence of a suitable solvent (e.g. dichloromethane or a $C_{1-3}$ alkyl alcohol) and optionally in the presence of a Lewis acid or proton source (e.g. a carboxylic acid such as acetic acid)), followed by reduction in the presence of a reducing agent (e.g. $NaBH_3CN$), for example under conditions known to those skilled in the art (e.g. at ambient temperature (such as 15 to 25° C.) in the presence of a suitable solvent (e.g. dichloromethane or a $C_{1-3}$ alkyl alcohol));

(d) for compounds of formula I in which the group Y comprises a —$CH_2CH(OH)CH_2$-moiety (wherein a $CH_2$ group forms the point of attachment to the oxabispidine N-atom), reaction of a compound of formula IV, as hereinbefore defined, with a compound of formula VII,

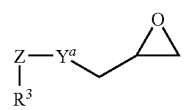

optionally in enantiomeric or enantiomerically enriched form, wherein $Y^a$ represents a direct bond or $C_{1-3}$ n-alkylene, which alkylene group is
(1) optionally interrupted by —O—, —C(O)—, —S $(O)_{0-2}$—, —$N(R^{5a})$-$J^1$-, -$J^1$-$N(R^{5b})$— or —$N(-J^2$-$R^{5c})$—,
(2) optionally substituted by one or more groups selected from halo and methyl and/or by a single $C_{1-6}$ alkyl group that is substituted by one or more groups selected from halo, —O-G-$R^{6a}$, -$J^1$-$N(R^{6b})R^{6c}$, —$N(R^{6d})$-$J^2$-$R^{6e}$ and —$N(R^{6f})C(NH)NH_2$), and/or
(3) optionally substituted, on a C-atom that is not attached to another heteroatom (N—, O— or S-atom), by a substituent selected from —O-G-$R^{6a}$, -$J^1$-$N(R^{6b})R^{6c}$—, —$N(R^{6d})$-$J^2$-$R^{6e}$, and —$N(R^{6f})C(NH)NH_2$),
and $R^3$, $R^{5a}$ to $R^{5c}$, $R^{6a}$ to $R^{6f}$, $J^1$, $J^2$, G and Z are as hereinbefore defined, for example at elevated temperature (e.g. 60° C. to reflux) in the presence of a suitable solvent (e.g. a lower alkyl alcohol (e.g. IPA), acetonitrile, or a mixture of a lower alkyl alcohol and water);

(e) for compounds of formula I in which Z represents O, reaction of a compound of formula VIIa,

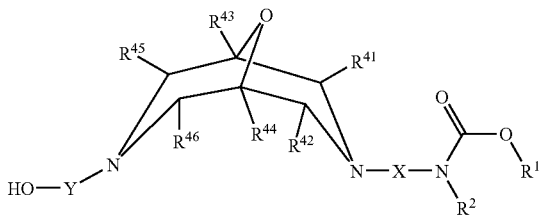

wherein $R^1$, $R^2$, $R^{41}$ to $R^{46}$, X and Y are as hereinbefore defined, with a compound of formula IX, as defined below, under Mitsunobu conditions, for example, reaction at between 15 and 60° C. in the presence of a suitable phosphine (e.g. a triarylphosphine such as triphenylphosphine), an appropriate dehydrating agent (e.g. a dialkylazodicarboxylate, such as diisopropylazodicarboxylate) and a reaction-inert solvent (e.g. dichloromethane);

(f) for compounds of formula I in which X or Y represents an alkylene group that is substituted by halo, substitution of a corresponding compound of formula I in which X or Y represents an alkylene group that is substituted by OH, using an appropriate halogenating agent (e.g. for compounds in which the halo group is F, reaction with (diethylamino)sulfur trifluoride);

(g) conversion of one $R^8$ substituent to another using techniques well known to those skilled in the art;

(h) introduction of one or more (further) $R^8$ substituents using techniques well known to those skilled in the art (e.g. chlorination); or (i) for acid addition salts of compounds of formula I, reaction of a corresponding compound of formula I with an acid.

If they exist, different crystalline forms of compounds of formula I (or salts of such compounds) may be obtained by crystallisation of compounds of formula I (or salts thereof) under different conditions.

For example, tert-butyl (2-{7-[2-(4-cyano-2-fluorophenoxy)ethyl]-9-oxa-3,7-diazabicyclo[3.3.1]non-3-yl}ethyl)carbamate can be obtained by crystallisation from solvent (e.g. by crystallisation, at between 40 and 5° C., from a mixture of diisopropyl ether (IPE) and isopropanol (IPA)). In particular, one form (Form A above) may be obtained by crystallisation (e.g. of a starting material that is less than 100% pure (e.g. between 99 and 100% pure), as determined by HPLC area analysis) from an approximately 5:1 mixture of IPE/IPA (optionally containing trace quantities of toluene and/or MIBC), whereas another (Form B above) may be obtained by crystallisation (e.g. of a starting material that is 100% pure, as determined by HPLC area analysis) from an approximately 10:1 mixture of IPE/IPA.

Further, tert-butyl (3-{7-[3-(4-cyanophenoxy)propyl]-9-oxa-3,7-diazabicyclo-[3.3.1]non-3-yl}propyl)carbamate can be obtained:

(i) in one form (Form A above) by evaporation of solvent from a solution of tert-butyl (3-{7-[3-(4-cyanophenoxy)propyl]-9-oxa-3,7-diazabicyclo-[3.3.1]non-3-yl}propyl)carbamate in a mixture of ethyl acetate and (residual) toluene, followed by standing at ambient temperature, removal of solvent residues under reduced pressure, mechanical manipulation (e.g. stirring with a spatula) of the resulting oil/crystal mixture, followed by further drying under reduced pressure and at ambient temperature, and (ii) in another form (Form B above) by
slurrying crystals of Form A in water or propan-2-ol at ambient temperature (e.g. 25° C.), or in water or heptane at 40° C., or
at 54° C., crystallising the material from a solution (e.g. a solution in water).

Also, tert-butyl (3-{7-[3-(4-cyanophenoxy)propyl]-9-oxa-3,7-diazabicyclo-[3.3.1]non-3-yl}propyl)carbamate, L-tartaric acid salt can be obtained:

(i) in one form (Form A above) by
crystallisation from ethanol (e.g. at any temperature from ambient (e.g. 25° C.) to 5° C.), followed by drying in vacuo at 40° C. for 24 hours,
crystallisation from a mixture of isopropyl acetate and ethanol or
crystallisation from a saturated solution in acetone (which solution is prepared by dissolving L-tartaric acid in acetone (1 g L-tartaric acid per 25 mL acetone) at 50° C. and then adding tert-butyl (3-{7-[3-(4-cyanophenoxy)propyl]-9-oxa-3,7-diazabicyclo-[3.3.1]non-3-yl}propyl)-carbamate to the warm solution, followed by evaporation under reduced pressure of 50% of the volume of solvent and then allowing the resulting solution to cool);

(ii) in another form (Form B above) by slurrying crystals of Form A in water at from ambient temperature (e.g. 20 to 25° C.) to 40° C.; and (iii) in a further form (Form C above) by slurrying crystals of Form A in water at from 54 to 71° C.

Compounds of formulae II, III, IV, V, VI, VII and VIIa may be prepared according to or by analogy with the procedures described or referred to in WO 01/28992, WO 02/28863, WO 02/28864, WO 02/83690, WO 02/83691 and WO 2004/035592, the disclosures of which documents are hereby incorporated by reference. However, particular routes to specific intermediates are described below.

Compounds of formula V in which $L^1$ represents halo and Z represents O may be prepared by either of the following routes:

(a) substitution, using an appropriate halogenating agent, of a corresponding compound of formula VIII

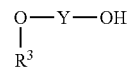

VIII wherein $R^3$ and Y are as hereinbefore defined, for example under conditions known to those skilled in the art; or (b) reaction of a corresponding compound of formula IX,

IX wherein $R^3$ is as hereinbefore defined, with a compound of formula X,

X wherein each $L^2$ group represents halo, for example under conditions known to those skilled in the art (e.g. reaction at elevated temperature (e.g. 50 to 70° C.) in the presence of a suitable base (e.g. $K_2CO_3$) and an appropriate solvent (e.g. DMF or acetonitrile)).

Compounds of formula V in which $L^1$ represents $R^aS(O)_2O—$ and Z represents O may be prepared by reaction of a corresponding compound of formula VIII, as hereinbefore defined, with a compound of formula XI,

XI wherein $L^3$ represents halo (e.g. Cl) or $R^aS(O)_2O—$ and $R^a$ is as hereinbefore defined, for example under conditions known to those skilled in the art (e.g. reaction at between −25° C. and ambient temperature in the presence of an appropriate base (e.g. triethylamine or $K_2CO_3$), a suitable solvent (e.g. toluene, xylene, 4-methyl-2-pentanone, acetonitrile, DCM, or mixtures thereof and, optionally, an appropriate catalyst (e.g. trimethylamine hydrochloride)).

Compounds of formula VIIa may be prepared by reaction of a corresponding compound of formula IV, as hereinbefore defined, with a compound of formula XII, as defined below, for example under conditions known to those skilled in the art (e.g. reaction at between 50 and 80° C. in the presence of an appropriate base (e.g. $K_2CO_3$) and a suitable solvent (e.g. acetonitrile)).

Compounds of formula VIII may be prepared according to or by analogy with methods known to those skilled in the art. However, the following methods are particularly useful.

(a) Compounds of formula VIII may be prepared by reaction of a corresponding compound of formula IX with a compound of formula XII,

XII wherein $L^2$ and Y are as hereinbefore defined, for example under conditions known to those skilled in the art (e.g. reaction at between 50 and 100° C. in the presence of an appropriate base (e.g. $K_2CO_3$) and a suitable solvent (e.g. toluene, 4-methyl-2-pentanone or acetonitrile)).

(b) Compounds of formula VIII in which $R^3$ represents the structural fragment

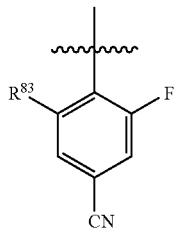

wherein $R^{83}$ is as hereinbefore defined, may be prepared by reaction of a corresponding compound of formula XIII,

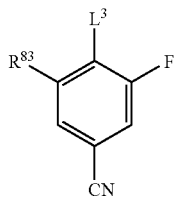

XIII wherein $L^3$ and $R^{83}$ are as hereinbefore defined, with a compound of formula XIV,

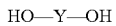                  XIV wherein Y is as hereinbefore defined, for example under conditions known to those skilled in the art (e.g. reaction at a temperature from ambient (e.g. 25° C.) to 100° C. in the presence of an appropriate base (e.g. an alkali metal alkoxide, such as potassium tert-butoxide)).

(c) Compounds of formula VIII in which Y represents $(CH_2)_2$ may be prepared by reaction of a corresponding compound of formula IX with a compound of formula XV,

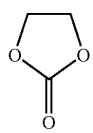

XV for example under conditions known to those skilled in the art (e.g. reaction at elevated temperature (e.g. above 80° C., such as from 120 to 130° C.) in the presence of a quaternary ammonium salt such as a tetra-n-butylammonium halide (e.g. tetra-n-butylammonium bromide or iodide) and an appropriate solvent (e.g. a hydrocarbon solvent such as xylene)-see, for example U.S. Pat. No. 4,885,396, the disclosures of which document are hereby incorporated by reference).

Compounds of formulae IX, X, XI, XII, XIII, XIV, XV and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and (if appropriate) heterocyclic, group(s) in compounds defined herein may be converted to other claimed substituents using techniques well known to those skilled in the art. For example, hydroxy may be converted to alkoxy, phenyl may be halogenated to give halophenyl, nitro may be reduced to give amino, halo may be displaced by cyano, etc.

The skilled person will also appreciate that various standard substituent or functional group interconversions and transformations within certain compounds of formula I will provide other compounds of formulae I. For example, hydroxy may be either reduced to alkylene or converted to halo.

The compounds of the invention may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for phenoxy include alkyl (i.e. ether) groups, such as methyl. Suitable protecting groups for amino include benzyl, sulfonamido (e.g. benzenesulfonamido), tert-butyloxycarbonyl, 9-fluorenyl-methoxycarbonyl or benzyloxycarbonyl. Suitable protecting groups for amidino and guanidino include benzyloxycarbonyl. Suitable protecting groups for carboxylic acid include $C_{1-6}$ alkyl or benzyl esters.

The protection and deprotection of functional groups may take place before or after any of the reaction steps described hereinbefore. Protecting groups may be removed in accordance with techniques which are well known to those skilled in the art and as described hereinafter.

The use of protecting groups is described in "Protective Groups in Organic Chemistry", edited by J. W. F. McOmie, Plenum Press (1973), and "Protective Groups in Organic Synthesis", $3^{rd}$ edition, T. W. Greene & P. G. M. Wutz, Wiley-Interscience (1999).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs". Moreover, certain compounds of formula I may act as prodrugs of other compounds of formula I.

All prodrugs of compounds of formula I are included within the scope of the invention.

Some of the intermediates referred to hereinbefore are novel. According to a further aspect of the invention there is thus provided:

(A) a compound of formula III in which X represents —(CH$_2$)$_3$— and L$^1$ represents R$^a$S(O)$_2$O— and R$^a$ represents methyl, phenyl (optionally substituted by 2 or 3 methyl groups, e.g. phenyl or 2,4,6-trimethylphenyl), nitrophenyl (e.g. 2-, 3- or 4-nitrophenyl) or chlorophenyl (e.g. 2-, 3- or, particularly, 4-chlorophenyl);

(B) a compound of formula V in which
L$^1$ represents bromo or, particularly, R$^a$S(O)$_2$O—,
Z represents O and
R$^3$ represents the structural fragment

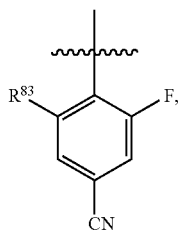

wherein R$^a$ and R$^{83}$ are as hereinbefore defined, or a protected derivative thereof; and (C) a compound of formula VIII in which R$^3$ represents the structural fragment

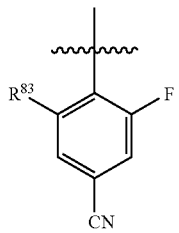

wherein R$^{83}$ is as hereinbefore defined, or a protected derivative thereof.

The compounds defined at (B) and (C) above in which L$^1$ represents R$^a$S(O)$_2$O— can alternatively be represented as compounds of formulae XV and XVI, respectively,

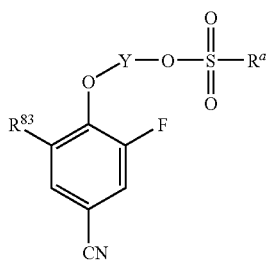

XV

-continued

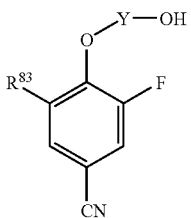

XVI wherein R$^{83}$, R$^a$ and Y are as hereinbefore defined.

Compounds of formulae V, XV and XVI that may be mentioned include those in which:
Y represents —(CH$_2$)$_4$—, —(CH$_2$)$_3$— or, particularly, —(CH$_2$)$_2$—;
R$^{83}$ represents H.

Values of R$^a$ that may be mentioned in relation to compounds of formula XV include phenyl optionally substituted by one or more (e.g. one to three) methyl groups (e.g. 2,4,6-trimethylphenyl or, particularly, 4-methylphenyl).

Specific compounds of formula V in which L$^1$ represents bromo that may be mentioned include 4-(2-bromoethoxy)-3-fluorobenzonitrile.

Specific compounds of formula XV that may be mentioned include 2-(4-cyano-2-fluorophenoxy)ethyl toluene-4-sulfonate.

Specific compounds of formula XVI that may be mentioned include 3-fluoro-4-(2-hydroxyethoxy)benzonitrile.

Medical and Pharmaceutical Use

Compounds of the invention are useful because they possess pharmacological activity. They are therefore indicated as pharmaceuticals.

Thus, according to a further aspect of the invention there is provided the compounds of the invention for use as pharmaceuticals.

In particular, the compounds of the invention exhibit myocardial electrophysiological activity, for example as demonstrated in the test described below.

The compounds of the invention are thus expected to be useful in both the prophylaxis and the treatment of arrhythmias, and in particular atrial and ventricular arrhythmias.

The compounds of the invention are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of the invention have been found to selectively delay cardiac repolarization and increase refractoriness.

According to a further aspect of the invention, there is provided a method of treatment of an arrhythmia which method comprises administration of a therapeutically effective amount of a compound of the invention to a person suffering from, or susceptible to, such a condition.

Pharmaceutical Preparations

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

According to a further aspect of the invention there is thus provided a pharmaceutical formulation including a compound of the invention in admixture with a pharmaceutically acceptable adjuvant, diluent or carrier.

Suitable daily doses of the compounds of the invention in therapeutic treatment of humans are about 0.005 to 50.0 mg/kg body weight at oral administration and about 0.005 to 15.0 mg/kg body weight at parenteral administration. Preferable ranges of daily doses of the compounds of the invention in therapeutic treatment of humans are about 0.005 to 20.0 mg/kg body weight at oral administration and about 0.005 to 10.0 mg/kg body weight at parenteral administration.

The compounds of the invention may also be combined with any other drugs useful in the treatment of arrhythmias and/or other cardiovascular disorders.

Thus, according to a further aspect of the invention, there is provided a combination product comprising:
(A) a compound of the invention, as hereinbefore defined, or a pharmaceutically acceptable derivative thereof; and
(B) an anticoagulant,
wherein each of components (A) and (B) is formulated in admixture with a pharmaceutically-acceptable adjuvant, diluent or carrier.

Such combination products provide for the administration of compounds of the invention in conjunction with the other therapeutic agent, and may thus be presented either as separate formulations, wherein at least one of those formulations comprises a compound of the invention and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, or a pharmaceutically acceptable derivative thereof, an anticoagulant, and a pharmaceutically-acceptable adjuvant, diluent or carrier; and
(2) a kit of parts comprising components:
   (a) a pharmaceutical formulation including a compound of the invention, as hereinbefore defined, or a pharmaceutically acceptable derivative thereof, in admixture with a pharmaceutically-acceptable adjuvant, diluent or carrier; and
   (b) a pharmaceutical formulation including an anticoagulant with a pharmaceutically-acceptable adjuvant, diluent or carrier,
   which components (a) and (b) are each provided in a form that is suitable for administration in conjunction with the other.

When used herein, the term "an anticoagulant" includes references to one a substance selected from the group consisting of aspirin, warfarin, enoxaparin, heparin, low molecular weight heparin, cilostazol, clopidogrel, ticlopidine, tirofiban, abciximab, dipyridamole, plasma protein fraction, human albumin, low molecular weight dextran, hetastarch, reteplase, alteplase, streptokinase, urokinase, dalteparin, filgrastin, immunoglogulin, ginkolide B, hirudins, foropafant, rocepafant, bivalirudin, dermatan sulfate mediolanum, eptilibatide, tirofiban, thrombomodulin, abcxmab, low molecular weight dermatan sulfate-opocrin, eptacog alfa, argatroban, fondaparinux sodium, tifacogin, lepirudin, desirudin, OP2000, roxifiban, parnaparin sodium, human hemoglobin (Hemosol), bovine hemoglobin (Biopure), human hemoglobin (Northfield), antithrombin III, RSR 13, heparin-oral (Emisphere) transgenic antithrombin III, H37695, enoxaparin sodium, mesoglycan, CTC 111, bivalirudin, and any derivatives and/or combinations thereof.

Particular anticoagulants that may be mentioned include aspirin and warfarin.

The term "an anticoagulant" also includes references to thrombin inhibitors. Thrombin inhibitors that may be mentioned include low molecular weight thrombin inhibitors. The term "low molecular weight thrombin inhibitors" will be understood by those skilled in the art, and includes references to any composition of matter (e.g. chemical compound) that inhibits thrombin to an experimentally determinable degree (as determined by in vivo and/or in vitro tests), and which possesses a molecular weight of below about 2,000, preferably below about 1,000.

Preferred low molecular weight thrombin inhibitors include low molecular weight peptide-based, amino acid-based, and/or peptide analogue-based, thrombin inhibitors, as well as derivatives thereof.

The term "low molecular weight peptide-based, amino acid-based, and/or peptide analogue-based, thrombin inhibitors" will be well understood by one skilled in the art to include references to low molecular weight thrombin inhibitors with one to four peptide linkages, and includes those described in the review paper by Claesson in *Blood Coagul. Fibrin.* 5, 411 (1994), as well as those disclosed in U.S. Pat. No. 4,346,078, International Patent Applications WO 93/11152, WO 93/18060, WO 93/05069, WO 94/20467, WO 94/29336, WO 95/35309, WO 95/23609, WO 96/03374, WO 96/06832, WO 96/06849, WO 96/25426, WO 96/32110, WO 97/01338, WO 97/02284, WO 97/15190, WO 97/30708, WO 97/40024, WO 97/46577, WO 98/06740, WO 97/49404, WO 97/11693, WO 97/24135, WO 97/47299, WO 98/01422, WO 98/57932, WO 99/29664, WO 98/06741, WO 99/37668, WO 99/37611, WO 98/37075, WO 99/00371, WO 99/28297, WO 99/29670, WO 99/40072, WO 99/54313, WO 99/31504, WO 00/01704 and WO 00/08014; and European Patent Applications 648 780, 468 231, 559 046, 641779, 185 390, 526 877, 542 525, 195 212, 362 002, 364 344, 530 167, 293 881, 686 642, 669 317, 601 459 and 623 596, the disclosures in all of which documents are hereby incorporated by reference.

In the present application, derivatives of thrombin inhibitors include chemical modifications, such as esters, prodrugs and metabolites, whether active or inactive, and pharmaceutically acceptable salts and solvates, such as hydrates, of any of these, and solvates of any such salt.

Preferred low molecular weight peptide-based thrombin inhibitors include those known collectively as the "gatrans". Particular gatrans which may be mentioned include HOOC—CH₂—(R)Cha-Pic-Nag-H (known as inogatran) and HOOC—CH₂—(R)Cgl-Aze-Pab-H (known as melagatran) (see International Patent Application WO 93/11152 and WO 94/29336, respectively, and the lists of abbreviations contained therein).

International Patent Application WO 97/23499 discloses a number of compounds which have been found to be useful as prodrugs of thrombin inhibitors. Said prodrugs have the general formula

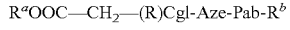

wherein $R^a$ represents H, benzyl or $C_{1-10}$ alkyl, $R^b$ (which replaces one of the hydrogen atoms in the amidino unit of Pab-H) represents OH, OC(O)$R^c$ or C(O)O$R^d$, $R^c$ represents $C_{1-17}$ alkyl, phenyl or 2-naphthyl and $R^d$ represents $C_{1-12}$ alkyl, phenyl, $C_{1-3}$ alkylphenyl, or 2-naphthyl. Preferred compounds include $R^a$OOC—CH₂—(R)Cgl-Aze-Pab-OH, wherein $R^a$ represents benzyl or $C_{1-10}$ alkyl, e.g. ethyl or isopropyl, especially EtOOC—CH$_2$—(R)Cgl-Aze-Pab-OH. The active thrombin inhibitors themselves are disclosed in WO 94/29336.

Further low molecular weight thrombin inhibitors that may be mentioned include those disclosed in WO 02/44145, such as compounds of the following general formula,

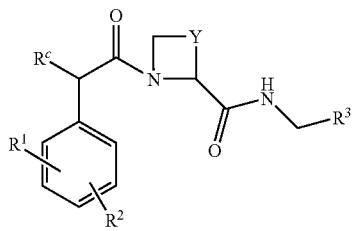

wherein
R$^c$ represents —OH or —CH$_2$OH;
R$^1$ represents at least one optional halo substituent;
R$^2$ represents one or two C$_{1-3}$ alkoxy substituents, the alkyl parts of which substituents are themselves substituted with one or more fluoro substituents (i.e.
R$^2$ represents one or two fluoroalkoxy(C$_{1-3}$) groups);
Y represents —CH$_2$— or —(CH$_2$)$_2$—; and
R$^3$ represents a structural fragment of formula I(i) or I(ii):

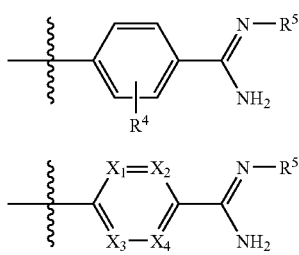

wherein
R$^4$ represents H or one or more fluoro substituents;
R$^5$ represents H, OR$^6$ or C(O)OR$^7$;
R$^6$ represents H, C$_{1-10}$ alkyl, C$_{1-3}$ alkylaryl or C$_{1-3}$ alkyloxyaryl (the alkyl parts of which latter two groups are optionally interrupted by one or more oxygen atoms, and the aryl parts of which latter two groups are optionally substituted by one or more substituents selected from halo, phenyl, methyl or methoxy, which latter three groups are also optionally substituted by one or more halo substituents);
R$^7$ represents C$_{1-10}$ alkyl (which latter group is optionally interrupted by one or more oxygen atoms), or C$_{1-3}$ alkylaryl or C$_{1-3}$ alkyloxyaryl (the alkyl parts of which latter two groups are optionally interrupted by one or more oxygen atoms, and the aryl parts of which latter two groups are optionally substituted by one or more substituents selected from halo, phenyl, methyl or methoxy, which latter three groups are also optionally substituted by one or more halo substituents); and
one or two of X$_1$, X$_2$, X$_3$ and X$_4$ represent —N— and the others represent —CH—;
or a pharmaceutically-acceptable derivative thereof.

Compounds of the above general formula in which R$^5$ is other than H have been found to be useful as prodrugs of thrombin inhibitors (which thrombin inhibitors include the corresponding compounds of the above general formula in which R$^5$ is H).

Particular compounds disclosed in WO 02/44145 that may be mentioned include those of the following general formula:

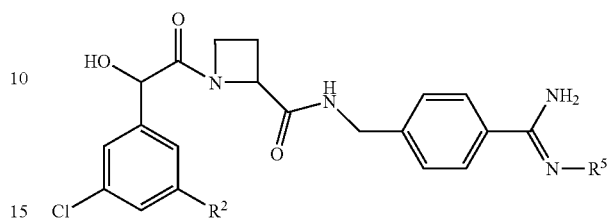

wherein
R$^2$ represents —OCHF$_2$, —OCF$_3$, —OCH$_2$CH$_2$F or —OCH$_2$CHF$_2$;
R$^5$ represents H or OR$^6$; and
R$^6$ represents methyl, ethyl, n-propyl, i-propyl or cyclobutyl.

In this respect, more particular compounds disclosed in WO 02/44145 that may be mentioned include the thrombin inhibitor Ph(3-Cl)(5-OCHF$_2$)—(R)CH(OH)C(O)-Aze-Pab and its methoxyamidino prodrug Ph(3-Cl)(5-OCHF$_2$)—(R)CH(OH)C(O)-Aze-Pab (OMe).

The compounds of the invention have the advantage that they are effective against cardiac arrhythmias.

Compounds of the invention have advantageous properties compared to compounds of the prior art, in particular enhanced potency, enhanced selectivity, and/or reduction of total clearance. These advantages may provide for corresponding useful properties in practice. For example, when used as pharmaceutical agents, compounds of the present invention may have a lower daily clinical dose, longer duration of action, and/or an improved side effect profile.

Compounds of the invention may also have the advantage that they may be more efficacious than, be less toxic than, have a broader range of activity (including exhibiting any combination of class I, class II, class III and/or class IV activity (especially class I and/or class IV activity in addition to class III activity)) than, be more potent than, be longer acting than, produce fewer side effects (including a lower incidence of proarrhythmias such as torsades de pointes) than, be more easily absorbed than, or that they may have other useful pharmacological properties over, compounds known in the prior art.

Biological Tests

Test A

Primary Electrophysiological Effects in Anaesthetised Guinea Pigs

Guinea pigs weighing between 500 and 1000 g were used. The animals were housed for at least one week before the experiment and had free access to food and tap water during that period.

Anaesthesia was induced by an intraperitoneal injection of pentobarbital (50 to 60 mg/kg) and catheters were introduced into one carotid artery (for blood pressure recording and blood sampling) and into one jugular vein (for drug infusions). Needle electrodes were placed on the limbs for recording of ECGs (lead II). A thermistor was placed in the rectum and the animal was placed on a heating pad, set to a rectal temperature of between 37.5 and 38.5° C.

A tracheotomy was performed and the animal was artificially ventilated with room air by use of a small animal ventilator, set to keep blood gases within the normal range for the species. In order to reduce autonomic influences both vagi were cut in the neck, and 0.5 mg/kg of propranolol was given intravenously, 15 minutes before the start of the experiment.

The left ventricular epicardium was exposed by a left-sided thoracotomy, and a custom-designed suction electrode for recording of the monophasic action potential (MAP) was applied to the left ventricular free wall. The electrode was kept in position as long as an acceptable signal could be recorded, otherwise it was moved to a new position. A bipolar electrode for pacing was clipped to the left atrium. Pacing (1 ms duration, twice the diastolic threshold) was performed with a custom-made constant current stimulator. The heart was paced at a frequency just above the spontaneous sinus rate during 30 s every fifth minute throughout the study.

The MAP signal, the blood pressure signal and the lead II ECG were collected (the sampling frequency was 1000 Hz and each sampling period 10 s) on a personal computer during the last 10 s of each 30 s pacing sequence and the last 10 s of the following min of sinus rhythm. The signals were processed using a custom-designed computer program (PharmLab v 4.0).

The test procedure consisted of two basal control recordings, 3 minutes apart, during both pacing and sinus rhythm. After the second control recording, the first dose of the test substance was infused in a volume of 0.2 mL/kg into the jugular vein catheter for 30 seconds. Three minutes later, pacing was started and a new recording was made. Five minutes after the previous dose, the next dose of test substance was administered. Six to ten consecutive doses were given during each experiment.

Data Analysis

Of the numerous variables measured in this analysis, three were selected as the most important for comparison and selection of active compounds. The three variables selected were the MAP duration at 75 percent repolarization during pacing, the atrio-ventricular (AV) conduction time (defined as the interval between the atrial pace pulse and the start of the ventricular MAP) during pacing, and the heart rate (defined as the RR interval during sinus rhythm). Systolic and diastolic blood pressure were measured in order to judge the haemodynamic status of the anaesthetised animal. Further, the ECG was checked for arrhythmias and/or morphological changes.

The mean of the two control recordings was set to zero and the effects recorded after consecutive doses of test substance were expressed as percentage changes from this value. By plotting these percentage values against the cumulative dose administered before each recording, it was possible to construct dose-response curves. In this way, each experiment generated three dose-response curves, one for MAP duration, one for AV-conduction time and one for the sinus frequency (RR interval). A mean curve of all experiments performed with a test substance was calculated, and potency values were derived from the mean curve. All dose-response curves in these experiments were constructed by linear connection of the data points obtained. The cumulative dose prolonging the MAP duration by 10% from the baseline was used as an index to assess the class III electrophysiological potency of the agent under investigation ($D_{10}$).

Test B

Rb$^+$-Efflux Assay for Detection of HERG Channel Blockers

The human ether-a-go-go related gene (HERG) encodes the voltage-gated K$^+$ channel underlying the cardiac rapid delayed rectifier current $I_{Kr}$. The IC50 value for HERG channel blockade was determined using a high throughput functional assay based on depolarisation-induced Rb$^+$-efflux from Chinese hamster ovary cells stably expressing the HERG-channel.

Cells were grown in Ham F12 (Life Technologies 31765-027) supplemented with 10% FBS and 0.6 mg/mL hygromycin B and were routinely passaged twice-weekly. For experimental studies, cells were plated at a density of 15,000 cells/well in Falcon, 384-well tissue culture-treated black-walled clear-bottomed plates and were thereafter incubated overnight at 37° C. in a cell culture incubator.

Following incubating overnight, cell plates were washed and a Rb$^+$-Load buffer (a physiological buffer containing Rb$^+$) was added. Cell plates were then incubated for 3 hours and were thereafter washed. Following this wash, the test compounds were added. The cell plates were then incubated for another 10 minutes and, following this incubation period, external K$^+$ concentration was increased in order to depolarize the cells and activate HERG channels. After a ten minute exposure period to the increased K$^+$ concentration, supernatants were transferred to new microplates for subsequent determination of Rb$^+$ content, using Atomic Absorption Spectrometry analysis.

The basal Rb$^+$ efflux (content of Rb$^+$ (mg/L) in supernatants of wells receiving only wash buffer) was defined as 100% inhibition and the stimulated Rb$^+$ efflux (content of Rb$^+$ (mg/L) in supernatants of wells exposed only to increased external potassium concentration) was defined as 0% inhibition.

Compound activity was expressed as:

$$100 \times \left[1 - \frac{A - B}{C - B}\right]$$

A: Rb$^+$ content in wells receiving test compound+increased external K$^+$.
B: Basal Rb$^+$ efflux.
C: Stimulated Rb$^+$ efflux.

The invention is illustrated by way of the following examples.

EXAMPLES

General Experimental Procedures

Mass spectra were recorded on one of the following instruments: MUX(8)-LCT, ZQ Masspectrometer and Quattro micro, all from Waters Micromass.

LC-MS:

Separation was performed using Agilent 1100 Series Modules on a Synergi MAX RP (3×50 mm, C12, 4 µm particles) with gradient elution. Samples were injected using a Waters 2700 Sample Manager.

Mobile phases: Generic gradients were applied from 5% to 95% acetonitrile.

Buffers containing 10 mM ammonium acetate or 5 mM ammonium formate/5 mM formic acid were used.

The mass spectra were recorded using a Waters ZQ2000 equipped with an electrospray or ESCI interface, switching positive and negative ionization mode. UV spectra were collected by a Agilent 1100 PDA and the evaporative light scattering (ELS) signal by a Sedere Sedex 55 or 75.

Data collection and evaluation were performed using the MassLynx software.

Accurate mass was determined using a LCT or Q-TOF micro mass spectrometer.

¹H NMR and ¹³C NMR measurements were performed on a BRUKER ACP 300 and Varian 300, 400, 500 and 600 Mercury, Unity plus and Unity Inova spectrometers, operating at ¹H frequencies of 300, 400, 500 and 600 MHz respectively and at ¹³C frequencies of 75.4, 100.6, 125.7 and 150.9 MHz respectively.

Rotamers may or may not be denoted in spectra depending upon ease of interpretation of spectra. Unless otherwise stated, chemical shifts are given in ppm with the solvent as internal standard.

Synthesis of Intermediates

The following intermediates were not commercially available, and were therefore prepared by the methods described below.

Preparation A tert-Butyl[3-(9-oxa-3,7-diazabicyclo[3.3.1]non-3-yl) propyl]carbamate tert-Butyl[3-(7-benzyl-9-oxa-3,7-diazabicyclo[3.3.1]non-3-yl)propyl]carbamate (0.85 g, 2.2 mmol; see Example 11 below) was dissolved in ethanol (10 mL). Palladium hydroxide (0.5 g) was then added and the reaction mixture was hydrogenated in Parr shaker under 2.45 bar pressure for 4 h. The reaction mixture was filtered and solvent concentrated under reduced pressure to give the title compound (0.71 g, 84%) as an orange solid.

Preparation B 3,5-Difluoro-4-[3-(9-oxa-3,7-diazabicyclo[3.3.1] non-3-yl)propoxy]benzonitrile hydrochloric acid salt (i) 4-Bromo-2,6-difluorophenol Bromine (13.54 g, 0.0846 mol) dissolved in acetic acid (40 mL) was added drop by drop to a cooled solution of 2,6-difluorophenol (20 g, 0.153 mol) in acetic acid (80 mL) and the reaction mixture was stirred at room temperature overnight. The reaction mixture was quenched with saturated aqueous sodium bisulfite solution and then extracted with dichloromethane. The organic layer was washed with water and brine and dried over sodium sulfate. Solvent evaporation under reduced pressure afforded 4-bromo-2,6-difluorophenol (21 g) as a yellow liquid. This was employed directly in the next step without further purification.

(ii) 4-Bromo-2,6-difluorophenyl methyl ether

Methyl iodide (17.11 g, 0.12 mol) was added at 0° C. to a well stirred suspension of 4-bromo-2,6-difluorophenol (21 g, 0.1 mol; see step (i) above) and $K_2CO_3$ (27.78 g, 0.2 mol) in dry acetone (150 mL). Stirring was continued at 60° C. overnight under a nitrogen atmosphere. The reaction mixture was filtered, the solvent was evaporated and the residue was purified by column chromatography over silica gel, using petroleum ether as eluent, to give 11.5 g of the sub-title compound as a colourless liquid.

(iii) 3,5-Difluoro-4-methoxybenzonitrile

A mixture of 4-bromo-2,6-difluorophenyl methyl ether (11.5 g, 0.0516 mol; see step (ii) above) and CuCN (6.92 g, 0.0774 mol) in dry DMF (15 mL) was stirred at 120° C. for two days under nitrogen atmosphere. The reaction mixture was cooled to room temperature, diluted with water and extracted with ethyl acetate. The organic layer was washed with water and brine and dried over sodium sulfate. Solvent evaporation under reduced pressure followed by column chromatography over silica gel, using 2% ethyl acetate in petroleum ether as eluent, yielded 2.7 g of the sub-title compound as a pale yellow solid.

(iv) 3,5-Difluoro-4-hydroxybenzonitrile $BBr_3$ (6.61 g, 0.0264 mol) was added to 3,5-difluoro-4-methoxybenzonitrile (1.5 g, 0.0088 mol; see step (iii) above) in dichloromethane (15 mL) at −78° C. Stirring was continued at room temperature overnight under a nitrogen atmosphere. The reaction mixture was then quenched with ice water and extracted with dichloromethane. The organic layer was washed with water and brine, and dried over sodium sulfate. Solvent evaporation under reduced pressure yielded 1.1 g (80.6%) of the sub-title compound as a grey solid.

(v) 4-(3-Bromopropoxy)-3,5-difluorobenzonitrile

A mixture of 3,5-difluoro-4-hydroxybenzonitrile (2.1 g, 0.0136 mol; see step (iv) above), $K_2CO_3$ (3.76 g, 0.0272 mol) and 1,3-dibromopropane (16.48 g, 0.0816 mol) in dry DMF (50 mL) was stirred at 60° C. overnight under a nitrogen atmosphere. The reaction mixture was filtered through Celite® and partitioned between water and ethyl acetate. The organic layer was washed with water and brine and then dried over sodium sulfate. Solvent evaporation under reduced pressure provided a residue that was purified by column chromatography over silica gel, using 2.5% ethyl acetate in petroleum ether as eluent, to yield 1.5 g (20%) of the sub-title compound as a yellow liquid.

(vi) tert-Butyl 7-[3-(4-cyano-2,6-difluorophenoxypropyl]-9-oxa-3,7-diazabicyclo[3.3.1]nonane-3-carboxylate A suspension of 4-(3-bromopropoxy)-3,5-difluorobenzonitrile (1.5 g, 0.0054 mol; see step (v) above), 9-oxa-3,7-diazabicyclo[3.3.1]nonane-3-carboxylic acid tert-butyl ester HCl-salt (1.46 g, 4.8 mmol, see WO 01/28992) and dry $K_2CO_3$ (2.25 g, 0.0162 mol) in 35 mL of dry acetonitrile was stirred at 60° C. for 3 days under a nitrogen atmosphere. The reaction mixture was filtered through Celite® and the filtrate was then concentrated under reduced pressure. The residue was purified by column chromatography over silica gel, using 20% ethyl acetate in petroleum ether as eluent, to yield 1.1 g (54%) of the sub-title compound as a colourless, gummy liquid.

(vii) 3,5-Difluoro-4-[3-(9-oxa-3,7-diazabicyclo [3.3.1]non-3-yl)propoxy]-benzonitrile HCl-salt Dioxane (20 mL, saturated with HCl gas) was added to a solution of tert-butyl 7-[3-(4-cyano-2,6-difluorophenoxy) propyl]-9-oxa-3,7-diazabicyclo[3.3.1]nonane-3-carboxylate (1.1 g, 2.6 mmol; see step (vi) above) in 5 mL of dry dioxane. The resulting mixtures was stirred for 1 h at RT under a nitrogen atmosphere. Dioxane was decanted before the solid that had precipitated was isolated by filtration and then washed with dry diethyl ether (3 times) and dried under vacuum. This yielded 1.2 g of the title compound as a white powder. This was employed directly (i.e. without further purification) in the preparation of further compounds.

API-MS: (M+1)=324.3

Preparation C

3,5-Difluoro-4-[2-(9-oxa-3,7-diazabicyclo[3.3.1]non-3-yl)ethoxy]benzonitrile hydrochloric acid salt (i) 4-(2-Bromoethoxy)-3,5-difluorobenzonitrile A suspension of 3,5-difluoro-4-hydroxybenzonitrile (10 g, 0.0649 mol; see Preparation B(iv) above), anhydrous $K_2CO_3$ (17.94 g, 0.1298 mol) and 1,2-dibromoethane (73.2 g, 0.389 mol) in dry DMF (100 mL) was stirred at 60° C. overnight under a nitrogen atmosphere. The reaction mixture was filtered through Celite® and the solvent was then evaporated under reduced pressure. The residue was purified by column chromatography over silica gel, using 1.5% ethyl acetate in petroleum ether as eluent, to yield 12 g of the sub-title compound as a white solid.

(ii) tert-Butyl 7-[2-(4-cyano-2,6-difluorophenoxy)ethyl]-9-oxa-3,7-diazabiclo-[3.3.1]nonane-3-carboxylate A suspension of 4-(2-bromoethoxy)-3,5-difluorobenzonitrile (12 g, 45.8 mmol; see step (i) above), 9-oxa-3,7-diazabicyclo[3.3.1]nonane-3-carboxylic acid tert-butyl ester HCl-salt (11.5 g, 0.0435 mol; see WO 01/28992) and dry $K_2CO_3$ (25.32 g, 0.183 mol) in 140 mL of dry acetonitrile was stirred at 60° C. for five days under a nitrogen atmosphere. The reaction mixture was filtered through Celite® and the filtrate was then concentrated under reduced pressure. The residue was purified by column chromatography over silica gel, using 20% ethyl acetate in petroleum ether as eluent, to yield 12.55 g of the sub-title compound as a white solid.

(iii) 3,5-Difluoro-4-[2-(9-oxa-3,7-diazabicyclo[3.3.1]non-3-yl)ethoxy]benzonitrile hydrochloric acid salt tert-Butyl 7-[2-(4-cyano-2,6-difluorophenoxy)ethyl]-9-oxa-3,7-diazabicyclo-[3.3.1]nonane-3-carboxylate (12.35 g, 30.6 mmol; see step (ii) above) was dissolved in 20 mL of dioxane before 100 mL of dioxane (saturated with HCl gas) was added. The resulting mixture was stirred for 1 h at RT under a nitrogen atmosphere. The solvent was decanted and the precipitated solid was washed with dry diethyl ether (4 times) and then dried under vacuum to give 12.35 g of the title compound as a white solid.

$^{13}$C-NMR (125 MHz, $D_2O$): δ 158.07, 156.08, 119.74, 119.56, 107.88, 71.82, 66.21, 59.16, 56.61, 47.26.

Preparation D

3-Fluoro-4-[2-(9-oxa-3,7-diazabicyclo[3.3.1]non-3-yl)ethoxy]benzonitrile hydrochloric acid salt (i) 4-Bromo-2-fluorophenol Bromine (68.7 mL, 1.339 mol) dissolved in acetic acid (300 mL) was added drop by drop to a cooled solution of 2-fluorophenol (150 g, 1.339 mol) in acetic acid (1300 mL). The resulting mixture was stirred at room temperature overnight before being quenched with aqueous sodium bisulfite solution and extracted with dichloromethane. The organic layer was washed with water and brine and then dried over sodium sulfate. Solvent evaporation under reduced pressure afforded 4-bromo-2-fluorophenol (210 g) as a liquid. This was employed directly in the next step without further purification.

(ii) 4-Bromo-2-fluoro-1-methoxybenzene

Methyl iodide (182.1 mL, 1.319 mol) was added at 0° C. to a well stirred suspension of 4-bromo-2-fluorophenol (210 g, 1.099 mol; see step (i) above) and $K_2CO_3$ (303.92 g, 2.19 mol) in dry acetone (1.7 L). Stirring was continued at 60° C. for two days under a nitrogen atmosphere before the reaction mixture was filtered and the solvent was concentrated under reduced pressure. This provided 4-bromo-2-fluoro-1-methoxybenzene (225 g) as a liquid, which was employed directly in the next step without further purification.

(iii) 3-Fluoro-4-methoxybenzonitrile

A mixture of 4-bromo-2-fluoro-1-methoxybenzene (107 g, 0.52 mol; see step (ii) above), CuCN (70.4 g, 0.78 mol) in dry DMF (150 mL) was stirred at 120° C. overnight. The reaction mixture was cooled to room temperature, diluted with water and extracted with ethyl acetate. The organic layer was washed with water and brine and then dried over sodium sulfate. Solvent evaporation under reduced pressure, followed by column chromatography over silica gel using 3% ethyl acetate in petroleum ether as eluent, gave 24.4 g of the sub-title compound as a solid.

(iv) 3-Fluoro-4-hydroxybenzonitrile $BBr_3$ (23 mL, 0.242 mol) was added to 3-fluoro-4-methoxy-benzonitrile (24.4 g, 0.16 mol; see step (iii) above) in dichloromethane (200 mL) at −78° C. Stirring was continued at room temperature overnight. Another portion of $BBr_3$ (23 mL, 0.242 mol) was added at −78° C. and stirring was continued at RT for a further 2 days under a nitrogen atmosphere. The reaction mixture was quenched with ice water and extracted with dichloromethane. The organic layer was washed with water and brine, and then dried over sodium sulfate. Solvent evaporation under reduced pressure gave 20 g of the sub-title compound as a solid. This was employed directly in the next step without further purification.

(v) 4-(2-Bromoethoxy)-3-fluorobenzonitrile

A suspension of 3-fluoro-4-hydroxybenzonitrile (20 g, 0.1459 mol; see step (iv) above), anhydrous $K_2CO_3$ (40.33 g, 0.2918 mol) and 1,2-dibromoethane (76.8 mL, 0.8754 mol) in dry DMF (150 mL) was stirred at 60° C. for 5 days under a nitrogen atmosphere. The reaction mixture was filtered through Celite® and the solvent was evaporated under reduced pressure. The residue was purified by column chromatography over silica gel, using 2% ethyl acetate in petroleum ether as eluent, to yield 21.6 g of the sub-title compound as a solid.

(vi) 7-[2-(4-Cyano-2-fluorophenoxyethyl]-9-oxa-3,7-diazabicyclo[3.3.1]nonane-3-carboxylic acid tert-butyl ester A suspension of 4-(2-bromoethoxy)-3-fluorobenzonitrile (21.6 g, 0.0885 mol; see step (v) above), 9-oxa-3,7-diazabicyclo[3.3.1]nonane-3-carboxylic acid tert-butyl ester (21.1 g, 0.07965 mol; see WO 01/28992) and dry $K_2CO_3$ (48.9 g, 0.354 mol) in 200 mL of dry acetonitrile was stirred at 60° C. for five days under a nitrogen atmosphere. The reaction mixture was filtered through Celite® and the filtrate was concentrated under reduced pressure. The residue was purified by

(vii) 3-Fluoro-4-[2-(9-oxa-3,7-diazabicyclo[3.3.1] non-3-yl)ethoxy]benzonitrile hydrochloric acid salt 7-[2-(4-Cyano-2-fluorophenoxy)ethyl]-9-oxa-3,7-diazabicyclo[3.3.1]nonane-3-carboxylic acid tert-butyl ester (20.5 g; see step (vi) above) was dissolved in 20 mL of dioxane, to which was added 100 mL of dioxane (saturated with HCl gas). The resulting mixture was stirred for 1 h at RT under a nitrogen atmosphere. Solvent was decanted and the precipitated solid was washed with dry diethyl ether (4 times) and dried under vacuum to provide 21 g of the title salt as a solid.

$^1$H-NMR (300 MHz, D$_2$O): δ 7.50-7.46 (2H, m), 7.19-7.15 (1H, m), 4.31 (2H, t), 4.19 (2H, bs), 3.64 (2H, m), 3.47-3.42 (4H, m), 3.23-3.19 (2H, m), 2.95 (4H, bs)

API-MS: (M+1)=292.1

Preparation E

3-Fluoro-4-[3-(9-oxa-3,7-diazabicyclo[3.3.1]non-3-yl)propoxy]benzonitrile

(i) 4-(3-Bromopropoxy)-3-fluorobenzonitrile

A mixture of 4-cyano-2-fluorophenol (8.5 g, 0.0620 mol; see Preparation D(iv) above), anhydrous K$_2$CO$_3$ (17.14 g, 0.124 mol) and 1,3-dibromopropane (37.7 mL, 0.372 mol) in dry DMF (80 mL) was stirred at 60° C. for 3 days under a nitrogen atmosphere. The reaction mixture was filtered through Celite® and the solvent was then evaporated under reduced pressure. The residue was purified by column chromatography over silica gel, using 4% ethyl acetate in petroleum ether, as eluent, to yield 8.2 g of the sub-title compound as a white solid.

(ii) tert-Butyl 7-[3-(4-cyano-2-fluorophenoxypropyl]-9-oxa-3,7-diazabicyclo-[3.3.1]nonane-3-carboxylate A suspension of 4-(3-bromopropoxy)-3-fluorobenzonitrile (8.2 g, 0.0318 mol; see step (i) above), 9-oxa-3,7-diazabicyclo[3.3.1]nonane-3-carboxylic acid tert-butyl ester (8.58 g, 0.0325; see WO 01/28992) and dry K$_2$CO$_3$ (22.58 g, 0.165 mol) in 100 mL of dry acetonitrile was stirred at 60° C. for two days under a nitrogen atmosphere. The reaction mixture was filtered through Celite® and the filtrate was concentrated under reduced pressure. The residue was purified by column chromatography over silica gel using 45% ethyl acetate in petroleum ether as eluent to yield 9.15 g of the sub-title compound as a yellow solid.

(iii) 3-Fluoro-4-[3-(9-oxa-3,7-diazabicyclo[3.3.1] non-3-yl)propoxy]benzonitrile hydrochloric acid salt tert-Butyl 7-[3-(4-cyano-2-fluorophenoxy)propyl]-9-oxa-3,7-diazabicyclo[3.3.1]-nonane-3-carboxylate (9.15 g, 22.5 mmol; see step (ii) above) was taken in 15 mL of dioxane, to which was added 75 mL of diethyl ether saturated with HCl gas. The resulting mixture was stirred for 1 h at RT under a nitrogen atmosphere before solvent was decanted and the precipitated solid washed with dry diethyl ether (4 times) and dried under vacuum. This gave 9 g of the sub-title compound as a pale yellow solid.

(iv) 3-Fluoro-4-[3-(9-oxa-3,7-diazabicyclo[3.3.1] non-3-yl)propooxy]benzonitrile 3-Fluoro-4-[3-(9-oxa-3,7-diazabicyclo[3.3.1]non-3-yl) propoxy]benzonitrile hydrochloric acid salt (6.54 g, 17.30 mmol; see step (iii) above) was mixed with K$_2$CO$_3$ (15.94 g, 115.34 mmol), acetonitrile (250 mL) and water (5 mL). The mixture was stirred at RT overnight, filtered and then evaporated, which gave 5.2 g of the title compound.

$^{13}$C-NMR (125 MHz, CDCl$_3$): δ 153.08, 151.46, 151.08, 129.90, 120.0, 119.87, 118.21, 114.78, 104.30, 68.203, 67.94, 58.13, 56.21, 50.69, 26.35.

Preparation F

4-(3-bromopropoxy)isophthalonitrile

(i) 2,4-Dibromo-1-methoxybenzene

K$_2$CO$_3$ (34.5 g, 0.243 mol) was added to a solution of 2,4-dinitrophenol (25 g, 0.009 mol) in acetonitrile (250 mL) and stirred for 10 minutes. The reaction mixture was cooled to 0° C., methyl iodide (15 mL, 0.240 mol) was added and the reaction mixture was stirred at 60° C. for 12 h under a nitrogen atmosphere. The reaction mixture was cooled to RT and filtered through a Celite® bed. The filtrate was concentrated under reduced pressure to afford 2,4-dibromo-1-methoxybenzene (26 g, 98.8%) as brown solid product. This was employed directly in the next step without further purification.

(ii) 4-Methoxyisophthalonitrile 2,4-Dibromo-1-methoxybenzene (25 g, 0.094 mol; see step (i) above) was dissolved in dry DMF (50 mL). CuCN (25.3 g, 0.283 mol) was then added and the resulting mixture was stirred at 120° C. for 15 h, before being cooled to RT. The crude mixture was diluted with water and extracted with ethyl acetate. The organic layer was washed with water and brine, dried over anhydrous Na$_2$SO$_4$ and concentrated under reduced pressure. The residue was purified by column chromatography over silica gel, using 25% ethyl acetate in petroleum ether as eluent, to yield the sub-title compound (7.1 g, 24%) as pale yellow solid.

(iii) 4-Hydroxyisophthalonitrile

4-Methoxyisophthalonitrile (2 g, 0.12 mol; see step (ii) above) was dissolved in quinoline (20 mL) and TMSI (2.7 mL, 0.018 mol) was added. The reaction mixture was stirred at 120° C. for 14 h, before being cooled to RT, acidified with conc. HCl and extracted with ethyl acetate. The organic layer was washed with 10% aqueous NaOH and the aqueous layer was acidified with 1 N HCl. The product was extracted with ethyl acetate, washed with water and brine and dried over Na$_2$SO$_4$. Solvent evaporation under reduced pressure afforded the sub-title compound (1.1 g, 61%) as pale brown solid. This was employed directly in the next step without further purification.

(iv) 4-(3-Bromopropoxy)isophthalonitrile

4-Hydroxyisophthalonitrile (4.4 g, 0.03 mol; see step (iii) above) was dissolved in dry DMF (100 mL). 1,3-Dibromopropane (36 g, 0.12 mol) and K$_2$CO$_3$ (8.2 g, 0.06 mol) were added. Then the reaction mixture was then stirred at 60° C. for 15 h before being cooled to RT and filtered through a Celite® bed. The filtrate was diluted with water and extracted with ethyl acetate. The organic layer was washed with water and brine, dried over anhydrous $Na_2SO_4$ and concentrated under reduced pressure. The residue was purified by column chromatography over silica gel, using 2% ethyl acetate in petroleum ether as eluent, to yield the title compound (5.1 g, 63%) as pale yellow solid.

Preparation G

2-[(4-Cyanobenzyl)oxy]ethyl methanesulfonate (i) 4-[(2-Hydroxyethoxy)methyl]benzonitrile NaH (2.4 g of a 60% suspension in mineral oil, 60 mmol) was washed twice with heptane (2×20 mL). Dry THF (20 mL) and ethylene glycol (24.8 g, 400 mmol) were added in portions over the course of 15 minutes (which resulted in an exothermic reaction and the evolution of gas). The resulting mixture was stirred for 2 h at RT. The mixture was then warmed to 80° C. and, after 20 minutes, benzyl bromide (7.84 g, 40 mmol) was added in portions over the course of 60 minutes. The reaction mixture was then stirred at 80° C. for 2 h, before being cooled to RT. Saturated $NH_4Cl$ solution (150 mL) was added slowly and the resulting mixture was extracted with diethyl ether (3×100 mL), washed with aqueous $NH_4Cl$ solution and brine, dried over $Na_2SO_4$ and then evaporated and purified by chromatography on silica (heptane: ethyl acetate (60:40) eluent). This gave 5.5 g (76.5%) of the sub-title compound.

(ii) 2-[(4-Cyanobenzyl)oxy]ethyl methanesulfonate

4-[(2-Hydroxyethoxy)methyl]benzonitrile (5.5 g, 30.5 mmol; see step (i) above) was dissolved in DCM (61 mL) and cooled to −10° C. Triethylamine (5 mL, 36.5 mmol) and methanesulfonyl chloride (3.84 g, 33.5 mmol) were added and the resulting mixture was stirred at below −5° C. for 1.5 h and then at RT overnight. Dichloromethane (200 mL) was added and the mixture was washed with water (2×100 mL) and then dried over $Na_2SO_4$. Evaporation of solvents gave 7.3 g (94%) of the title compound, which was used without further purification.

Preparation H

4-[2-(2-Bromoethoxy)ethyl]benzonitrile (i) 2-(4-Bromophenyl)ethanol

To a chilled solution (about 0° C.) of 4-bromophenyl acetic acid (25 g, 0.116 mol) in THF (250 mL), borane methyl sulphide (13.2 g, 0.174 mol) was added, dropwise, under nitrogen atmosphere. The reaction mixture was stirred at room temperature for 3 h. After cooling the mixture to between 0 and 5° C., the reaction was quenched by adding 1.5 N HCl (80 mL), dropwise. After warming for 30 min at about 80° C., the reaction mixture was extracted with ethyl acetate (2×100 mL). The combined organic extracts were washed with water and brine and then dried. The product was obtained as colourless liquid after concentration (yield: 23.3 g, 99%).

(ii) [2-(4-Bromophenyl)ethoxy]acetic acid

To a suspension of NaH (9.6 g, 0.4 mol) in DMF (100 mL), a solution of 2-(4-bromophenyl)ethanol (20.1 g, 0.1 mol; see step (i) above) in DMF (100 mL) was added, at 0° C. The resulting mixture was then stirred for 45 minutes at room temperature. After cooling the reaction mixture to 0° C., a solution of chloroacetic acid (9.4 g, 0.1 mol) in DMF (50 mL) was added, and the resulting mixture was stirred at 55 to 60° C. for 3 h. The reaction was quenched by adding cold (about 0° C.) water and then acidification to pH 2.0 (by addition of 1.5 N HCl). The mixture was extracted with ethyl acetate (5×200 mL) and the combined organic layers were washed with water and brine. The sub-title compound was isolated as pale brown solid after evaporation (yield: 14 g, 54%).

(iii) 2-[2-(4-Bromophenyl)ethoxy]ethanol

To a solution of [2-(4-bromophenyl)ethoxy]acetic acid (14 g, 0.054 mol; see step (ii) above) in dry THF (150 mL), borane methyl sulphide (6.16 g, 0.082 mol) was added, dropwise at from 0 to 5° C. The resulting mixture was stirred at room temperature for 3 h. After cooling the reaction mixture to between 0 and 5° C., 1.5 N HCl (80 mL) was added, dropwise, and the resulting mixture was refluxed for 30 minutes. The reaction mixture was cooled to room temperature and extracted with ethyl acetate (2×100 mL). The combined organic layers were washed with water and brine and concentrated to give the sub-title compound (yield: 10.8 g, 81%).

(iv) 2-[2-(4-Cyanophenyl)ethoxy]ethanol

To a solution of 2-[2-(4-bromophenyl)ethoxy]ethanol (10.8 g, 0.044 mol; see step (iii) above in DMF (100 mL), CuCN (7.8 g, 0.088 mol) was added and refluxed at 140 to 150° C. overnight. After removal of DMF by distillation, the reaction was quenched by the addition of water. Inorganic matter was removed by filtration and the aqueous layer was extracted with ethyl acetate (4×100 mL). The combined organic layers were washed with water and brine before being concentrated. The crude product was purified by column chromatography (silica gel: 60-120 mesh, petroleum ether: ethyl acetate (75:25) eluent). This yielded 4.3 g (51%) of the sub-title compound.

(v) 4-[2-(2-Bromoethoxy)ethyl]benzonitrile

To a solution of 2-[2-(4-cyanophenyl)ethoxy]ethanol (4.3 g, 0.0225 mol; see step (iv) above) in DCM (50 mL), triphenylphosphine (11.8 g, 0.045 mol) was added. The resulting mixture was stirred for 15 min and cooled to between 0 and 5° C. A solution of $CBr_4$ (14.9 g, 0.045 mol) in DCM (25 mL) was added dropwise and the resulting mixture was stirred at room temperature overnight. The reaction mixture was concentrated and the crude product was purified by column chromatography (silica gel: 60-120 mesh, petroleum ether: ethyl acetate (70:30) eluent) to provide the title compound (yield: 4.8 g, 84%).

Preparation I tert-Butyl (3-bromopropyl)carbamate $(Boc)_2O$ (13.5 g, 0.062 mol) was added drop by drop at 0° C. to a solution of 3-bromopropylamine hydrobromide (15 g, 0.0688 mol) and triethylamine (13.89 g, 0.1376 mol) in dry dichloromethane (125 mL) under a nitrogen atmosphere. The reaction mixture was stirred at RT for 1 h and quenched with water. The organic layer was washed with water and brine and dried over sodium sulfate. Solvent evaporation under reduced pressure, followed by purification over silica gel using 5% ethyl acetate in petroleum ether as eluent afforded 11.6 g of the title compound as yellow oil.

Preparation J 4-(9-Oxa-3,7-diazabicyclo[3.3.1]non-3-ylmethyl)benzonitrile, hydrochloride (i) 7-(4-Cyanobenzyl)-9-oxa-3,7-diazabicyclo[3.3.1]nonane-3-carboxylic acid tert-butyl ester A suspension of 4-bromomethylbenzonitrile (10 g, 0.054 mol), 9-oxa-3,7-diazabicyclo[3.3.1]nonane-3-carboxylic acid tert-butyl ester (11.5 g, 0.0439 mol; see WO 01/28992) and dry $K_2CO_3$ (21.2 g, 0.153 mol) in 200 µL of dry acetonitrile was stirred at 60° C. overnight under a $N_2$ atmosphere. The reaction mixture was filtered through Celite® and the filtrate was concentrated under reduced pressure. The residue was purified by column chromatography over silica gel using 10% ethyl acetate in petroleum ether as eluent to yield 10 g of the sub-title compound as colourless liquid.

(ii) 4-(9-Oxa-3,7-diazabicyclo[3.3.1]non-3-ylmethyl)benzonitrile, hydrochloride 7-(4-Cyanobenzyl)-9-oxa-3,7-diazabicyclo[3.3.1]nonane-3-carboxylic acid tert-butyl ester (10 g; see step (i) above) was taken in 15 mL of dioxane (saturated with HCl gas) and stirred for 1 h at RT under a nitrogen atmosphere. Dioxane was decanted, the precipitated solid was filtered, washed with dry diethyl ether (4 times) and dried under vacuum to give the title salt (7.5 g) as a powder. This was directly taken for next step without further purification. This was employed directly in the next step without further purification.

Preparation K 2-(4-Cyano-2-fluorophenoxy)ethyl toluene-4-sulfonate

Alternative 1

(i) 3-Fluoro-4-(2-hydroxyethoxy)benzonitrile

To potassium tert-butoxide (19.35 g) was added ethylene glycol (160 mL). The mixture was then heated to 50° C. At 50° C., 3,4-difluorobenzonitrile (20 g) was added and this was washed in with ethylene glycol (40 mL). The combined solution was heated to 80° C., and held at this temperature for two hours, before being cooled to 20° C. over one hour. The reaction mixture was filtered and washed with ethylene glycol (40 mL). To the filtrate was added water (200 mL) and dichloromethane (200 mL). The layers were separated and the organic layer was concentrated in vacuo, to give the sub-title compound as a waxy white solid (26.1 g, 100% yield).

$^1$H-NMR (CDCl$_3$, 300 MHz) δ 7.48-7.34 (m, 2H, CH$_{ar}$), 7.05 (t, J=8.3 Hz, 1H, CH$_{ar}$, 4.21 (t, J=4.5 Hz, 2H, C$\underline{H}_2$), 4.08-3.98 (m, 2H, CH$_2$).

If necessary, 3-fluoro-4-(2-hydroxyethoxy)benzonitrile can be recrystallised using the following procedure.

To 3-fluoro-4-(2-hydroxyethoxy)benzonitrile (4.0 g) was added toluene (20 mL), and this mixture was heated to 65° C. At 65° C., all of the material had dissolved. The mixture was allowed to cool to room temperature (approximately 20° C.). Crystallisation was noticed at between 45 and 40° C. The reaction mixture was further cooled to 5° C. The reaction mixture was filtered and was washed with toluene (5 mL). The damp solid was dried in vacuo, at 35° C., to give the purified sub-title compound as an off-white, crystalline solid (3.38 g; 85% yield).

$^1$H-NMR (CDCl$_3$, 300 MHz) δ 7.46-7.34 (m, 2H, CH$_{ar}$), 7.04 (t, J=8.3 Hz, 1H, CH$_{ar}$CF$_{ar}$), 4.21 (t, J=4.5 Hz, 2H, C$_{ar}$OCH$_2$), 4.03 (q, J=5.1 Hz, 2H, C$\underline{H}_2$OH), 2.09 (t, J=6.3 Hz, 1H, O$\underline{H}$).

(ii) 2-(4-Cyano-2-fluorophenoxy)ethyl toluene-4-sulfonate

To 3-fluoro-4-(2-hydroxyethoxy)benzonitrile (47.6 g; see step (i) above) was added dichloromethane (380 mL). To this was added triethylamine (55 mL) and then, over approximately sixty minutes, a solution of para-toluenesulfonyl chloride (50 g) dissolved in dichloromethane (380 mL). Water (380 mL) was added to the resulting mixture and the layers were separated. The lower (organic) layer was concentrated in vacuo to give the title compound as a white solid (87.9 g; 99.8%).

Recrystallisation of the title compound can be carried out, if necessary, using any of the methods below.

Method 1

To 2-(4-cyano-2-fluorophenoxy)ethyl toluene-4-sulfonate (167.7 g) was added ethyl acetate (1.65 L). This mixture was then heated to reflux (approximately 78° C.), at which point all of the material had dissolved. The reaction mixture was allowed to cool to room temperature (approximately 20° C.). Crystallisation was noticed at between 70° C. and 75° C. The reaction mixture was cooled to 5° C. The mixture was filtered, and was washed with ethyl acetate (165 mL). The damp solid was dried in vacuo, at 35° C., to give purified title compound as a white, crystalline solid (103.3 g; 61.6%).

Method 2

To 2-(4-cyano-2-fluorophenoxy)ethyl toluene-4-sulfonate (10 g) was added toluene (75 mL) and acetonitrile (5 mL). This mixture was heated to 80° C. At 80° C., all of the material had dissolved. The reaction mixture was cooled to room temperature (approximately 20° C.). Crystallisation was noticed at between 55 and 50° C. The reaction mixture was further cooled to 5° C. The mixture was filtered, and the solid was washed with toluene (10 mL). The damp solid was dried in vacuo, at 35° C., for approximately eighteen hours, to give purified title compound as an off-white crystalline solid (9 g, 90% yield).

Method 3

To 2-(4-cyano-2-fluorophenoxy)ethyl toluene-4-sulfonate (10 g) was added toluene (75 mL). This mixture was heated to 95° C. At 95° C., all of the material had dissolved. The reaction mixture was cooled to room temperature (approximately 20° C.). Crystallisation was noticed at between 65 and 60° C. The reaction mixture was further cooled to 5° C. The mixture was filtered, and the solid was washed with toluene (10 mL). The damp solid was dried in vacuo, at 35° C., for approximately seventeen hours, to give purified title compound as an off-white crystalline solid (9.4 g, 94% yield).

Alternative 2

To 3-fluoro-4-hydroxybenzonitrile (0.2 kg) was added acetonitrile (0.85 L), at 20° C. To this was added potassium carbonate (404 g); this was washed in with acetonitrile (0.18 L). The reaction was then heated to 80° C.±5° C., at approximately 1° C. per minute. When the reaction mixture was at 80° C.±5° C., 2-bromoethan-1-ol (0.31 L) was added, over approximately twenty minutes. This was washed in with acetonitrile (0.18 L). The temperature was adjusted to 80° C. ±5° C., and maintained at this temperature for six hours. The reaction mixture was then cooled to 30° C., at approximately 1° C. per minute. For convenience, the reaction was held at 30° C. for approximately 12 hours. Toluene (1.6 L) and water (1.34 L) were then added to the reaction mixture. The reaction mixture was re-heated to 30° C. The layers were separated, and the lower (aqueous) layer (approximately 1.2 L) was discarded. The upper (organic) layer was distilled at reduced pressure to remove approximately six volumes of solvent (approximately 1.2 L at less than 55° C.). The reaction mixture was then cooled to 20° C., and was analysed for water content (typically <0.1% w/w). To this was added triethylamine (245 mL), and the reaction mixture was cooled to −10° C. To this was added trimethylamine hydrochloride (28 g), followed by a solution of para-toluenesulfonyl chloride (292 g) dissolved in toluene (1.2 L), whilst maintaining the temperature at −10° C.±10° C. When the addition was complete the reaction mixture was warmed to 20° C. To this was added water (1.2 L), and the reaction mixture was heated to 75° C. At 75° C., the layers were separated, and the lower (aqueous) layer was discarded. To the retained organic layer was added 1 M hydrochloric acid (1.2 L), the reaction mixture was heated to 80° C. The layers were separated and the lower (aqueous) layer was discarded. The upper (organic) layer was cooled to 20° C. over approximately two hours. For convenience, the reaction mixture was held at 20° C. for approximately twelve hours. The reaction mixture was then cooled to 5° C. over approximately thirty minutes. The reaction mixture was held at 5° C. for approximately one hour. The mixture was filtered, and the crude solid was then washed with toluene (200 mL, 5° C.). The damp solid was dried in vacuo, at 35° C., for approximately twenty-four hours, to give the title compound as a white, crystalline solid (373 g, 76% yield).

$^1$H-NMR (CDCl$_3$, 300 MHz) δ 7.80 (d, J=8.4 Hz, 2H, CH$_{ar}$), 7.41-7.32 (m, 4H, CH$_{ars}$), 6.94 (d, J=8.2 Hz, 1H, CH$_{ar}$), 4.44-4.38 (m, 2H, CH$_2$), 4.34-4.28 (m, 2H, CH$_2$), 2.45 (s, 3H, ArCH$_3$).

Alternative 3

To 3-fluoro-4-hydroxybenzonitrile (5 g) was added xylene (10 mL), at 20° C. To the resulting mixture was added ethylene carbonate (3.44 g) and tetra-n-butylammonium iodide (0.71 g). The reaction mixture was heated to 125° C.±5° C., over twenty minutes, and maintained at this temperature for five hours. For convenience, the reaction mixture was cooled to 20° C., over approximately fifteen and an half hours, and was analysed for water content (typically <0.1% w/w). To the cooled reaction mixture was added triethylamine (7.1 mL) and 4-methylpentan-2-one (16 mL). The reaction mixture was then cooled to −10° C., over approximately twenty minutes, after which trimethylamine hydrochloride (0.70 g) was added, followed by a solution of para-toluenesulfonyl chloride (7.34 g), dissolved in 4-methylpenatan-2-one (40 mL). During the addition, the reaction temperature was maintained at −10° C.±5° C. When the addition was complete, the reaction mixture was warmed to 20° C. Water (30 mL) was added and the reaction mixture was heated to 72° C., at which temperature the layers were separated and the lower (aqueous) layer was discarded. To the retained (organic) layer was added 1 M hydrochloric acid (30 mL), and the reaction mixture was again heated to 72° C. The layers were separated and the lower (aqueous) layer was discarded. For convenience, the upper (organic) layer was cooled to 20° C. over eighteen hours. The reaction mixture was then cooled to 5° C. over approximately ten minutes, after which the crude product was isolated by filtration and washed (on the filter) with 4-methylpenatan-2-one (5 mL, at 5° C.). The damp solid was then dried in vacuo, at 35° C., for approximately twenty-four hours. This provided the title compound as a white crystalline solid (7.3 g; 60% yield).

$^1$H NMR (400 MHz, CDCl$_3$): δ 7.81 (d, J=8.3 Hz, 2H), 7.41-7.32 (m, 3H), 6.95 (t, J=8.2 Hz, 2H), 4.43-4.38 (m, 2H), 4.33-4.29 (m, 2H), 1.54 (s, 3H).

Alternative 4

To 3-fluoro-4-hydroxybenzonitrile (10 g) was added ethylene carbonate (6.85 g), potassium iodide (1.2 g) and xylene (21 mL), at 20° C. The reaction mixture was heated to 140° C.±5° C., over thirty minutes, and maintained at this temperature for twelve hours. For convenience, the reaction mixture was cooled to 20° C., over approximately eight hours. To the cooled reaction mixture was added triethylamine (7.1 mL) and 4-methyl-pentan-2-one (14.25 mL). The reaction mixture was then cooled to −10° C., over approximately five minutes, after which trimethylamine hydrochloride (1.4 g) was added, followed by a solution of para-toluenesulfonyl chloride (14.6 g), dissolved in 4-methylpenatan-2-one (80 mL). During the addition, the reaction temperature was maintained at −10° C.±5° C. When the addition was complete, the reaction mixture was warmed to 20° C. Water (60 mL) was added and the reaction mixture was heated to 75° C., at which temperature the layers were separated and the lower (aqueous) layer was discarded. To the retained (organic) layer was added 1 M hydrochloric acid (60 mL), and the reaction mixture was again heated to 75° C. The layers were separated and the lower (aqueous) layer was discarded. For convenience, the upper (organic) layer was cooled to 20° C. over approximately fourteen hours. The reaction mixture was then cooled to 5° C. over approximately ten minutes, after which the product was isolated by filtration and washed (on the filter) with 4-methylpenatan-2-one (10 mL, at 5° C.). The damp solid was then dried in vacuo, at 35° C., for approximately twenty-four hours. This provided the title compound as a white crystalline solid (16.9 g; 69% yield).

$^1$H-NMR (300 MHz, CDCl$_3$): δ 7.85-7.77 (m, 2H), 7.43-7.30 (m, 4H), 6.95 (t, J=8.3 Hz, 1H), 4.45-4.37 (m, 2H), 4.35-4.27 (m, 2H), 2.45 (s, 3H).

Preparation L 3-(tert-Butyloxycarbonylamino)propyl 2,4,6-trimethylbenzenesulfonate A solution of 3-aminopropan-1-ol (19.82 g, 264 mmol) in DCM (160 mL) was heated to 35° C.±3° C. To this a solution of di-tert-butyl dicarbonate (60.01 g, 267 mmol) in DCM (100 mL) was added over 60 minutes. The reaction mixture was maintained at 35° C.±3° C. during the addition. After the addition was complete, the reaction mixture was maintained at 35° C.±3° C. for four hours. The reaction mixture was then cooled to 22° C.±2° C., and left stirring overnight. Triethylamine (56 mL, 402 mmol) was added in one portion. The reaction mixture was then cooled to −10° C.±3° C. Trimethylamine hydrochloride (12.79 g, 134 mmol) was added in one portion. The resulting mixture was cooled further to −15° C.±3° C. The reaction mixture was held at this temperature for a further five minutes. To this, a solution of 2-mesitylenesulfonyl chloride (59.50 g, 272 mmol) in DCM (260 mL), was added slowly enough to maintain the temperature at less than −10° C., (45 minutes). After the addition was complete, the reaction mixture was maintained at −10° C.±3° C. for an additional 15 minutes. The reaction was monitored by high pressure liquid chromatography (HPLC). The reaction mixture was warmed to greater than 0° C. Water (100 mL) was added and the resulting bi-phasic mixture was stirred rapidly for five minutes. Further water (300 mL) was added, and the phases were separated. The organic layer was then concentrated under reduced pressure and solvent (410 mL) was removed whilst keeping the temperature at less than 40° C. Propan-2-ol (480 mL) was added. The resulting solution was further concentrated under reduced pressure and solvent (195 mL) was removed whilst keeping the temperature at less than 40° C. The resultant solution was cooled to 20° C.±3° C., and water (180 mL) was added slowly via syringe pump over 30 minutes±5 minutes, whilst maintaining the temperature at 20° C.±3° C. This caused the crystallisation of the title compound. The mixture was cooled to 10° C.±3° C., over ten minutes. The product was collected by filtration. This was then washed by displacement with 1:1 v/v propan-2-ol: water (80 mL). The product was then dried in vacuo, at 35° C., for 16 hours. This gave the title compound as a white solid (64.30 g, 179.97 mmol, 68%).

$^1$H NMR (300 MHz, CDCl$_3$) δ 6.98 (2H, d, J=0.4 Hz), 4.65 (1H, s), 4.02 (2H, t, J=6.2 Hz), 3.19 (2H, q, J=6.4 Hz), 2.63 (6H, s), 2.32 (3H, s), 1.86 (2H, quintet, J=6.3 Hz), 1.42 (9H, s).

$^1$H NMR (300 MHz, DMSO-d$_6$) δ 7.13 (2H, s), 6.81 (1H, t, J=5.1 Hz), 3.92 (2H, t, J=6.5 Hz), 2.93 (2H, q, J=6.4 Hz), 2.50 (6H, quintet, J=1.8 Hz), 2.29 (3H, s), 1.70 (2H, quintet, J=6.7 Hz), 1.36 (9H, d, J=8.5 Hz).

Preparation M 3-(tert-Butyloxycarbonylamino)propyl 4-chlorobenzenesulfonate

3-Amino-1-propanol (10 mL, 9.81 g, 130.62 mmol) was dissolved in DCM (78 mL). The resulting mixture was heated to 35° C. and a solution of di-tert-butyl dicarbonate (29.42 g, 130.76 mmol) in DCM (49 mL) was then added over 45 minutes whilst maintaining the temperature at 35° C.±3° C. Once addition was complete, the reaction mixture was stirred at 35° C.±30° C. for a further two hours.

The reaction was analysed by TLC (3:1 ethyl acetate: isohexane, potassium permanganate stain). The reaction mixture was cooled to 22° C., and triethylamine (27 mL, 193.71 mmol) was added. After further cooling of the reaction mixture to −10° C., trimethylamine hydrochloride (6.45 g, 66.14 mmol) was added and the temperature reduced to −15° C. Stirring was continued at −15° C. for 5 minutes. A solution of 4-chlorobenzenesulfonyl chloride (27.55 g, 130.53 mmol) in DCM (127 mL) was then added over 45 minutes maintaining the temperature at less than −10° C. Once addition was complete, the reaction was stirred at −10° C. for a further 5 minutes before being warmed to 5° C. over 30 minutes. Water (196 mL) was added and the resulting biphasic mixture stirred rapidly for 5 minutes. The phases were then separated and the upper (aqueous) layer discarded. Solvent (186 mL) was removed by distillation under vacuum, keeping the temperature below 40° C. Propan-2-ol (235 mL) was then added. Further solvent (81 mL) was removed by distillation under vacuum (keeping the temperature below 40° C.), after which the mixture was cooled to 20° C. and water (88 mL) added over 60 minutes to crystallise the product from solution. The product was collected by filtration, washed with 1:1 v/v propan-2-ol: water (100 mL), suction dried as far as possible on the filter, then dried in vacuo (35° C., 16 h) to give the title compound as a white solid (14.42 g, 41.22 mmol, 32%).

$^1$H NMR (300 MHz, CDCl$_3$) δ 7.85 (dt, J=8.9, 2.2 Hz, 2H), 7.54 (dt, J=9.0, 2.3 Hz, 2H), 4.61 (s, 1H), 4.13 (t, J=6.2 Hz, 2H), 3.18 (q, J=6.4 Hz, 2H), 1.87 (quintet, J=6.3 Hz, 2H), 1.42 (s, 9H).

$^{13}$C NMR (100 MHz, CDCl$_3$) δ 155.93 (C=O), 140.56 (aromatic C—H), 134.41 (aromatic C—H), 129.46 (d, J=37.4 Hz, ipso-C), 127.64 (ipso-C), 68.42 (CH$_2$—O), 36.81 (CH$_2$—N), 29.35 (—CH$_2$CH$_2$CH$_2$—), 28.32 (C—CH$_3$).

Preparation N 3-(4-Cyanophenoxypropyl) 4-methylbenzenesulfonate

Alternative 1

(i) 4-(3-Hydroxypropoxy)benzonitrile

To a flask was added 4-hydroxybenzonitrile (50 g, 0.41 mol, 1 eq.) and potassium carbonate (0.51 mol, 1.25 eq.). To this mixture was added 4-methyl-2-pentanone (400 mL). Stirring was started and 3-bromo-1-propanol (61.50 g, 0.4 mol, 1.05 eq.) was added in one portion. The reaction mixture was heated to between 85 and 90° C. for 5 hours. Water (250 mL) was then added and the resultant mixture heated to 30° C. until all solids had gone into solution. The aqueous layer was separated from the organic layer. The organic layer was diluted with 4-methyl-2-pentanone (400 mL) to provide a solution of the sub-title compound that was employed directly in the next step without further purification.

GC: 95% pure, LC: 96.50%

GC-MS: m/z=177.

$^1$H NMR (300 MHz, CDCl$_3$) δ 1.50 (t, J=5.7 Hz, 1H), 2.07 (quintet, J=6.0 Hz, 2H), 3.87 (q, J=5.7 Hz, 2H), 4.17 (t, J=6.0 Hz, 2H), 6.96 (dd, J=6.9, 2.1 Hz, 2H), 7.59 (dd, J=6.9, 2.1 Hz, 2H).

(ii) 3-(4-Cyanophenoxypropyl) 4-methylbenzenesulfonate

The solution generated in step (i) above was distilled under reduced pressure (distillate temperature 50° C. and pressure 100 mbar). About 500 mL of the solvent was distilled off. The water content of the residue was about 0.002% w/w. The residue was diluted with 4-methyl-2-pentanone (400 mL) and triethylamine (53.70 g, 0.53 mol, 1.25 eq.) added. The reaction mixture was cooled to −15° C. and trimethylamine hydrochloride (8.16 g, 0.083 mol, 0.2 eq.) added. To the stirring solution was added p-toluenesulfonyl chloride (85.80 g, 0.445 mol, 1 eq.) in 4-methyl-2-pentanone (400 mL), whilst keeping the temperature below −10° C. The reaction mixture was stirred at below −10° C. for 3 hours before being allowed to warm slowly to room temperature, at which temperature stirring was continued for a further 18 hours. Water (300 mL) was added to the reaction mixture and the resulting slurry was heated (ca. 85° C.) until all the solids had gone into solution. The aqueous layer was separated from the organic layer. To the organic layer was added hydrochloric acid (200 mL, 1 M). The resulting mixture was then heated (ca. 85° C.) until all the solids were in solution. The aqueous layer was separated from the organic layer. The organic layer was allowed to come to room temperature and was then cooled (5° C.) for 2 hours. The precipitated solid was isolated by filtration and washed with 4-methyl-2-pentanone (100 mL) before being dried in an oven at 50° C. under reduced pressure. This yielded the title compound as a colourless solid (114.25 g, 82%).

$^1$H-NMR (300 MHz, CDCl$_3$,) δ 2.11-2.19 (2H, m), 3.99-4.04 (2H, t), 4.22-4.26 (2H, t), 6.81-6.84 (2H, m), 7.25-7.26 (2H, m), 7.54-7.58 (2H, m), 7.74-7.77 (2H, m).

LC 98.7%.

(M+H+acetonitrile)$^+$=373.

Alternative 2

(i) 4-(3-Hydroxypropoxy)benzonitrile

To a flask was added 4-hydroxybenzonitrile (50 g, 0.41 mol, 1 eq.) and toluene (400 mL). The resulting mixture was heated to 65° C.±5° C. To the stirring reaction mixture was added 3-bromo-1-propanol (72.90 g, 0.51 mol, 1.25 eq.) and then, over the course of 20 minutes, sodium hydroxide (210 mL, 2.5 M, 0.52 mol, 1.25 eq.). The reaction was heated to 65 to 70° C. for 17 hours. The aqueous layer was separated from the organic layer at 60 to 65° C. The organic layer was then employed directly in the next step without further purification. LC purity 95.3%.

$^1$H NMR (300 MHz, CDCl$_3$) δ 1.50 (t, J=5.7 Hz, 1H), 2.07 (quintet, J=6.0 Hz, 2H), 3.87 (q, J=5.7 Hz, 2H), 4.17 (t, J=6.0 Hz, 2H), 6.96 (dd, J=6.9, 2.1 Hz, 2H), 7.59 (dd, J=6.9, 2.1 Hz, 2H).

(ii) 3-(4-Cyanophenoxypropyl) 4-methylbenzenesulfonate

Toluene (400 mL) was added to the solution generated in the previous step. About 330 mL of the solvent was distilled off under reduced pressure (at 50° C.). To the residue was added toluene (200 mL) and triethylamine (53.70 g, 0.53 mol, 1.25 eq.). The reaction mixture was cooled to −15° C. and trimethylamine hydrochloride (8.16 g, 0.083 mol, 0.2 eq.) added. To the stirring solution was added p-toluenesulfonyl chloride (85.80 g, 0.445 mol, 1 eq.) in toluene (300 mL), whilst keeping the temperature below −10° C. The residual p-toluenesulfonyl chloride was washed into the reaction mixture with toluene (100 mL). The reaction mixture was stirred at below −10° C. for 3 hours. The reaction mixture was allowed to warm to room temperature slowly and was then stirred for 18 hours. To the reaction mixture added water (300 mL) and resulting the slurry was heated (ca. 85° C.) until all the solids were in solution. The aqueous layer was separated from the organic layer. To the organic layer was added hydrochloric acid (200 mL, 1 M). The organic layer was allowed to cool to room temperature, and then to ca. 5° C., at which temperature it was stirred for 2 hours. The precipitated solid was isolated by filtration and then washed with toluene (100 mL). The product was dried in an oven (at 50° C.) under reduced pressure to yield the title compound as a colourless solid (94.20 g, 67%).

LC purity 99.1%
(M+H+acetonitrile)$^+$=373.
$^1$H NMR (300 MHz, CDCl$_3$) δ 2.15 (quintet, J=5.9 Hz, 2H), 2.43 (s, 3H), 4.01 (t, J=5.9 Hz, 2H), 4.24 (t, J=5.9 Hz, 2H), 6.83 (dd, J=6.9, 1.9 Hz, 2H), 7.26 (t, J=3.9 Hz, 6H), 7.56 (t, J=16.2 Hz, 2H), 7.75 (d, J=8.2 Hz, 2H).

Alternative 3

(i) 4-(3-Hydroxypropoxy)benzonitrile

To a flask was added 4-hydroxybenzonitrile (10 g, 82.7 mmol, 1 eq.) and potassium carbonate (13.60 g, 98.7 mmol, 1.25 eq.). To this mixture was added acetonitrile (80 mL) and then, under stirring, 3-bromo-1-propanol (12.25 g, 86.40 mmol, 1.05 eq.). The reaction mixture was heated at reflux (84° C.) for 5 hours before being allowed to cool to room temperature. Toluene (80 mL) and water (50 mL) were added and the resulting mixture was heated (≈30° C.) until all of the solids had gone into solution. The aqueous layer was separated from the organic layer. The organic layer was retained.

$^1$H-NMR (300 MHz, CDCl$_3$) δ 1.50 (t, J=5.7 Hz, 1H), 2.07 (quintet, J=6.0 Hz, 2H), 3.87 (q, J=5.7 Hz, 2H), 4.17 (t, J=6.0 Hz, 2H), 6.96 (dd, J=6.9, 2.1 Hz, 2H), 7.59 (dd, J=6.9, 2.1 Hz, 2H).

(ii) 3-(4-Cyanophenoxypropyl) 4-methylbenzenesulfonate

The solution generated in step (i) above was distilled to remove 40 mL of the solvent. The mixture was then allowed to cool to room temperature before triethylamine (10.09 g, 98.7 mmol, 1.25 eq.) was added. The reaction mixture was cooled to −15° C. and trimethylamine hydrochloride (1.57 g, 16.45 mmol, 0.2 eq.) was added. To the stirring reaction mixture was added p-toluenesulfonyl chloride (16.47 g, 86.38 mmol, 1.05 eq.) in toluene (60 mL), whilst keeping the temperature below −10° C. The reaction mixture was stirred at below −10° C. for 3 hours before being allowed to warm to room temperature. Water (60 mL) was added and the resulting slurry was heated to ca. 60° C. until all the solids had gone into solution. The aqueous layer was separated from the organic layer and hydrochloric acid (60 mL, 0.5 M) was added to the organic layer. The resulting mixture was heated to ca. 62° C. until all the solids were in solution. The organic layer was separated from the aqueous layer, was allowed to cool to room temperature and was then stirred at ca. 5° C. for 2 hours. The precipitated solid was isolated by filtration and washed with toluene (20 mL). The product was dried in an oven (at 40° C.) under reduced pressure to yield the title compound as a colourless solid (19.92 g, 73%).

$^1$H-NMR (300 MHz, CDCl$_3$.) δ 2.11-2.19 (2H, m), 3.99-4.04 (2H, t), 4.22-4.26 (2H, t), 6.81-6.84 (2H, m), 7.25-7.26 (2H, m), 7.54-7.58 (2H, m), 7.74-7.77 (2H, m).

LC 99.6%.
(M+H+acetonitrile)$^+$=373.

Preparation O

3-Benzyl-9-oxa-3,7-diazabicyclo[3.3.1]nonane dihydrochloride (i) Chirally enriched N,N-Bis(2(R)-oxiranylmethyl)benzenesulfonamide Alternative 1

Benzenesulfonamide (120 g, 0.763 moles), (R)-epichlorohydrin (282.6 g, 3.054 moles) and water (960 g) were added to a 2 L reaction flask. The mixture was heated to 40° C. and then sufficient sodium hydroxide solution (31%) was added over approximately 5 mins such that the pH was raised to 11.5-12.0 (in an alternative procedure, 25% sodium hydroxide solution can be employed). The remainder of the sodium hydroxide (201 g, 1.557 moles in total) was then added at such a rate as to maintain the pH at 11.5-12.0 and the temperature at 40-50° C. (usually requires addition over 3-4 hours). The reaction mixture was then stirred for 2 hours at 40-45° C. and distilled to remove 3 volumes (360 mL) of water/epichlorohydrin at 50 mbar (5 kPa) with a maximum contents (source vessel) temperature of 43° C. Chlorobenzene was then added (221.4 g, 1.67 volumes) and the mixture was stirred for 0.5 hours before being allowed to settle. The lower product (chlorobenzene) layer was separated and the extraction process repeated using a further portion of chlorobenzene (44.3 g, 0.33 vols.). The two product layers were combined for use in the next step (see step (ii), Alternative 1 below).

Alternative 2

Benzenesulfonamide (175 kg, 1 eq.), water (1365 kg, 8 rel. vol.) and (R)-epichlorohydrin (412 kg, 4 eq.) were charged to a reaction vessel. The reactants were heated to 40° C. Sufficient aqueous sodium hydroxide was added, over the course of approximately 20 minutes, to adjust the pH to 11.5-12.0. The remainder was then charged in a controlled manner over approximately 150 minutes, such that the temperature of the reaction was maintained between 40° C. and 50° C., and the pH remained in the range 11.5 to 12.0 (total charge: 90.8 kg in 202 kg of water). After the addition of sodium hydroxide was complete, the reaction was stirred between 40° C. and 45° C.

for 2 hours. The excess (R)-epichlorohydrin was removed as a water azeotrope by vacuum distillation (ca. 60 mbar (6 kPa), internal temperature 43° C. maximum, 525 liters of distillate, 3 rel. vol.). Chlorobenzene (total of 387 kg, 2 rel. vol.) was then charged to the reaction in two portions. Following each addition, the mixture was stirred and then allowed to settle before the chlorobenzene layer was separated. The two chlorobenzene layers were then combined and used without further treatment in the next step (see step (ii), Alternative 2 below).

(ii) Chirally enriched 5-Benzyl-3(S),7(S)-dihydroxy-1-phenylsulfonyl-1,5-diazacyclooctane Alternative 1

Methanol (854 g, 18 volumes) was heated to reflux. Chirally enriched N,N-bis(2(R)-oxiranylmethyl)benzenesulfonamide (0.382 mol; see step (i), Alternative 1 above) and benzylamine (37.3 g, 0.347 moles) were concurrently added via syringe pumps over 6 hours into the reaction vessel at opposite sides of the reaction vessel. The reaction was maintained at reflux throughout the addition of the reagents. After addition was complete, the reaction solution was maintained at reflux for a further 3 hours before methanol (14 volumes, 840 mL) was distilled from the reaction vessel at atmospheric pressure. Chlorobenzene (266 g, 240 mL) was then added and the distillation continued until a further portion of methanol (4 volumes, 240 mL) had been collected from the reaction vessel. A second portion of chlorobenzene (133 g, 120 mL) was added and a mixture of solvent (4 volumes, 240 mL of a mixture of chlorobenzene/methanol) was distilled from the reaction mixture at 50 mbar (5 kPa). The remaining mixture (after the distillation) comprised the sub-title compound and chlorobenzene with a methanol content of <0.1% w/w. This solution was employed in the next step (see step (iii), Alternative 1 below).

Alternative 2

Methanol (2494 kg, 18 rel. vol.—either fresh or recycled) was charged to a reaction vessel and heated to reflux temperature (approx. 65° C.). Simultaneously, and over approximately 6 hours were charged the chlorobenzene solution (containing chirally enriched N,N-bis(2(R)-oxiranylmethyl)benzenesulfonamide) from step (i), Alternative 2 above and benzylamine (109 kg, 0.91 eq.). The batch was maintained at reflux throughout the addition. The reaction was stirred at approximately 65° C. (reflux temperature) for a further 3 hours. Methanol (1938 kg, 14 rel. vol.) was then removed by distillation at atmospheric pressure before chlorobenzene (775 kg, 4 rel. vol.) was added. The resulting solution was used without further treatment in the next step (see step (iii), Alternative 2 below).

(iii) 3-Benzyl-7-(phenylsulfonyl)-9-oxa-3,7-diazabicyclo[3.3.1]nonane

Alternative 1

Chlorobenzene (598 g, 9 volumes) and water (7.2 g, 0.4 moles) were added to a solution of chirally enriched 5-benzyl-3(S),7(S)-dihydroxy-1-phenylsulfonyl-1,5-diazacyclooctane in chlorobenzene (0.382 moles; see step (ii), Alternative 1 above) and heated to 75° C. Sulfric acid (98%, 134 g, 1.337 moles) was then added over 1 hour, whilst maintaining the temperature in the range 75-90° C. (In an alternative embodiment, chirally enriched 5-benzyl-3(S),7(S)-dihydroxy-1-phenylsulfonyl-1,5-diazacyclooctane may be added to sulfuric acid.) The biphasic reaction mixture was heated to 95° C. and stirred for 3 hours. The temperature was adjusted to 50° C. and methanol (57 g, 1.2 volumes) was added at such a rate as to maintain the temperature at between 50 and 60° C. The reaction mixture was basified by adding aqueous ammonia (17.5%, 346 g, 372 mL) over 2 hours at between 60 and 70° C., and then allowed to settle after 15 min of stirring (the mixture is kept at 60° C. during the period in which it is allowed to settle). The lower aqueous layer was separated and the upper organic layer transferred to the crystallising vessel. The aqueous layer was returned to the reaction vessel and the temperature was adjusted to 45° C. before chlorobenzene (133 g, 120 mL) was added. The separation process was repeated (i.e. the aqueous layer extracted and the phases separated) and the second organic phase combined with the first organic phase in the crystallising vessel. Chlorobenzene was then distilled (660 mL, 11 volumes) from the product layer at 50 mbar (5 kPa) and then methanol (470 g, 594 mL) was added over the course of 1 hour. The temperature was allowed to fall during this addition, after which the resulting slurry was cooled to 5° C. and held at that temperature for 1 hour before being filtered. The filter cake was then washed with two portions of methanol (2×47.4 g, (2×60 mL)), at either 5° C. or ambient temperature, and then suction dried for 30 mins. The product was transferred to a vacuum oven and dried to constant weight at 40° C. to provide the sub-title compound (yield 31% (42.5 g) over Alternative 1 of steps (i), (ii) and (iii)).

Alternative 2

The chlorobenzene/methanol solution from step (ii), Alternative 2 above was distilled further at atmospheric pressure (removing a total of 700 liters (4 rel. vol.) of solvent). Fresh and/or recycled chlorobenzene (350 liters, 2 vols.) was charged, then distillation was continued under vacuum (ca. 50 mbar (5 kPa)) to complete solvent exchange to chlorobenzene (a total of a further 700 liters (4 rel. vol.) being removed through distillation). Further chlorobenzene (fresh or recovered, 1575 liters, 9 rel. vol.) and water (21 kg, 1.05 eq.) were charged and the batch heated to 75° C. (In an alternative embodiment, the chlorobenzene/water mixture may be added to sulfuric acid.) Sulfuric acid (382 kg, 3.5 eq. of 98%) was charged over approximately 1 hour, whilst allowing the temperature to rise up to 90° C. The biphasic reaction mixture was maintained for a further 3 hours at 95° C. After cooling to 50-55° C., methanol (160 kg, 1.2 rel. vol.) was charged, whilst maintaining the temperature at 50-55° C. Aqueous ammonia (176 kg in 830 kg of water) was charged in a controlled manner whilst maintaining the contents at between 60-70° C. After stirring for 15 minutes, the batch was settled for 30 minutes and the layers separated. After back extracting the aqueous layer with chlorobenzene (388 kg, 2 vol.) the organic layers were combined and a total of 1925 liters (11 rel. vol.) of chlorobenzene were distilled under vacuum (50 mbar (5 kPa), 45° C.). Methanol (1330 kg, 9.6 rel. vol) was charged to the residue. The resultant slurry was cooled to 5° C., stirred for 1 hour, then the solids were isolated by filtration. The wet filter cake was dried under vacuum (~50 mbar (5 kPa), 40° C. maximum temperature) to afford 130.5 kg of the sub-title compound (32.7% yield over Alternative 2 of steps (i), (ii) and (iii)).

(iv) 3-Benzyl-9-oxa-3,7-diazabicyclo[3.3.1]nonane dihydrochloride

Alternative 1

3-Benzyl-7-(phenylsulfonyl)-9-oxa-3,7-diazabicyclo[3.3.1]nonane (40 g, 0.112 mol; see step (iii), Alternative 1 above) and hydrobromic acid (48%, 179 g, 120 mL) were heated to 122° C. and stirred for 9 hours. The solution was cooled to 20° C. before toluene (173 g, 200 mL) was added and the resulting biphasic mixture stirred for 30 mins. After being allowed to settle, the lower aqueous layer of the biphasic mixture was separated and the upper toluene layer discarded. The aqueous layer was returned to the reaction vessel and sodium hydroxide (31%, 181 g, 141 mL) was added over 45 mins, allowing the temperature to rise to a maximum of 60° C. Toluene (156 g, 180 mL) was added and the temperature adjusted to 60° C. before the layers were separated and the lower aqueous layer discarded. The toluene layer, containing the product, was washed with water (120 g) at 60° C. before being cooled to 40° C., after which iso-propanol (345 g, 440 mL) was added. Hydrochloric acid (36%, 25.9 g, 0.256 mol) was then added over 1 hour at 40-45° C., after which the mixture was cooled to 5° C. and stirred for 1 hour. The product was filtered, washed with iso-propanol (141 g, 180 mL) and then suction dried for 30 mins before being transferred to the vacuum oven and dried to constant weight at 40° C. (yield: 88%, 28.6 g).

Alternative 2

3-Benzyl-7-(phenylsulfonyl)-9-oxa-3,7-diazabicyclo[3.3.1]nonane (107 kg, 1 eq.; see step (iii), Alternative 2 above) and hydrobromic acid (229 kg, 9.5 eq. in 248 kg water) were charged to a vessel, heated initially to 110 to 115° C. with the scrubber vent open, the vent was sealed then heating was continued under a slight positive pressure (4 psi (0.27 atmospheres)) to 122° C. then stirred for 9 hours at 122° C. After cooling to 15-20° C., toluene (463 kg, 5 rel. vol) was charged and the resulting biphasic mixture was stirred before being allowed to settle for 30 minutes. The layers were separated and the lower aqueous layer was returned to the original vessel. To this vessel was then charged aqueous sodium hydroxide (149 kg, 12.5 eq. in 332 kg water) whilst maintaining the contents temperature below 80° C. The reaction mixture was cooled to a temperature in the range of 15 to 20° C. before toluene (416 kg, 4.5 rel. vol) was charged. The resulting biphasic mixture was heated to 60° C. and then stirred and settled for 30 minutes at 60° C. After separation, the toluene layer was washed with water (214 kg, 2 rel. vol.) at 60° C., then cooled to 15-20° C. Isopropyl alcohol (925 kg, 11 rel. vols.) was charged, and the contents adjusted to 40° C. Hydrochloric acid (25 kg, 2.3 eq. in 44.5 kg water) was charged in a controlled manner, keeping the contents in the range 40-45° C. After stirring for 1 hour at 40° C., the resultant slurry was cooled to 5° C. and stirring continued for a further 2 hours. The solids were isolated by filtration and dried (40° C. maximum temperature) to afford 78 kg (89.7%) of the title compound.

Alternative 3

Water (72 mL) and concentrated sulfuric acid (228 mL) were added to 3-benzyl-7-(phenylsulfonyl)-9-oxa-3,7-diazabicyclo[3.3.1]nonane (100.06 g, 279 mmol; see step (iii) above). (In an alternative embodiment, 3-benzyl-7-(phenylsulfonyl)-9-oxa-3,7-diazabicyclo[3.3.1]nonane may be added to sulfuric acid.) The reaction mixture was heated for 9 hours at 130° C., then left to cool to room temperature overnight. The acidic solution was poured into a clean vessel containing water (300 mL), and concentrated aqueous ammonia (35%) added dropwise over 2 hours (550 mL). After ammonia addition was complete, the pH of the reaction mixture was checked and found to be 10. Toluene (450 mL) was then added, and the temperature adjusted to 60° C. The lower (aqueous) layer was separated and discarded. To the remaining upper layers (organic layer and interfacial layer), 5 M sodium hydroxide solution (300 mL) was added. The mixture was re-heated to 60° C., and stirred for 15 minutes. The layers were separated and the lower aqueous phase removed. Isopropanol (1100 mL) was added to the organic phase and the resulting solution warmed to 43° C. Concentrated hydrochloric acid (54 mL) was then added over 1 hour, maintaining the temperature at between 40 and 45° C., which precipitated the product. The mixture was then cooled to 5° C., and stirred for 1 hour. The product was collected by filtration and the filter cake was washed by displacement with isopropanol (400 mL) before being dried as much as possible by suction (on the filter) and then in vacuo (for 64 hours at 40° C.). This gave the title compound as a crystalline, white solid (77.16 g, 95%).

Alternative 4

Water (11.2 mL) and concentrated sulfuric acid (24.5 mL) were added to 5-benzyl-3,7-dihydroxy-1-phenylsulfonyl-1,5-diazacyclooctane (2.92 g, 7.76 mmol; see step (ii) above). The reaction mixture was heated for 24 hours at 95° C. The temperature was adjusted to 60° C., and toluene (40 mL) was added. Sodium hydroxide solution was then added (150 mL of 5 M), causing the internal temperature to rise to 85° C. The pH of the reaction mixture was then checked, and was found to be 2. A few pellets of solid sodium hydroxide were then added. The pH was measured again, and was found to be 13. The layers were separated, and the aqueous phase extracted with toluene (50 mL). The organic phases were combined, dried (MgSO$_4$), filtered and concentrated in vacuo to provide 3-benzyl-9-oxa-3,7-diazabicyclo[3.3.1]nonane as an orange-brown oil. This can be converted to the title compound (dihydrochloride salt) by reaction with hydrochloric acid under standard conditions.

$^1$H NMR (300 MHz, DMSO-d$_6$) δ 7.25 (m, 5H), 4.38 (s, 1H), 3.69 (s, 1H), 3.49 (m, 2H), 3.34 (m, 2H), 2.99 (d, J=13.8 Hz, 1H), 2.86 (m, 2H), 2.74 (m, 1H), 2.64 (m, 2H).

Alternative 5

77% sulfuric acid (126.3 g, 0.99 moles) and 98% sulfuric acid (68.4 g, 0.683 moles) are mixed carefully to afford 195 g of 85% sulfuric acid (1.675 moles, 15 eq.). (Alternatively, water and 98% sulfuric acid are mixed carefully to prepare the same quantity of 85% sulfuric acid.) The reaction mixture is heated to 100° C., before 3-benzyl-7-(phenylsulfonyl)-9-oxa-3,7-diazabicyclo-[3.3.1]nonane (40 g, 0.112 moles; see step (iii) above) is added, portion-wise, over the course of approximately 45 to 60 minutes. The reaction mixture is heated to 130° C., and stirred at this temperature for 9 hours. After the reaction mixture is cooled to 20 to 25° C., water (120 g) is added over the course of approximately 30 minutes, during which addition the reaction mixture is maintained at 20 to 50° C. At this point, 35% ammonia solution (193.6 g, 3.96 moles) is added over the course of approximately 2 hours, during which addition the reaction mixture is maintained at below 70° C. After verifying that the pH of the batch is 10 or above, toluene is added and the reaction mixture is stirred rapidly, at 70 to 75° C., for 15 minutes. The layers are allowed to settle for approximately 30 minutes, then the lower (aqueous) layer is discarded. To the remaining upper layers (organic layer and interfacial layer), is added 5 M sodium hydroxide solution (139 g, 0.60 moles), and the reaction mixture is stirred for approximately 15 minutes at 60 to 65° C. After settling for 30 minutes, the layers are separated, keeping any interfacial material with the aqueous layer. The product (toluene) layer is cooled to 40 to 45° C. before isopropanol (345 g, 440 mL) is added, followed by, over the course of 1 hour and at 40 to 45° C., 36% hydrochloric acid (26.0 g, 0.257 mols). The resulting mixture is cooled to 5° C. and stirred at this temperature for 1 hour. The product is isolated by filtration, washed with isopropanol (126 g, 160 mL) and then dried by suction (on the filter) for 30 mins, before being transferred to a vacuum oven. The title compound is then dried to constant weight at 40° C. (30.1 g, 92.5%).

Preparation P

[2-(7-Benzyl-9-oxa-3,7-diazabicyclo[3.3.1]non-3-yl)ethyl]carbamic acid tert-butyl ester, 2,4,6-trimethyl-benzenesulfonic acid salt monohydrate Alternative 1

Solid 3-benzyl-9-oxa-3,7-diazabicyclo[3.3.1]nonane dihydrochloride (200.2 g, 1.0 eq.; see Preparation O above), aqueous sodium hydroxide (2.5 M, 900 mL, 4.5 rel. vol.) and solid 2-(tert-butyloxycarbonylamino)ethyl 2,4,6-trimethyl-benzene-sulfonate (248.4 g, 1.05 eq.; see Preparation S below) were charged to a reaction vessel. Stirring was started, toluene (500 mL, 2.5 rel. vol.) was charged and the reaction heated from 27° C. to 65° C. over 20 minutes. The reaction was held at 65° C.±5° C. for 12 hours and then stirred at ambient temperature for 8 hours and left to stand for 24 hours. The mixture was reheated to 65° C. and the stirring stopped. The lower aqueous layer (first aqueous phase) was separated and added to a mixture of water (900 mL, 4.5 rel. vol.) and isopropanol (400 mL, 2 rel. vol.) thereby producing diluted first aqueous phase.

The temperature of the upper toluene layer (first organic phase) that was left in the original reaction vessel was noted to be 60° C. A cold (20° C.) solution of aqueous citric acid (10% w/v, 1000 mL, 5 rel. vol.) was then added to this toluene phase. The resulting mixture had a temperature of 38° C. This mixture was stirred for 5 minutes and then the stirring stopped to give an upper organic phase and a lower aqueous phase (second aqueous phase). These phases were separated and the organic phase only was discarded. The diluted first aqueous phase was heated to 75° C. The second aqueous phase was then added at such a rate that the temperature remained above 70° C. (this took 22 minutes). The mixture was stirred at 75° C. for 1 hour, then allowed to cool to 41° C. over 4 hours. The mixture was then stirred for 65 hours. The mixture, now at 23° C., was filtered. The filter cake was washed by displacement with water (800 mL, 4 rel. vol., water temperature was 22° C.) and then cold isopropanol (800 mL, 4 rel. vol., IPA temperature was 5° C.). The cake was sucked dry on the filter for 40 minutes, then the solid transferred to a vacuum oven. The solid was dried to constant weight in vacuo at 50° C. for 20 hours. This gave the title compound as a white solid (346.3 g, 90%).

Water by KF analysis=3.4% (monohydrate requires 3.1%)

$^1$H-NMR (400 MHz, CDCl$_3$) δ 1.44 (9H, s), 2.23 (3H, s), 2.73 (6H, s), 2.74-2.90 (5H, m), 2.95-3.0 (4H, m), 3.4-3.45 (2H, m), 3.65-3.70 (4H, m), 4.19 (2H, s), 4.30 (2H, s), 6.84 (2H, s), 6.95 (1H, bs), 7.40 (5H, s).

$^1$H-NMR (400 MHz, DMSO-d$_6$) δ 1.43 (9H, s), 2.17 (3H, s), 2.75 (2H, t), 2.90-2.94 (4H, m), 3.14-3.22 (4H, m), 3.22-3.4 (6H, m), 3.89 (2H, s), 4.13 (2H, s), 6.74 (2H, s), 7.12 (1H, bs), 7.42-7.46 (5H, m).

Alternative 2

Solid 3-benzyl-9-oxa-3,7-diazabicyclo[3.3.1]nonane dihydrochloride (100.1 g, 1.0 eq.; see Preparation O above), was added to aqueous sodium hydroxide (44 g of solid NaOH dissolved in 394 g of water) that was in a reaction vessel. At 25° C., solid 2-(tert-butyloxycarbonylamino)ethyl 2,4,6-trimethylbenzenesulfonate (124.0 g, 1.05 eq; see Preparation S below) was charged to the reaction vessel. Stirring was started, toluene (100 g, 1.0 rel wt) was charged and the reaction heated from 25° C. to 65° C.±3° C. over 10 minutes. The reaction was held at 65° C.±3° C. for 7 hours. Stirring was stopped and the lower aqueous layer (first aqueous phase) was separated at 60-65° C. (a small amount of interfacial material was kept with the organic phase), and added to a mixture of water (450 g, 4.5 rel wt) and isopropanol (150 g, 1.5 rel wt.), thereby producing a diluted, first aqueous phase. The temperature of the upper toluene layer that was left in the original reaction vessel (first organic phase) was noted to be 60° C. A cold (20° C.) solution of aqueous citric acid (10% w/w, 500 g, 5 rel wt.) was added to the toluene phase. The resulting mixture had a temperature of 40° C. This mixture was stirred for 5 minutes and then the stirring stopped to give an upper organic phase and a lower aqueous phase (second aqueous phase). These phases were separated and the organic phase only was discarded.

The diluted, first aqueous phase was heated to 75° C. The second aqueous phase was then added to the warmed, diluted, first aqueous phase such that the temperature was maintained in the range of 75° C.±5° C. (this took 54 minutes). The mixture was stirred at 75° C.±5° C. for 1 hour 18 minutes, before being allowed to cool naturally from 72° C. to 68° C. over 13 minutes (a lot of precipitate formed in this time). The slurry was then allowed to cool naturally from 68° C. to 40° C. over 2 hours, after which it was cooled in an ice/water bath from 40° C. to 5° C. over 47 minutes and then stirred at 5° C. for 1 hour. The mixture was filtered and the filter cake washed by displacement with cold (5° C.) water (400 g, 4.0 rel vol), then cold (5° C.) isopropanol (300 g, 3.0 rel wt). The filter cake was dried by suction on the filter for 37 minutes, before being transferred to a dish and left to air dry overnight. The resulting solid (195 g) was then dried to constant weight in vacuo at 50° C. for 6 hours 30 minutes. This gave the title compound as a white solid (176.50 g, 91%).

Water by KF analysis=3.26% (monohydrate requires 3.1%)

Alternative 3

Solid 3-benzyl-9-oxa-3,7-diazabicyclo[3.3.1]nonane dihydrochloride (100 g, 1.0 eq; see Preparation O above), aqueous sodium hydroxide (2.5 M, 450 mL, 4.5 rel vol) and solid 2-(tert-butyloxycarbonylamino)ethyl 2,4,6-trimethyl-benzenesulfonate (117.86 g, 1.0 eq.; see Preparation S below) were charged to a reaction vessel. Stirring was started and the reaction heated to 65° C.±5° C. for 6 hours. At this point, isopropanol (200 mL, 2 rel. vol.) and water (400 mL, 4 rel. vol.) were added to the reaction mixture, which was then heated to 75° C. Citric acid (10% w/v, 500 mL, 5 rel. vol.) was added slowly, such that the temperature was maintained above 70° C. During the addition of citric acid, product was noted to precipitate from solution. The resulting mixture was allowed to cool slowly to room temperature, at which temperature it was stirred overnight. The solid product was isolated by filtration, and washed with water (3×200 mL, 6 rel. vol.) on the filter. The filter cake was then washed with cold isopropanol (200 mL, 2 rel. vol.), before being dried by suction on the filter and then transferred to a vacuum oven. The product was dried to constant weight in vacuo at 50° C. for 20 hours. This gave the title compound as a white solid (168 g, 87%).

Water by KF analysis=3.17% (monohydrate requires 3.1%)

Alternative 4

A solution of 20% w/w aqueous sodium hydroxide (1.10 moles; 220.00 g), which was at 22° C., was added to a 2 L flask with stirring at 300 rpm. Water (24.98 moles; 450.00 mL; 450.00 g), which was at 22° C., was then added. The final temperature of the resulting mixture was 23° C. Solid 3-benzyl-9-oxa-3,7-diazabicyclo[3.3.1]nonane dihydrochloride (1.00 eq.; 343.38 mmoles; 100.00 g; see Preparation O above)

was added, at which point the temperature of the mixture rose to 26° C. Solid 2-(tert-butyloxycarbonylamino)ethyl 2,4,6-trimethylbenzene-sulfonate (1.05 eq.; 361.05 mmoles; 124.00 g.; see Preparation S below) was added (no temperature change due to this addition was observed). Toluene (2.17 moles; 231.21 mL; 200.00 g), which was at 22° C., was then added, which caused the temperature of the mixture to fall to 23° C. The mixture was heated from 23° C. to 65° C.±5° C. in 16 minutes and then held at this temperature for 6 hours 20 minutes. Stirring was stopped and the phases were allowed to settle (this took 55 seconds). The aqueous phase (first aqueous phase) was separated from the organic phase, keeping interfacial material with the organic phase. The temperature of the phases at separation was ca. 54° C. Under stirring, a solution of 10% w/w aqueous citric acid (260.25 mmoles; 500.00 g) was added to the toluene phase, to provide a mixture having a temperature of 40° C. The temperature of the mixture was then adjusted to 45° C., at which temperature stirring was stopped and the phases allowed to settle (this took 49 seconds). The resulting aqueous phase (second aqueous phase) was separated from the organic phase, leaving interfacial material with the organic phase. The organic phase was then discarded. Isopropanol (2.50 moles; 191.08 mL; 150.00 g), which was at 22° C., was added to the first aqueous phase (which was then at 49° C.) to provide a mixture having a temperature of 47° C. The second aqueous phase, which was then at 43° C., was added to the diluted first aqueous phase (at this point having a temperature of 44° C.) over the course of 50 seconds. This provided a mixture having a final temperature of 47° C. During the addition, a precipitate formed that ultimately hindered stirring in the vessel. The stirring rate was increased to 400 rpm and the mixture was heated to 72° C.±3° C. At 62° C., the mixture became stirrable. Upon reaching 72° C., the stirring rate was reduced to 350 rpm and the mixture was held at 72° C.±3° C. for 30 minutes before being allowed to cool overnight. The mixture was then cooled from 22° C. to 5° C. over the course of 1 hour, before being held at 5° C. for 55 minutes. The product was collected by filtration (15 cm diameter Büchner funnel), which took 65 seconds. The product cake was washed with cold (5° C.) water (22.20 moles; 400.00 mL; 400.00 g), which took 35 seconds. The product cake was next washed with cold (5° C.) isopropanol (4.99 moles; 382.17 mL; 300.00 g), which took 60 seconds (if desired, this isopropanol wash can be omitted to increase yield but potentially decrease product purity). The cake was sucked as dry as possible over 90 minutes, after which the resulting, damp solid (236 g) was dried in vacuo (at 70° C. for 5 hours) to give the title compound as a white solid (174.4 g, 90.4%). If desired, a longer drying period (e.g. 59 hours) at 70° C. in vacuo can be utilised to provide a solid with lower water content (water content approximately 0.3% w/w).

Water by KF analysis=2.8% w/w (monohydrate requires 3.1% w/w).

Alternative cooling profiles can be applied to the mixture (of first and second aqueous phases) in order to improve stirring properties of the mixture as well as filtration and washing properties, for example, as follows.

After cooling the reaction mixture (for convenience) to room temperature overnight, the mixture was heated to 80° C., with stirring at 500 rpm. The mixture was then:
(i) cooled, over the course of 60 minutes, to 70° C.;
(ii) heated from 70° C. to 75° C. over the course of 30 minutes;
(iii) cooled from 75° C. to 65° C. over the course of 60 minutes; and
(iv) cooled from 65° C. to 5° C. over the course of 120 minutes.

The resulting mixture was then held at 5° C. for 2 hours. The product was collected by filtration then washed and dried as above.

Preparation Q

[2-(7-Benzyl-9-oxa-3,7-diazabicyclo[3.3.1]non-3-yl) ethyl]carbamic acid tert-butyl ester, 2,4,6-trimethylbenzenesulfonic acid salt anhydrate Solid 3-benzyl-9-oxa-3,7-diazabicyclo[3.3.1]nonane dihydrochloride (55.0 kg, 1.0 eq.; see Preparation O above) and aqueous sodium hydroxide (2.5 M, 270.3 kg, 4.5 rel. vol.) were charged to a reaction vessel (VESSEL 1). Toluene (79.0 kg, 1.66 rel. vol.) was added and stirring was started. Solid 2-(tert-butyloxycarbonylamino)ethyl 2,4,6-trimethylbenzenesulfonate (71.5 kg, 1.10 mol. eq.; see Preparation S below) was charged to a second vessel (VESSEL 2) and toluene (171.0 kg, 3.59 rel. vol.) added. Stirring was started and the mixture heated to 29.3° C. over 44 minutes to form a solution. The solution at 29.3° C. in VESSEL 2 was then added to the mixture in VESSEL 1. VESSEL 2 was then charged with toluene (45 kg, 0.95 rel. vol.), heated to 29.7° C. and then added to the mixture in VESSEL 1. The mixture in VESSEL 1 was heated to 66.0° C. over 28 minutes with stirring and held at this temperature for 17 hours 55 minutes. Stirring was stopped and the phases allowed to separate over 66 minutes and the lower aqueous phase (first aqueous phase) sent to a vessel (VESSEL 3) at 64.4° C. Demineralised water (137.5 kg, 2.5 rel. vol.) and isopropanol (86.7 kg, 2 rel. vol.) were added to VESSEL 3, giving diluted first aqueous phase, the temperature of which was adjusted to 35° C. The organic phase (first organic phase) retained in VESSEL 1 was cooled to 17.4° C. and aqueous citric acid solution (0.5 M, 275.0 kg, 5 rel. vol.) was added and stirred for 36 minutes. The stirring was stopped and the phases allowed to separate for 25 minutes. The lower aqueous phase (second aqueous phase) was separated to a vessel (VESSEL 4) and the upper organic phase was discarded. The first aqueous phase (in VESSEL 3) was heated to 75.6° C. and the second aqueous phase added to it over 47 minutes (at such a rate so as to maintain the temperature in VESSEL 3 above 70° C. VESSEL 4 was charged with demineralised water (109.7 kg, 2 rel. vol.) and rinsed into the mixture in VESSEL 3. The mixture (initially observed to be at 73.3° C.) was then cooled to 20.6° C. over 4 hours 17 minutes, before being stirred for 10 hours 33 minutes (this time was used for convenience, as 4 hours is sufficient). The mixture was then filtered to give a solid. A displacement wash with demineralised water (330.4 kg, 6 rel. vol.) was carried out. The solid was then dried on the filter by applying vacuum and then by heating at 50° C. for 66 hours. This gave the title compound as a damp white solid (104.40 kg discharged, dry weight equivalent 92.26 kg, 87%).

Preparation R tert-Butyl (2-{7-[(2S)-3-(4-cyanophenoxy)-2-hydroxypropyl]-9-oxa-3,7-diazabicyclo[3.3.1]non-3-yl}ethyl)carbamate Alternative 1

(i) [2-(9-Oxa-3,7-diazabicyclo[3.3.1]non-3-yl)ethyl] carbamic acid tert-butyl ester, 2,4,6-trimethylbenzenesulfonic acid salt

[2-(7-Benzyl-9-oxa-3,7-diazabicyclo[3.3.1]non-3-yl) ethyl]carbamic acid tert-butyl ester 2,4,6-trimethylbenzenesulfonic acid salt (150 g; see Preparation P above), isopropanol (IPA; 450 mL) and water (150 mL) were combined in a metal hydrogenation vessel. Solid 5% Pd/C catalyst (4.5 g, 61% water wet, Johnson Matthey type 440) was added. The mixture was then hydrogenated under 2.5 bar of hydrogen pressure and was simultaneously heated to 55° C. Gas uptake measurement showed the reaction to be complete after 1 hour. After cooling to 39° C. the catalyst was removed by filtration through a glass fibre filter paper. The catalyst was washed on the filter with IPA (150 mL) and the combined filtrate and washings used in the next step.

(ii) tert-Butyl 2-{7-[(2S)-3-(4-cyanophenoxy)-2-hydroxypropyl]-9-oxa-3,7-diazabicyclo[3.3.1]non-3-yl}ethylcarbamate Aqueous sodium carbonate solution (1 M, 133 mL) was added to a solution of [2-(9-oxa-3,7-diazabicyclo[3.3.1]non-3-yl)ethyl]carbamic acid tert-butyl ester, 2,4,6-trimethylbenzenesulfonic acid salt (see step (i) above). A solution of 4-[(2S)-oxiranylmethoxy]benzonitrile (44.4 g; see, for example WO 01/28992) in IPA (75 mL) and toluene (75 mL) was added. The reaction was heated to 73° C. for 4 hours and then left to stir at ambient temperature overnight. Solvent (440 mL) was removed by distillation at less than 84° C. Toluene (1 L) was added and solvent was distilled (water 52 mL, organic solvent 441 mL). A further portion of toluene was added (500 mL) and solvent was distilled again (water 82 mL, organic solvent 437 mL). The mixture was then cooled to ambient temperature. Aqueous sodium hydroxide (1 M, 450 mL) was added and the mixture was stirred for 5 minutes and then the phases were separated. The aqueous phase was discarded and the toluene phase washed with aqueous citric acid (10% w/v, 450 mL). The toluene phase was discarded. 4-Methyl-2-pentanol (MIBC; 600 mL) and aqueous sodium hydroxide (5 M, 450 mL) were added to the citric acid phase. After stirring for 5 minutes the phases were separated and the aqueous discarded. The MIBC phase was washed with aqueous sodium chloride (20% w/v, 150 mL). The mixture of MIBC and aqueous sodium chloride was concentrated under reduced pressure at less than 50° C. (water (20 mL) and MIBC (55 mL) was collected). The MIBC solution was cooled to 33° C. and then left to stir overnight. The solution was filtered to a clean vessel. Solvent (285 mL) was distilled under reduced pressure at less than 70° C. Diisopropyl ether (IPE; 900 mL) was added at such a rate so that the temperature remained above 55° C. The solution was then allowed to cool to 23° C. After 90 minutes, crystallisation started and the mixture was stirred for 15 minutes before being cooled to 5° C. The product was collected by filtration. The solid was washed on the filter with IPE (300 mL) and sucked dry. Further drying in vacuo at 55° C. gave the title compound as a white solid (92.5 g, 78% over two steps).
Alternative 2

(i) [2-(9-Oxa-3,7-diazabicyclo[3.3.1]non-3-yl)ethyl]carbamic acid tert-butyl ester, 2,4,6-trimethylbenzenesulfonic acid salt

[2-(7-Benzyl-9-oxa-3,7-diazabicyclo[3.3.1]non-3-yl)ethyl]carbamic acid tert-butyl ester 2,4,6-trimethylbenzenesulfonic acid salt (150 g; see Preparation P above), isopropanol (IPA; 225 mL) and water (75 mL) were combined in a metal hydrogenation vessel. Solid 5% Pd/C catalyst (4.7 g, 61% water wet, Johnson Matthey type 440) was added. Hydrogen was introduced to the vessel and stirring was started. The mixture was hydrogenated under 2.5 bar of hydrogen pressure and was simultaneously heated to 55° C. (temperature overshot to 73° C.). Gas uptake measurement showed the reaction to be complete after 1 hour. After cooling to 47° C. the catalyst was removed by filtration through a glass fibre filter paper. The catalyst was washed on the filter with IPA (75 mL) and the combined filtrate and washings used in the next step.

(ii) tert-Butyl 2-{7-[(2S)-3-(4-cyanophenoxy)-2-hydroxypropyl]-9-oxa-3,7-diazabicyclo[3.3.1]non-3-yl}ethylcarbamate A solution of [2-(9-oxa-3,7-diazabicyclo[3.3.1]non-3-yl)ethyl]carbamic acid tert-butyl ester, 2,4,6-trimethylbenzenesulfonic acid salt (see step (i) above) was warmed to 55° C. Aqueous sodium carbonate solution (1 M, 133 mL) was added, followed by a warm (40° C.) solution of 4-[(2S)-oxiranylmethoxy]benzonitrile (44.4 g see, for example WO 01/28992) in IPA (75 mL) and toluene (75 mL). The solution was rinsed into the reaction flask with IPA (37 mL) and toluene (37 mL). The reaction was heated to 78° C. for 4 hours and then left to stir at ambient temperature overnight. Toluene was added (1050 mL) and solvent was distilled (600 mL). The mixture was then allowed to cool to 26° C. Aqueous sodium hydroxide (1 M, 450 mL) was added. The mixture was stirred for 5 minutes and then the phases were separated. The aqueous phase was discarded and the toluene phase washed with aqueous citric acid (10% w/v, 450 mL). The toluene phase was discarded. 4-Methyl-2-pentanol (MIBC; 600 mL) and aqueous sodium hydroxide (5 M, 450 mL) were added to the citric acid phase. After stirring for 5 minutes the phases were separated and the aqueous phase discarded. The MIBC phase was washed with aqueous sodium chloride (20% w/v, 150 mL) and the phases separated. The MIBC solution was then left to stir overnight (this overnight stir is unnecessary but in this example was carried out for convenience). The MIBC phase was concentrated under reduced pressure (78 mL of solvent was collected). The solution was filtered to a clean vessel, washing through with MIBC (150 mL). Solvent (437 mL) was distilled under reduced pressure at <70° C. Diisopropyl ether (IPE; 900 mL) was added at 55° C. and the temperature fell to 40° C. The solution was re-heated to 58° C. and then allowed to cool naturally to ambient temperature (at 28° C. a precipitate forms). The mixture was stirred overnight at ambient temperature. The mixture was cooled to 5° C. and the solid collected by filtration. The filter cake was washed by displacement with IPE (300 mL) and dried by suction on the filter. Further drying in vacuo at 70° C. gave the title compound as a white solid (97.3 g, 82% over two steps).
Alternative 3

(i) [2-(9-Oxa-3,7-diazabicyclo[3.3.1]non-3-yl)ethyl]carbamic acid tert-butyl ester, 2,4,6-trimethylbenzenesulfonic acid salt

[2-(7-Benzyl-9-oxa-3,7-diazabicyclo[3.3.1]non-3-yl)ethyl]carbamic acid tert-butyl ester 2,4,6-trimethylbenzenesulfonic acid salt (100 g of material that was 3.5% w/w water; see Preparation P above) was added to a metal hydrogenation vessel. Pre-mixed isopropanol (IPA; 150 mL) and water (50 mL) was added. Solid 5% Pd/C catalyst (4.0 g, 61% water wet, Johnson Matthey type 440) was added. Hydrogen was introduced to the vessel and stirring was started. The mixture was hydrogenated under 3.5 bar of hydrogen pressure and was simultaneously heated to 55° C. (temperature overshot to 68° C.). Gas uptake measurement showed the reaction to be complete after 3.5 hours. The reaction was filtered directly to the next reaction vessel at the appropriate point detailed below. The catalyst was washed with IPA (50 mL) and the wash added directly to the next reaction vessel at the appropriate point detailed below.

(ii) tert-Butyl 2-{7-[(2S)-3-(4-cyanophenoxy)-2-hydroxypropyl]-9-oxa-3,7-diazabicyclo[3.3.1]non-3-yl}ethylcarbamate A clean vessel was charged with 4-[(2S)-oxiranylmethoxy] benzonitrile (30.1 g see, for example WO 01/28992), followed by an aqueous solution of sodium carbonate (0.3 M, 300 mL). A solution of [2-(9-oxa-3,7-diazabicyclo[3.3.1] non-3-yl)ethyl]carbamic acid tert-butyl ester, 2,4,6-trimethylbenzenesulfonic acid salt (see step (i) above) was added followed by the catalyst wash (see step (i) above). The mixture was heated at reflux (78° C.) for 4 hours and then left at ambient temperature for 4 days (this standing period is unnecessary but in this example was carried out for convenience). Solvent was removed (236 mL) by distillation under reduced pressure (approximately 2.5 volumes of solvent need to be distilled to ensure removal of IPA). Toluene (400 mL) and aqueous sodium hydroxide (3 M, 100 mL) were added and the mixture stirred for 5 minutes. The phases were separated at 27° C. and the lower aqueous phase discarded. Aqueous citric acid (10% w/v, 300 mL) was added to the remaining toluene phase. After stirring for 5 minutes the phases were separated and the upper toluene phase discarded. 4-Methyl-2-pentanol (MIBC; 600 mL) and an aqueous solution of sodium hydroxide (5 M, 450 mL) containing sodium chloride (at 10% w/v) were added to the citric acid phase. After stirring for 5 minutes the phases were separated at 30° C. and the aqueous phase discarded. The MIBC phase was washed with aqueous sodium chloride (20% w/v, 100 mL) and after 5 minutes stirring the phases separated. The MIBC solution was then left to stand overnight (this overnight stand is unnecessary but in this example was carried out for convenience). The MIBC phase was concentrated under vacuum at a temperature of less than 44° C. (maximum temperature that can be reached at this part of the process is 70° C.); solvent was collected (water 18 mL: MIBC 35 mL). The solution was filtered to a clean vessel, washing through with MIBC (50 mL). Solvent (240 mL) was distilled under vacuum at less than 70° C. Diisopropyl ether (IPE; 600 mL) was added and the solution was re-heated to 64° C. The solution was stirred at 250 rpm and allowed to cool naturally. After 2 hours stirring, the temperature had fallen to 28° C. and precipitation of product had started. After stirring for a further 90 minutes, the temperature had fallen to 21° C. The mixture was cooled to 5° C. in 20 minutes and then held at this temperature for 90 minutes. The product was collected by filtration. The filter cake was washed by displacement with IPE (200 mL; IPE temperature was 20° C.) and dried by suction on the filter. The product was dried overnight in vacuo at 35° C. to give the title compound as a white solid (65.2 g, 85% over two steps).

Alternative 4

(i) [2-(9-Oxa-3,7-diazabicyclo[3.3.1]non-3-yl)ethyl] carbamic acid tert-butyl ester, 2,4,6-trimethylbenzenesulfonic acid salt

[2-(7-Benzyl-9-oxa-3,7-diazabicyclo[3.3.1]non-3-yl)-ethyl]carbamic acid tert-butyl ester 2,4,6-trimethylbenzenesulfonic acid salt (92.60 kg of material that was 17.51% w/w water; see Preparation P above) and solid 5% Pd/C catalyst (3.70 kg, 61% water wet, Johnson Matthey type 440) was added to a metal hydrogenation vessel. Pre-mixed isopropanol (IPA; 109.30 kg) and water (46.2 kg) was added. The vessel was purged with hydrogen to 0.5 bar to displace nitrogen and then hydrogen introduced to the vessel to 3.0 bar, stirring was started and simultaneous heating to 55° C. was begun (maximum temperature reached was 55.3° C.). The reaction mixture was held under hydrogen for 1 hour 45 minutes before the uptake of gas had stopped indicating that the reaction was complete. The reaction mixture was then cooled to 20° C. and left to stand for 21 hours 35 minutes (the standing period is unnecessary but was carried out for convenience). The reaction mixture was filtered into the next reaction vessel where indicated below and the catalyst cake was washed with IPA (35.9 kg) and added into the next reaction vessel where indicated below.

(ii) tert-Butyl 2-{7-[(2S)-3-(4-cyanophenoxy)-2-hydroxypropyl]-9-oxa-3,7-diazabicyclo[3.3.1]non-3-yl}ethylcarbamate A clean vessel was charged with 4-[(2S)-oxiranylmethoxy] benzonitrile (22.50 kg; see, for example WO 01/28992), demineralised water (184.7 kg) and sodium carbonate solution (1 M, 91.2 kg). A solution of [2-(9-oxa-3,7-diazabicyclo-[3.3.1] non-3-yl)ethyl]carbamic acid tert-butyl ester, 2,4,6-trimethylbenzene-sulfonic acid salt (see step (i) above) was added and the catalyst wash (see step (i) above) was also added. The mixture was heated to 78° C. over 35 minutes and held at this temperature for 4 hours, then cooled to 25.1° C. and left at room temperature for 84 hours 42 minutes (this standing period is unnecessary in this example was carried out for convenience). Solvent (215.3 kg) was removed by distillation under reduced pressure. Toluene (321.0 kg) was added and temperature of the reaction mixture was adjusted to 25.5° C. Sodium hydroxide solution (3 M, 101.7 kg) was charged to the reaction vessel and stirred for 23 minutes. Agitation was stopped and the phases were allowed to separate over 30 minutes. The lower aqueous phase was discarded. Stirring of the organic upper phase was restarted and aqueous citric acid solution (10% w/w, 278.3 kg) was added and stirred for 23 minutes. The agitation was stopped and the phases were allowed to separate over 40 minutes. The lower aqueous phase was sent to a second vessel (VESSEL 2) and the upper organic phase was discarded. The aqueous phase was then returned to the reaction vessel, stirring started and 4-methyl-2-pentanol (MIBC; 297.7 kg) and a pre-mixed solution of sodium hydroxide (10 M, 185.4 kg) and sodium chloride solution (20% w/w, 111.1 kg) was added and stirred for 15 minutes. Agitation was then stopped and the phases were allowed to separate over 30 minutes. The lower aqueous phase was discarded. Agitation was restarted and sodium chloride solution (20% w/w, 111.1 kg) was added and the contents of the reaction vessel stirred for 10 minutes. Agitation was stopped and the phases were allowed to separate for 18 minutes. The lower aqueous phase was discarded. Stirring was started and solvent (42.3 kg) was removed from the retained upper organic phase by distillation under reduced pressure. The concentrated solution was transferred to a clean vessel (VESSEL 3) and the reaction vessel was washed with water to remove residual salt contamination. The organic phase was then heated to 47.3° C. and filtered hot into the cleaned reaction vessel. MIBC (37.3 kg) was added to VESSEL 3 and then filtered into the reaction vessel and combined with the bulk of the solution. Solvent (240.3 kg) was then removed by distillation under reduced pressure keeping the temperature of the mixture below 70° C., after which the temperature was adjusted to 53.1° C. and diisopropyl ether (313.9 kg) was added. The temperature was adjusted to 51.6° C. and then cooled to 20° C. over 110 minutes and left to stand for 14 hours 49 minutes (this standing period is unnecessary but was carried out for convenience). The slurry was then cooled to 5° C. over 30 minutes and held at 5° C. for 30 minutes. The mixture was then filtered and a displacement wash of cold (5° C.) diisopropyl ether (134.5 kg) was added and the cake was blown with nitrogen for 135 minutes (this is unnecessary but was carried out for convenience). The solid was then dried on the filter under reduced pressure with heating at 30° C. for 87 hours to give the title compound as a white solid (49.05 kg, 80.7%).

Alternative 5

(i) [2-(9-Oxa-3,7-diazabicyclo[3.3.1]non-3-yl)-ethyl]-carbamic acid tert-butyl ester, 2,4,6-trimethyl-benzenesulfonic acid salt

[2-(7-Benzyl-9-oxa-3,7-diazabicyclo[3.3.1]non-3-yl) ethyl]carbamic acid tert-butyl ester, 2,4,6-trimethylbenzenesulfonic acid salt (150 g of material that was 3.33% w/w water; see Preparation P above) was added to a metal hydrogenation vessel. Pre-mixed isopropanol (IPA, 180 g) and water (75 g) was added. Solid 5% Pd/C catalyst (6.0 g, 61% water wet, Johnson Matthey type 440) was added. After nitrogen purge, hydrogen was introduced to the vessel and stirring was started. The mixture was hydrogenated under 3.5 bar of hydrogen pressure and was simultaneously heated to 65° C. over 15 minutes (temperature overshot to 73° C.). Gas uptake measurement showed the reaction to be complete after 30 minutes (which included the heat up time). After a further 30 minutes at 65° C., the reaction was cooled to 23° C. and then filtered directly into the next reaction vessel at the appropriate point detailed below. The catalyst was washed with IPA (60 g) and the wash added directly to the next reaction vessel at the appropriate point detailed below.

(ii) tert-Butyl 2-{7-[(2S)-3-(4-cyanophenoxy)-2-hydroxropyl]-9-oxa-3,7-diazabicyclo[3.3.1]non-3-yl}ethylcarbamate A clean vessel was charged with 4-[(2S)-oxiranylmethoxy] benzonitrile (44.3 g (see, for example WO 01/28992), 0.98 mol equiv. based on anhydrous [2-(7-benzyl-9-oxa-3,7-diazabicyclo[3.3.1]-non-3-yl)ethyl]carbamic acid tert-butyl ester, 2,4,6-trimethylbenzenesulfonic acid salt), followed by an aqueous solution of sodium carbonate (3% w/w, 480 g). The solution of [2-(9-oxa-3,7-diazabicyclo[3.3.1]non-3-yl) ethyl]carbamic acid tert-butyl ester, 2,4,6-trimethyl-benzenesulfonic acid salt (see step (i) above) was added, followed by the catalyst wash (see step (i) above). The resulting mixture was heated to reflux (78° C.) over 30 minutes and then held at this temperature for 2 hours. The reaction was cooled to 50° C. Solvent (353 g) was removed by distillation under reduced pressure at ≦50° C. Toluene (375 g) was added and the temperature adjusted to 28° C.±3° C. (All extraction operations that follow were conducted at this temperature). Aqueous sodium hydroxide (10% w/w, 180 g) was added and the mixture stirred for 5 minutes. The phases were separated and the lower aqueous phase discarded. Aqueous citric acid (10% w/w, 450 g) was added to the remaining toluene phase. After stirring for 5 minutes the phases were separated and the upper toluene phase discarded. 4-Methyl-2-pentanol (MIBC) (420 g) and an aqueous solution of sodium hydroxide/sodium chloride (15% w/w wrt NaOH, 7.5% w/w wrt NaCl, 600 g) were added to the citric acid phase. After stirring for 5 minutes the phases were separated and the aqueous phase discarded. The MIBC phase was washed with aqueous sodium chloride (20% w/w, 75 g) and after 5 minutes stirring the phases separated. The MIBC phase was concentrated under reduced pressure at ≦50° C. (84 g of solvent was removed). The solution was filtered to a clean vessel, washing through with MIBC (60 g). Solvent (239 g) was distilled out under vacuum at <70° C. Isopropyl ether (IPE) (653 g) was added and the solution was re-heated to above 55° C. The solution was stirred and allowed to cool overnight. The following day, the mixture was cooled from ambient temperature to 5° C. over 15 minutes. After 10 minutes stirring, the product was collected by filtration. The filter cake was washed by displacement with IPE (225 g; IPE temperature was 20° C.) and then dried by suction. The product was dried in vacuo at 55° C. to give the title compound as a white solid (100.2 g, 87% over two steps).

Alternative 6

(a) [2-(9-Oxa-3,7-diazabicyclo[3.3.1]non-3-yl)ethyl] carbamic acid tert-butyl ester, 2,4,6-trimethylbenzenesulfonic acid salt

[2-(7-Benzyl-9-oxa-3,7-diazabicyclo[3.3.1]non-3-yl) ethyl]carbamic acid tert-butyl ester, 2,4,6-trimethylbenzenesulfonic acid salt (1.00 equiv; 267.56 mmoles; 150.30 g of material that was 3.21% w/w water; see Preparation P above) was added to a hydrogenation vessel. Premixed isopropanol (3.00 moles; 229.30 mL; 180.00 g) and water (4.16 moles; 75.00 mL; 75.00 g) were added, followed by 5% palladium on carbon (4.50 g; ca. 57% w/w water; Engelhard 5398). The vessel was purged with nitrogen (3×) and hydrogen (2×) and then charged to 2 bar hydrogen pressure. Stirring (at 600 rpm) was initiated using a solid stirrer shaft fitted with a retreat curve impeller. Heating of the reaction mixture was started immediately, and the reaction reached the target temperature (to 65° C. i 5° C.) after 15 minutes. After a total reaction time of 50 minutes (including the heat up time) no further hydrogen was taken up (4.846 L had been consumed; theoretical volume consumption: 5.801 L). The reaction was cooled to 25° C. and reaction completion confirmed by thin layer chromatography (1:1 X:DCM as eluent, where X is chloroform: methanol: concentrated aqueous ammonia in the ratios 80:18:2; silica plates, with visualisation by potassium permanganate). (This cooling and sampling step can, if desired, be omitted.) The catalyst was removed by filtration directly into a 500 mL measuring cylinder. The catalyst was then washed with isopropanol (783.75 mmoles; 60.00 mL; 47.10 g).

The total volume of solution in the measuring cylinder was 480 mL, and this was then made up to 500 mL with isopropanol. The weight of solution (containing the sub-title compound) in the measuring cylinder was 461.5 g.

The weight of [2-(7-benzyl-9-oxa-3,7-diazabicyclo[3.3.1] non-3-yl)ethyl]carbamic acid tert-butyl ester, 2,4,6-trimethylbenzenesulfonic acid salt from which that solution was made is 150 g in 500 mL or 30% w/v.

The weight of [2-(7-benzyl-9-oxa-3,7-diazabicyclo[3.3.1] non-3-yl)ethyl]carbamic acid tert-butyl ester, 2,4,6-trimethylbenzenesulfonic acid salt from which that solution was made is 150 g in 461.5 g or 32.5% w/w.

(b) tert-Butyl 2-{7-[(2S)-3-(4-cyanophenoxy)-2-hydroxypropyl]-9-oxa-3,7-diaza-bicyclo[3.3.1]non-3-yl}ethylcarbamate A reaction flask was charged with a solution of 3% w/w aqueous sodium carbonate (95.10 mmoles; 326.40 mL; 336.00 g). A portion of the solution of [2-(9-oxa-3,7-diazabicyclo[3.3.1]non-3-yl)ethyl]carbamic acid tert-butyl ester, 2,4,6-trimethylbenzenesulfonic acid salt that was generated in part (a) above (350 mL; equates to 105.2 g of the [2-(7-benzyl-9-oxa-3,7-diazabicyclo[3.3.1]non-3-yl)ethyl]carbamic acid tert-butyl ester, 2,4,6-trimethylbenzenesulfonic acid salt precursor; the anhydrous equivalent is 101.8 g) was added. The mixture was heated to 40° C. over the course of 5 minutes, with stirring at 200 rpm. Solid 4-[(2S)-oxiranyl-methoxy]benzonitrile (174.67 mmoles; 30.60 g; see, for example WO 01/28992) was added and the reaction heated to 75° C. over 17 minutes. The reaction was held at this temperature for 2 hours. The contents of the flask weighed 678 g. A vacuum was applied, which caused the temperature to fall to ≦50° C., and solvent was removed by distillation. The flask contents now weighed 422 g (thus meaning that 256 g (2.44 rel wt) of solvent had been distilled). Toluene (2.85 moles; 301.88 mL; 263.00 g) was added to the flask contents (which were at 40° C.). An aqueous solution of sodium hydroxide (10% w/w) (315.02 mmoles; 113.63 mL; 126.00 g) was added before the resulting mixture was cooled to 30° C. After 12 minutes, stirring was stopped and the phases allowed to settle (settling occurred within 30 seconds). The phases were separated, at 30° C., leaving interfacial material with the (discarded) aqueous phase. (If desired, a further wash with aqueous base, such as a 10% w/w aqueous solution of sodium hydroxide, can be performed on the organic phase in order to remove traces of mesitylene sulfonic acid.) A solution of 10% w/w aqueous citric acid (163.96 mmoles; 302.83 mL; 315.00 g) was added to the toluene phase. After 7 minutes, stirring was stopped and the phases allowed to settle (settling occurred within 20 seconds). The phases were separated, at 29° C., leaving interfacial material with the (discarded) upper (organic) phase. 4-Methyl-2-pentanol (MIBC) (2.88 moles; 366.58 mL; 294.00 g) was added, followed by an aqueous solution of sodium hydroxide (15% w/w) and sodium chloride (7.5% w/w) (210.00 g). After 2 minutes, stirring was stopped and the phases allowed to settle (settling occurred within 60 seconds). The phases were separated, at 37° C., leaving interfacial material with the (discarded) lower (aqueous) phase. An aqueous solution of sodium chloride (20% w/w) (179.66 mmoles; 45.74 mL; 52.50 g) was added and stirred. After 2 minutes, stirring was stopped and the phases allowed to settle (settling occurred within 80 seconds). The phases were separated, at 35° C., leaving any interfacial material with the (discarded) lower (aqueous) phase. The contents of the flask weighed 395 g. The solution was distilled under vacuum, which led to the collection of 19 mL of water and 58 mL of MIBC. The flask contents now weighed 317 g (thus meaning that therefore 78 g (0.75 rel wt) had been removed by distillation). The remaining solution was filtered into a clean vessel and rinsed through with MIBC (411.05 mmoles; 52.37 mL; 42.00 g). The contents of the new flask weighed 351 g. The solution was left overnight (for convenience). During this time some crystallisation occurred. The mixture was heated to 60° C. and all material dissolved. The solution was distilled under vacuum at <70° C., leading to the collection of 183 mL of liquid (based on a density of MIBC of 0.802 this is 1.4 rel wt). Diisopropyl ether (DIPE) (3.24 moles; 457.00 mL; 331.32 g) was added to the hot (70° C.) MIBC solution, which caused the temperature of the mixture to fall to 52° C. The solution was re-heated to 60° C. and then allowed to cool naturally. After 27 minutes, the flask contents had reached 45° C. and seed crystals (56 mg) were added. The mixture was allowed to cool to 27° C. (this took 2 hours) by which time a large amount of precipitate was present. The mixture was cooled to 5° C. over the course of 24 minutes and then held at this temperature for 1 hour. The product was then collected by filtration (a process that took 45 seconds) and was washed with cold (5° C.) DIPE (1.54 moles; 217.24 mL; 157.50 g), which took 30 seconds. The filter cake was pulled as dry as possible on the filter (10 minutes). The damp material (99 g) was then dried in vacuo (at 55° C.) to constant weight (which took 1.5 hours). This gave the title compound as a white solid (68.3 g, 84%).

Preparation S 2-(tert-Butyloxycarbonylamino)ethyl 2,4,6-trimethylbenzenesulfonate Alternative 1

A solution of 2-aminoethanol (40 g, 655 mmol) in DCM (320 mL) was heated to 35° C.±3° C. To this, a solution of di-tert-butyl dicarbonate (147.35 g, 655 mmol) in DCM (200 mL) was added over 110 minutes. The reaction mixture was maintained at 35° C.±3° C. during the addition. After the addition was complete, the reaction mixture was maintained at 35° C.±3° C. for one hour. The reaction mixture was then cooled to 22° C.±2° C. and triethylamine (137 mL, 982 mmol) was added in one portion. The reaction mixture was then cooled to −10° C.±3° C. and trimethylamine hydrochloride (31.31 g, 327 mmol) was added in one portion. The resulting mixture was cooled further to −15° C.±3° C. and the reaction mixture was held at this temperature for five minutes. A solution of 2-mesitylenesulfonyl chloride (143.22 g, 655 mmol) in DCM (520 mL) was added slowly enough to maintain the temperature at less than −10° C., (30 minutes). After the addition was complete, the reaction mixture was maintained at −10° C.±3° C. for an additional five minutes. The reaction mixture was warmed to above 0° C. and water (800 mL) was added. The resulting biphasic mixture was stirred rapidly for five minutes and then the phases were separated. The organic layer was concentrated under reduced pressure at a temperature of less than 40° C. and solvent (960 mL) was collected. Isopropanol (960 mL) was added and the resulting solution was concentrated under reduced pressure at a temperature of less than 40° C. and solvent (320 mL) was collected. The resultant solution was cooled to 25° C.±3° C., and water (360 mL) was added slowly, whilst maintaining the temperature at 25° C.±3° C. (This causes the exothermic crystallisation of the title compound.) The mixture was stirred slowly and cooled to 10° C.±3° C., over ten minutes. The product was collected by filtration and then washed by displacement with 1:1 v/v isopropanol: water (160 mL). The product was dried in vacuo at 40° C. for 12±6 hours to give the title compound as a white crystalline solid (186.1 g, 83%).

m.p. 74° C.

$^1$H-NMR (300 MHz, CDCl$_3$): δ 6.98 (2H, s), 4.89 (1H, b), 4.01 (2H, t, J=5.1 Hz), 3.39 (2H, q, J=5.3 Hz), 2.62 (6H, s), 2.31 (3H, s), 1.41 (9H, s).

$^1$H-NMR (300 MHz, DMSO-d$_6$): δ 7.13 (2H, s), 6.97 (1H, t, J=5.5 Hz), 3.88 (2H, t, J=5.4 Hz), 3.15 (2H, q, J=5.5 Hz), 2.55 (6H, s), 2.29 (3H, s), 1.34 (9H, s).

Alternative 2

2-Aminoethanol (30.7 kg, 20.501 kmol; 1.0 eq.) was dissolved in dichloromethane (800 L, 1065 kg). The solution was heated to reflux (38° C. to 40° C.). Molten di-tert-butyl dicarbonate (109.6 kg, 0.501 kmol; 1.0 eq.) was added over a period of between 60 and 90 minutes. The reaction mixture was stirred at between 35° C. and 40° C. for 3 hours. The conversion of 2-aminoethanol was checked by GC. When the reaction was complete, the reaction mixture was cooled to 20° C. Triethylamine (105 L, 76.2 kg, 0.75 kmol; 1.50 eq.) was then added to the reaction vessel. The reaction mixture was then cooled to between 0° C. and −5° C. Trimethylamine hydrochloride (35.0 kg, 0.365 kmol; 0.72 eq.) and then a solution of mesitylenesulfonyl chloride (116.5 kg, 0.53 kmol; 1.06 eq.) in dichloromethane (380 L, 507.6 kg) were added to the reaction vessel. This addition was performed slowly enough such that the internal temperature was maintained below −2° C. The reaction mixture was stirred at −5° C. for 30 minutes and conversion was monitored by TLC. The solution was warmed to 3° C., and water (625 L) was added to the reaction mixture and stirring was maintained for between 10 and 20 minutes. After a settling time of between 15 to 30 minutes, the bottom layer (organic layer) was removed. The upper layer (aqueous layer) was discarded. The organic layer was transferred back to the vessel. The solvent was then exchanged from dichloromethane to isopropanol, which was effected by removing solvent (approximately 1000 L of dichloromethane) at reduced pressure (at a maximum temperature of <35° C.) and then replacing it with isopropanol (1050 L). Distillation was then continued until the volume remaining was approximately 590 L, after which water (180 kg) was added to the remaining solvent over 40 minutes at 20° C. The solution was seeded with between 0.6 kg and 0.8 kg of crystalline 2-(tert-butyloxycarbonylamino)ethyl 2,4,6-trimethylbenzenesulfonate. Water (110 kg) was then added over 25 minutes at 20° C., after which crystallisation took place. The resulting suspension was cooled to between 5° C. and 10° C. over 60 minutes, stirred at this temperature for another 60 minutes and then filtered. The product was washed twice with isopropanol:water (1:1 v/v, 220 L) and then dried at a maximum temperature of 35° C. under reduced pressure for 12 hours in a vacuum dryer. This gave the title compound in a yield of 93.8% (161.3 kg).

Preparation T tert-Butyl {3-[7-(3-hydroxypropyl)-9-oxa-3 7-diazabicyclo[3.3.1]non-3-yl]-propyl}carbamate To tert-butyl[3-(9-oxa-3,7-diazabicyclo[3.3.1]non-3-yl) propyl]carbamate (0.300 g; 1.05 mmol; see Preparation A above), 3-bromo-1-propanol (0.153 mg; 1.10 mmol) and potassium carbonate (0.218 mg; 1.58 mmol) was added acetonitrile (10 mL). The resulting mixture was heated to 60° C. and stirred overnight. The mixture was then filtered and the filtrate was concentrated in vacuo. The crude product was purified by filtration through silica gel (10 g, Isolute®, eluent: DCM (30 mL), acetonitrile (30 mL), DCM/MeOH 80:20 (140 mL) and DCM/MeOH(NH$_3$-satd.) (40 mL), 10 mL/fraction, product in fractions 8-22), which afforded 250 mg (69.2%) of the title compound.

$^1$H NMR (500 MHz, CDCl$_3$): δ 6.00 (1H, s, broad), 3.86 (2H, s), 3.75 (2H, m), 3.14-3.07 (4H, m), 2.91 (2H, m), 2.52-2.47 (4H, m), 2.39 (2H, m), 2.24 (2H, t), 1.73-1.64 (4H, m), 1.42 (9H, s)

EXAMPLES

Example 1 tert-Butyl (3-{7-[2-(4-cyano-2,6-difluorophenoxy ethyl]-9-oxa-3,7-diazabicyclo-[3.3.1]non-3-yl}propyl)carbamate 3,5-Difluoro-4-[2-(9-oxa-3,7-diazabicyclo[3.3.1]non-3-yl)ethoxy]benzonitrile hydrochloric acid salt (1.5 g, 3.92 mmol; see Preparation C above), tert-butyl (3-bromopropyl) carbamate (0.94 g, 3.93 mmol; see Preparation I above) and K$_2$CO$_3$ (1.08 g, 7.85 mmol) were mixed in acetonitrile (50 mL) and the reaction mixture was stirred at 60° C. under a nitrogen atmosphere for 24 h. The solids were filtered off and washed with acetonitrile. The solvent was then evaporated from the combined filtrates. The resulting crude product was purified by two times repeated chromatography on silica gel (Horizon™ flash system from Biotage™, column: Flash 40+M, 40×150 mm, using methanol saturated with ammonia in dichloromethane as eluent). The compound was further purified by preparative HPLC on a Waters® preparative HPLC system equipped with a Kromasil C$_8$ 10 μm, 250 mm×21.2 mm column, using a MeCN/NH$_4$OAc buffer system Yield: 0.42 g (22%)

(M+1)$^+$=467.24 (micromass LCT)

$^{13}$C NMR (125 MHz, CDCl$_3$): δ 159.48, 157.55, 157,50, 155,56, 155.51, 141,02, 118.47, 118.41, 118.32, 118.26, 117.65, 107.40, 80.36, 72.63, 67.58, 57.97, 57.46, 56.92, 55.97, 36.96, 28.79, 26.05.

Example 2 tert-Butyl (2-{7-[2-(4-cyano-2-fluorophenoxy) ethyl]-9-oxa-3,7-diazabicyclo-[3.3.1]non-3-yl}ethyl) carbaamate Alternative A A suspension of 3-fluoro-4-[2-(9-oxa-3,7-diazabicyclo [3.3.1]non-3-yl)ethoxy]-benzonitrile hydrochloric acid salt (5 g, 0.0137 mol; see Preparation D above), tert-butyl 2-bromoethylcarbamate (3.98 g, 0.0178 mol; see WO 01/28992) and potassium carbonate (7.57 g, 0.0548 mol) in dry acetonitrile (100 mL) was stirred at 60° C. overnight under a nitrogen atmosphere. The reaction mixture was filtered through Celite® and the filtrate was concentrated under reduced pressure. The residue was purified by column chromatography over silica gel, using 5% methanol in dichloromethane as eluent, to give 4.6 g of the title compound as an oil.

Alternative B tert-Butyl[2-(9-oxa-3,7-diazabicyclo[3.3.1]non-3-yl) ethyl]carbamate (2.46 g, 10.1 mmol; see WO 02/83690 and WO 2004/035592) and 4-(2-bromoethoxy)-3-fluorobenzonitrile (2.75 g, 10.1 mmol; see Preparation D(v) above) was mixed with K$_2$CO$_3$ (2.6 g, 19.1 mmol) in dry acetonitrile (150 mL). The reaction mixture was stirred at 60° C. under a nitrogen atmosphere overnight (19 h). The solids were filtered off and the solvent was evaporated. Toluene (60 mL) and citric acid 10% solution in water (50 mL) was added and the mixture was stirred at RT for 1.5 h. The phases were separated and the water layer was made basic by adding 2 M NaOH solution (50 mL). The aqueous layer was then extracted with ethyl acetate (75 mL) and the organic layer was separated, dried with MgSO$_4$ and then evaporated to give 4.39 g of the title compound as an oil that later solidified.

$^{13}$C NMR (125 MHz, CD$_3$OD): δ 158.26, 154.12, 152.46, 152.38, 152.14, 131.11, 120.68, 120.51, 118.90, 116.34, 104.93, 79.99, 69.71, 69.84, 68.65, 58.70, 57.88, 57.79, 56.64, 37.94, 28.78.

$^1$H NMR (500 MHz, CD$_3$OD) δ 7.56-7.54 (2H, d), 7.31 (1H, m), 4.39 (2H, t), 3.87 (2H, s), 3.19 (2H, t), 3.03 (2H, d), 2.88 (2H, d), 2.8 (2H, t), 2.63 (2H, dd), 2.59 (2H, dd), 2.41 (2H, t), 1.45 (9H, s)

Accurate mass: [C$_{22}$H$_{31}$N$_4$O$_4$F+H]$^+$=435.21 (within 5 ppm of the elemental compositions).

Alternative C

To [2-(7-benzyl-9-oxa-3,7-diazabicyclo[3.3.1]non-3-yl) ethyl]carbamic acid tert-butyl ester, 2,4,6-trimethylbenzenesulfonic acid salt (100 g; see Preparation P above), was added isopropanol (300 mL) and water (100 mL). To this was added 5% w/w palladium on carbon (4 g) (approximately 60% wet paste). This was heated to 65° C. and was hydrogenated at 3.5 bar. The reaction mixture was held at 65° C. for approximately sixteen hours before being cooled to 20° C.; total volume of hydrogen uptake was 4 L. The catalyst was removed by filtration and the catalyst was washed with isopropanol (50 mL). The combined organic filtrate and isopropanol catalyst washing were concentrated in vacuo. This gave a white crystalline solid, which was taken up in acetonitrile (1.28 L). To this was added 4-(2-bromoethoxy)-3-fluorobenzonitrile (43.5 g; see Preparation D(v) above) and potassium carbonate (250 g). The reaction was heated to reflux (approximately 80° C.), and held at this temperature for four hours. The reaction mixture was cooled to approximately 20° C. The reaction mixture was filtered, and the filter cake was washed with acetonitrile (250 mL). The combined organic filtrate and acetonitrile washings were concentrated in vacuo, and the residue was taken up in toluene (345 mL). This was then heated to 30° C. and kept at this temperature until the end of the extractive work-up. To the toluene solution was added a solution of sodium hydroxide (12 g) dissolved in water (110 mL). The layers were separated, and the lower (aqueous) phase was discarded. To the retained organic layer was added a solution of citric acid (30 g) dissolved in water (270 mL). The layers were separated, and the upper (organic) layer was discarded. To the retained aqueous layer was added ethyl acetate (330 mL), and a solution of sodium hydroxide (60 g) and sodium chloride (30 g) dissolved in water (310 mL). The layers were separated, and the lower (aqueous) phase was discarded. To the retained organic layer was added a solution of sodium chloride (10 g) dissolved in water (40 mL). The layers were separated, and the lower (aqueous) phase was discarded. The ethyl acetate layer was dried over magnesium sulfate (10 g), filtered and the drying agent was washed with ethyl acetate (220 mL). The combined organic filtrate and ethyl acetate washings were concentrated in vacuo, to yield the title compound as a light yellow oil containing white crystalline parts within it (72.00 g, 93% yield).

Crystallisation of the title compound can be carried out, if necessary, using the following method.

To tert-butyl (2-{7-[2-(4-cyano-2-fluorophenoxy)ethyl]-9-oxa-3,7-diazabicyclo-[3.3.1]non-3-yl}ethyl)carbamate (77 g) was added diisopropylether (385 mL) and isopropanol (77 mL). This mixture was heated to 65° C., and held at this temperature for fifteen minutes before being cooled to 5° C. over ninety minutes. Crystallisation was noticed at between 15 and 10° C. The mixture was held at 5° C. for two hours before being filtered and washed with cold diisopropylether (80 mL, 5° C.). The damp solid was dried in vacuo, at 35° C., for approximately nineteen hours, to give the crystallised title compound as an off-white solid (54.5 g, 71% yield).

$^1$H-NMR (CDCl$_3$, 300 MHz) δ 7.48-7.30 (m), 7.15-6.96 (m), 6.30-6.01 (m), 4.58-4.23 (m), 3.91-3.82 (m), 3.27-3.08 (m), 3.04-2.87 (m), 2.85-2.59 (m), 2.48-2.35 (m), 1.40 (s).

Alternative D
Sample 1

To [2-(7-benzyl-9-oxa-3,7-diazabicyclo[3.3.1]non-3-yl)ethyl]carbamic acid tert-butyl ester, 2,4,6-trimethylbenzenesulfonic acid salt (148 g; see Preparation P above), was added isopropanol (450 mL) and water (150 mL). To this was added 5% w/w palladium on carbon (7.5 g, approximately 60% wet paste). The resulting mixture was heated to 65° C. and was hydrogenated at 3.5 bar. The reaction mixture was maintained at 65° C., for approximately fourteen hours before being cooled to 20° C.; total volume of hydrogen uptake was 5.9 L. The catalyst was removed by filtration and the catalyst was washed with isopropanol (75 mL). The combined organic filtrate and isopropanol catalyst washings were concentrated in vacuo and the resulting residue (white crystalline solid) was taken up in acetonitrile (1.9 L). To this was added 2-(4-cyano-2-fluorophenoxy)ethyl toluene-4-sulfonate (88.3 g; see Preparation K above) and potassium carbonate (91 g). The reaction mixture was heated to reflux (approximately 80° C.), and was maintained at this temperature for eight hours, before cooling to room temperature (approximately 20° C.). The reaction mixture was filtered and the filter cake was washed with acetonitrile (190 mL). The combined filtrate and acetonitrile cake washings were concentrated in vacuo and the resulting residue was taken up in toluene (850 mL). To this was added a solution of sodium hydroxide (26.6 g) dissolved in water (240 mL). The layers were separated, and the lower (aqueous) layer was discarded. To the retained organic layer was added a solution of citric acid (44.4 g) dissolved in water (400 mL). The layers were separated, and the upper (organic layer) was discarded. To the retained aqueous layer was added ethyl acetate (1.25 L) and a solution of sodium hydroxide (89 g) and sodium chloride (44.4 g) dissolved in water (460 mL). The layers were separated, and the lower (aqueous) layer was discarded. To the retained organic layer was added a solution of sodium chloride (15 g) dissolved in water (60 mL). The layers were separated, and the lower (aqueous) layer was discarded. The retained organic layer was dried over magnesium sulfate (75 g). The magnesium sulfate was removed by filtration and the drying agent was washed with ethyl acetate (410 mL). The combined organic filtrate and ethyl acetate washing were concentrated in vacuo to yield a yellow oil (97 g). This oil was taken up in diisopropylether (485 mL) and isopropanol (100 mL). This was then heated to reflux (approximately 68° C.). At reflux all of the material had dissolved, and the reaction mixture was cooled to room temperature (approximately 20° C.). The mixture was further cooled to 5° C. before being filtered and washed with cold diisopropylether (200 mL, 5° C.). The damp solid was dried in vacuo, at 35° C., to give the title compound as an off white solid (60 g, 52.4% yield).

Sample 2

To [2-(7-benzyl-9-oxa-3,7-diazabicyclo[3.3.1]non-3-yl)ethyl]carbamic acid tert-butyl ester, 2,4,6-trimethylbenzenesulfonic acid salt (173 g; see Preparation P above), was added isopropanol (530 mL) and water (175 mL). Then 5% w/w palladium on carbon (8.7 g of approximately 60% wet paste) was added. The reaction mixture was heated to 65° C. and was hydrogenated at 3.5 bar. The reaction mixture was maintained at 65° C. for two hours, and was then cooled to 20° C.; total volume of hydrogen uptake was 7.1 L. The catalyst was removed by filtration, and the catalyst was washed with isopropanol (90 mL). The combined organic filtrate and isopropanol catalyst washings were concentrated in vacuo, and the residue (white crystalline solid) was taken up in acetonitrile (2.2 L). To this was added 2-(4-cyano-2-fluorophenoxy)ethyl toluene-4-sulfonate (103.3 g; see Preparation K above) and potassium carbonate (106.5 g). This was then heated to reflux (approximately 80° C.), over approximately half an hour. The reaction mixture was maintained at 80° C. for eight hours, before cooling to room temperature (approximately 20° C.). The reaction mixture was filtered and the filter cake was washed with acetonitrile (220 mL). The combined filtrate and acetonitrile cake washings were concentrated in vacuo and the resulting residue was taken up in toluene (1 L). To this was added a solution of sodium hydroxide (31.2 g) dissolved in water (280 mL). The layers were separated, and the lower (aqueous) layer was discarded. To the retained organic layer was added a solution of citric acid (52 g) dissolved in water (470 mL). The layers were separated, and the upper (organic)

layer was discarded. To the retained aqueous layer was added ethyl acetate (1.45 L) and a solution of sodium hydroxide (104 g) and sodium chloride (52 g) dissolved in water (540 mL). The layers were separated, and the lower (aqueous) layer was discarded. To the retained organic layer was added a solution of sodium chloride (17.3 g) dissolved in water (70 mL). The layers were separated, and the lower (aqueous) layer was discarded. The organic layer was dried over magnesium sulfate (87 g), filtered and the drying agent washed with ethyl acetate (480 mL). The combined organic filtrate and ethyl acetate cake washings were concentrated in vacuo to yield a yellow oil (113 g). To this oil was added diisopropylether (600 mL) and isopropanol (110 mL), this mixture was heated to reflux (approximately 68° C.). At reflux, all of the material had dissolved, and the reaction mixture was cooled to room temperature (approximately 20° C.). The reaction mixture was further cooled to 5° C., and the reaction mixture was filtered. The solid was washed with cold diisopropylether (240 mL, 5° C.). The damp solid was dried in a vacuum oven, at 35° C., to give the title compound as an off white solid (79 g, 59% yield).

Sample 3

The final filtrates and the washes from the above two procedures, were combined and concentrated in vacuo to give a further 80 g of the crude title compound. To this crude mixture was added diisopropylether (530 mL) and isopropanol (70 mL), which gave a mixture that was then heated to 65° C. At 65° C., all of the material had dissolved and the mixture was cooled to room temperature (approximately 20° C.). The mixture was then further cooled to 5° C. before it was filtered and the solid was washed with cold diisopropylether (70 mL, 5° C.). The damp solid was dried in vacuo, at 35° C., to give purified title compound as an off white solid (25 g, 31.3% yield).

The title compound samples resulting from the above three procedures (i.e. Samples 1 to 3: 60 g, 79 g and 25 g, respectively) were combined. To the combined mixture was added diisopropylether (820 mL) and isopropanol (82 mL). This mixture was heated to 65° C., at which temperature a solution had formed. The reaction mixture was cooled over three hours to room temperature (approximately 20° C.). Crystallisation was noticed at between 45 and 40° C. The mixture was further cooled to 5° C. over twenty minutes and held at 5° C. for twenty more minutes. The reaction mixture was filtered and the solid was washed with cold diisopropylether (165 mL, 5° C.). The damp solid was dried in vacuo, at 35° C., to give recrystallised title compound as an off white solid (149.3 g, 91% yield).

$^1$H-NMR (CDCl$_3$, 300 MHz) δ H 7.49-7.29 (m, 2H), 7.16-6.94 (m, 1H), 6.31-6.02 (m, 1H), 4.57-4.21 (m, 2H), 3.93-3.82 (m, 2H), 3.28-3.07 (m, 2H), 3.05-2.87 (m, 2H), 2.85-2.62 (m, 8H), 2.49-2.37 (m, 2H), 1.43 (s, 9H).

Alternative E

To [2-(7-benzyl-9-oxa-3,7-diazabicyclo[3.3.1]non-3-yl)ethyl]carbamic acid tert-butyl ester, 2,4,6-trimethylbenzenesulfonic acid salt (60 g; see Preparation P above) was added a solution of isopropanol (92 mL) and water (30 mL). To this was added 5% w/w palladium on carbon (2.4 g of 61% wet paste). The reaction mixture was heated to 65° C. and was hydrogenated at 2.5 bar. The reaction mixture was held at 65° C. for twenty minutes, and was then cooled to 20° C.; total volume of hydrogen uptake was 2.2 L. The catalyst was removed by filtration and the catalyst was washed with isopropanol (31 mL). The organic filtrate and the isopropanol catalyst washings were combined. To this was added 2-(4-cyano-2-fluorophenoxy)ethyl toluene-4-sulfonate (35.1 g; see Preparation K above), and a solution of sodium carbonate (6.3 g) dissolved in water (186 mL). The reaction mixture was heated to 75° C., at approximately 1° C. per minute. The reaction mixture was held at 75° C. for twelve hours then cooled to 20° C., at approximately 1° C. per minute. The reaction mixture was reduced in volume by reduced pressure distillation (at less than 50° C.), and approximately 150 mL of solvent was removed. To the remaining reaction mixture was added toluene (175 mL) and the reaction temperature was adjusted to 30° C. and kept at this temperature until the end of the extractive work up. To the toluene solution was added a solution of sodium hydroxide (10.8 g) dissolved in water (98 mL). The layers were separated and the lower (aqueous) layer was discarded. To the retained organic layer was added a solution of citric acid (18.0 g) dissolved in water (162 mL). The layers were separated and the upper (organic) layer was discarded. To the retained aqueous layer was added 4-methylpentan-2-ol (210 mL), and a solution of sodium hydroxide (36 g) and sodium chloride (18 g) dissolved in water (186 mL). The layers were separated and the lower (aqueous) layer was discarded. To the retained organic layer was added a solution of sodium chloride (6 g) dissolved in water (24 mL). The layers were separated and the lower (aqueous) layer was discarded. The resulting mixture was reduced in volume by reduced pressure distillation (at less than 70° C., resulting in the removal of approximately 55 mL of solvent). This was then filtered to a clean vessel and was washed with 4-methylpentan-2-ol (30 mL). The mixture was reduced in volume by reduced pressure distillation (at less than 70° C.), and approximately 155 mL of solvent was removed. To the residue was added diisopropylether (560 mL), whilst maintaining the temperature above 55° C. The mixture was cooled to 20° C., at approximately 0.25° C. per minute, then held at 20° C. for approximately sixteen hours. The mixture was cooled to 5° C., at approximately 0.25° C. per minute, and was held at 5° C. for approximately an hour. The mixture was filtered and the product was washed with cold diisopropylether (125 mL, 5° C.). The damp solid was dried in vacuo, at 35° C., for approximately twenty-two hours, to give the title compound as a white, crystalline solid (29 g, 63% yield).

Recrystallisation of the title compound can be carried out, if necessary, using the following method.

To tert-butyl (2-{7-[2-(4-cyano-2-fluorophenoxy)ethyl]-9-oxa-3,7-diazabicyclo-[3.3.1]non-3-yl}ethyl)carbamate (164 g) was added diisopropylether (820 mL) and isopropanol (82 mL). This mixture was then heated to 65° C., at which point a solution had formed. The reaction mixture was cooled to room temperature (approximately 20° C.). Crystallisation was noticed at between 45 and 40° C. The mixture was further cooled to 5° C. before it was filtered and the solid was washed with cold diisopropylether (165 mL, 5° C.). The damp solid was dried in vacuo, at 35° C., for approximately eighteen hours, to give recrystallised title compound (149.3 g; 91%).

$^1$H NMR (400 MHz, CD$_3$OD): δ 7.53 (d, J=9.8 Hz, 2H), 7.29 (t, J=8.2 Hz, 1H), 4.38 (t, J=5.9 Hz, 2H), 3.89-3.82 (m, 2H), 3.17 (t, J=6.3 Hz, 2H), 3.01 (d, J=11.5 Hz, 2H), 2.86 (d, J=11.3 Hz, 2H), 2.78 (t, J=6.0 Hz, 2H), 2.67-2.60 (m, 2H), 2.60-2.53 (m, 2H), 2.39 (t, J=6.2 Hz, 2H), 1.41 (s, 9H).

Alternative F

To [2-(7-benzyl-9-oxa-3,7-diazabicyclo[3.3.1]non-3-yl)ethyl]carbamic acid tert-butyl ester, 2,4,6-trimethylbenzenesulfonic acid salt (60 g; see Preparation P above) was added a solution of isopropanol (90 mL) and water (30 μL). To this was added 5% w/w palladium on carbon (2.4 g of 61% wet paste). The reaction mixture was heated to 65° C. and was hydrogenated at 2.5 bar. The reaction mixture was maintained at 65° C. for approximately forty-five minutes and was then cooled to 20° C.; total volume of hydrogen uptake was 2.2 L. The catalyst was removed by filtration and the catalyst was washed with isopropanol (31 mL). To the combined organic filtrate and the isopropanol catalyst washings was added 2-(4-cyano-2-fluorophenoxy)ethyl toluene-4-sulfonate (35.1 g; see Preparation K above) and a solution of sodium carbonate (63 g) dissolved in water (186 mL). The reaction mixture was heated to 75° C., at approximately 1° C. per minute, then held at this temperature for twelve hours, before being cooled to 20° C. (at approximately 1° C. per minute). The reaction mixture was reduced in volume by reduced pressure distillation (at less than 50° C.), and approximately 140 mL of solvent was removed. To the remaining mixture was added toluene (172 µL), and the reaction temperature was adjusted to 30° C. and kept at this temperature until the end of the extractive work up. To the toluene solution was added a solution of sodium hydroxide (10.8 g) dissolved in water (97 mL). The layers were separated and the lower (aqueous) layer was discarded. This extraction with aqueous sodium hydroxide was repeated once more, the lower (aqueous) layer again being discarded. To the retained organic layer was added a solution of citric acid (18 g) dissolved in water (162 mL). The layers were separated and the upper (organic) layer was discarded. To the retained aqueous layer was added ethyl acetate (210 mL) and a solution of sodium hydroxide (36 g) and sodium chloride (18 g) dissolved in water (186 mL). The layers were separated and the lower aqueous layer was discarded. To the retained organic layer was added a solution of sodium chloride (6 g) dissolved in water (24 mL). The layers were separated and the lower aqueous layer was discarded. The retained organic layer was dried over magnesium sulfate (30 g): The inorganic solids were removed by filtration, and washed with ethyl acetate (30 mL). The combined filtrate and washings were concentrated in vacuo, at less than 50° C., to give a colourless oil (40 g). To this oil was added diisopropylether (175 mL) and isopropanol (35 mL). This mixture was heated to 65° C., at approximately 1° C. per minute. The temperature was then maintained at 65° C. for fifteen minutes. The mixture was then cooled to 20° C. (at approximately 0.25° C. per minute), held at 20° C. for approximately sixteen hours, then cooled to 5° C. (at approximately 0.25° C. per minute), before being held at this final temperature for approximately one hour. The reaction mixture was filtered and the solid was washed with cold diisopropylether (36 mL, 5° C.). The damp solid was dried in vacuo, at 35° C., to give the title compound as a white solid (28.2 g, 61% yield).

Alternative G

To [2-(7-benzyl-9-oxa-3,7-diazabicyclo[3.3.1]non-3-yl) ethyl]carbamic acid tert-butyl ester, 2,4,6-trimethylbenzenesulfonic acid salt (300 g; see Preparation P above) was added isopropanol (460 mL) and water (150 mL). To the resulting mixture was added 5% w/w palladium on carbon (12 g of approximately 60% wet paste). The mixture was then heated to 65° C. and was hydrogenated at 2.5 bar. The reaction mixture was held at 65° C. for approximately twenty minutes before being cooled to 20° C.; total volume of hydrogen uptake was 11.4 L. The catalyst was removed by filtration and was washed with isopropanol (150 mL). The organic filtrate and the isopropanol catalyst washings were combined. To this was added 2-(4-cyano-2-fluorophenoxy)ethyl toluene-4-sulfonate (175.5 g; see Preparation K above) and a solution of sodium carbonate (315 g) dissolved in water (930 mL). The reaction mixture was heated to 75° C., at which temperature it was held for twelve hours before being cooled to 20° C. The reaction mixture was reduced in volume by reduced pressure distillation (at less than 50° C.), and approximately 650 mL of solvent was removed. To the remaining reaction mixture was added toluene (860 mL) and the reaction temperature was adjusted to 30° C. and kept at this temperature until the end of the extractive work-up. To the toluene solution was added a solution of sodium hydroxide (54 g) dissolved in water (485 mL). The layers were separated and the lower (aqueous) layer was discarded. To the retained (organic) solution was added a solution of sodium hydroxide (54 g) dissolved in water (485 mL). The layers were separated and the lower (aqueous) layer was discarded. To the retained (organic) layer was added a solution of citric acid (90 g) dissolved in water (810 mL). The layers were separated and the upper (organic) layer was discarded. To the retained (aqueous) layer was added ethyl acetate (1.05 L), and a solution of sodium hydroxide (180 g) and sodium chloride (90 g) dissolved in water (930 mL). The layers were separated and the lower (aqueous) layer was discarded. To the retained (organic) layer was added a solution of sodium chloride (30 g) dissolved in water (120 mL). The layers were separated and the lower (aqueous) layer was discarded. The retained (organic) layer was dried over magnesium sulfate (150 g). The inorganic solids were removed by filtration, and washed with ethyl acetate (150 mL). The combined filtrate and washings were concentrated in vacuo, at less than 50° C., to give crude title compound as a yellow solid (201 g).

The above procedure was repeated three further times (starting once with 300 g of [2-(7-benzyl-9-oxa-3,7-diazabicyclo[3.3.1]non-3-yl)ethyl]carbamic acid tert-butyl ester 2,4,6-trimethylbenzenesulfonate and twice with 450 g of this material) to provide batches of 200, 304 and 300 g of crude title compound.

The four batches of crude title compound mentioned above (0.2 kg, 0.2 kg, 0.3 kg and 0.3 kg) were combined. Diisopropylether (5 L) and isopropanol (1 L) were added to the combined material. The resulting mixture was heated to 65° C., at which temperature a solution had formed. The reaction mixture was cooled over approximately six hours to room temperature (approximately 20° C.). Crystallisation was noticed at approximately 37° C. For convenience, the reaction mixture was held at 20° C. for approximately sixteen hours. The reaction mixture was further cooled to 5° C. over fifty minutes and held at 5° C. for five minutes. The reaction mixture was filtered and the solid was washed with cold diisopropylether (1 L, 5° C.). The damp solid was dried in vacuo, at 35° C., to give purified title compound as an off-white solid (741 g, 74% yield).

$^1$H NMR (400 MHz, CD$_3$OD): δ 7.53 (d, J=9.5 Hz, 2H), 7.30 (d, J=8.2 Hz, 1H), 4.38 (t, J=5.9 Hz, 2H), 3.88-3.82 (m, 2H), 3.17 (t, J=6.2 Hz, 1H), 3.01 (d, J=11.2 Hz, 2H), 2.86 (d, J=12.1 Hz, 2H), 2.78 (t, J=5.8 Hz, 2H), 2.67-2.60 (m, 2H), 2.60-2.54 (m, 2H), 2.39 (t, J=6.2 Hz, 2H), 1.37 (s, 9H).

Alternative H

To [2-(7-benzyl-9-oxa-3,7-diazabicyclo[3.3.1]non-3-yl) ethyl]carbamic acid tert-butyl ester 2,4,6-trimethylbenzenesulfonate (30 g; see Preparation P above) was added a solution of isopropanol (46 mL) and water (15 mL). To this was added 5% w/w palladium on carbon (1.2 g of 61% wet paste). The reaction mixture was heated to 65° C. and was hydrogenated at 2.5 bar. The reaction mixture was held at 65° C. for twenty minutes, and was then cooled to 20° C.; total volume of hydrogen uptake was 1.1 L. The catalyst was removed by filtration and was then washed with isopropanol (15 mL). The organic filtrate and the isopropanol catalyst washings were combined. To this was added 2-(4-cyano-2-fluorophenoxy) ethyl toluene-4-sulfonate (17.55 g; see Preparation K above), and a solution of sodium carbonate (5.94 g) dissolved in water (93 mL). The reaction mixture was heated to 75° C., at approximately 1° C. per minute. The reaction mixture was held at 75° C. for twelve hours then cooled to 20° C., at approximately 1° C. per minute. The reaction mixture was reduced in volume by reduced pressure distillation (at less than 50° C.), and approximately 60 mL of solvent was removed. To the remaining reaction mixture was added toluene (75 mL) and the reaction temperature was adjusted to 30° C. and kept at this temperature until the end of the extractive work up. To the toluene solution was added a solution of sodium hydroxide (3.6 g) dissolved in water (32 mL). The layers were separated and the lower (aqueous) layer was discarded. To the retained organic layer was added a solution of citric acid (9 g) dissolved in water (81 mL). The layers were separated and the upper (organic) layer was discarded. To the retained aqueous layer was added 4-methyl-pentan-2-ol (104 mL), and a solution of sodium hydroxide (18 g) and sodium chloride (9 g) dissolved in water (93 mL). The layers were separated and the lower (aqueous) layer was discarded. To the retained organic layer was added a solution of sodium chloride (3 g) dissolved in water (12 mL). The layers were separated and the lower (aqueous) layer was discarded. The resulting mixture was reduced in volume by reduced pressure distillation (at less than 70° C., resulting in the removal of approximately 15 mL of solvent). This was then filtered to a clean vessel and was washed with 4-methylpentan-2-ol (15 mL). The mixture was reduced in volume by reduced pressure distillation (at less than 70° C.), and approximately 90 mL of solvent was removed. To the residue was added diisopropylether (280 mL), whilst maintaining the temperature above 40° C. The mixture was re-heated to 55° C. before being cooled to 20° C. (at approximately 0.25° C. per minute), at which temperature it was held for approximately fourteen hours. The mixture was then cooled to 5° C., at approximately 0.25° C. per minute, and was held at 5° C. for approximately two hours. The mixture was filtered and the filter cake was washed with cold diisopropylether (62 mL, 5° C.). The damp solid was dried in vacuo (at 35° C. for approximately twenty-two hours) to give the title compound as a white, crystalline solid (17.8 g, 77% yield).

Alternative I

To [2-(7-benzyl-9-oxa-3,7-diazabicyclo[3.3.1]non-3-yl)ethyl]carbamic acid tert-butyl ester, 2,4,6-trimethylbenzenesulfonic acid salt (101 g; see Preparation P above) was added a solution of isopropanol (152 mL) and water (50 mL). To this was added 5% w/w palladium on carbon (4 g of 61% wet paste). The reaction mixture was heated to 65° C. and was hydrogenated at 2.5 bar. The reaction mixture was held at 65° C. for approximately one hour, and was then cooled to 20° C.; total volume of hydrogen uptake was 3.8 L. The catalyst was removed by filtration and washed with isopropanol (50 mL). The organic filtrate and the isopropanol catalyst washings were combined. To this was added 2-(4-cyano-2-fluorophenoxy)ethyl toluene-4-sulfonate (58.95 g; see Preparation K above), and a solution of sodium carbonate (20.01 g) dissolved in water (310 mL). The reaction mixture was heated to 75° C. The reaction mixture was held at 75° C. for twelve hours then cooled to 20° C. The reaction mixture was reduced in volume by reduced pressure distillation (at less than 45° C.), and approximately 210 mL of solvent was removed. To the remaining reaction mixture was added toluene (290 mL) and the reaction temperature was adjusted to 30° C. and kept at this temperature until the end of the extractive work up. To the toluene solution was added a solution of sodium hydroxide (18.01 g) dissolved in water (162 mL). The layers were separated and the lower (aqueous) layer was discarded. To the retained organic layer was added a solution of sodium hydroxide (18.18 g) dissolved in water (162 mL). The layers were separated and the lower (aqueous) layer was discarded. To the retained organic layer was added a solution of citric acid (30.15 g) dissolved in water (270 mL). The layers were separated and the upper (organic) layer was discarded. To the retained aqueous layer was added 4-methylpentan-2-ol (350 mL), and a solution of sodium hydroxide (60.32 g) and sodium chloride (30.27 g) dissolved in water (310 mL). The layers were separated and the lower (aqueous) layer was discarded. To the retained organic layer was added a solution of sodium chloride (10.07 g) dissolved in water (40 mL). The layers were separated and the lower (aqueous) layer was discarded. The resulting mixture was reduced in volume by reduced pressure distillation (at less than 60° C., resulting in the removal of approximately 180 mL of solvent), filtered to a clean vessel and then washed with 4-methyl-pentan-2-ol (50 mL). The mixture was reduced in volume by reduced pressure distillation (at less than 60° C.), and approximately 124 mL of solvent was removed. To the residue was added diisopropylether (935 mL), whilst maintaining the temperature above 55° C. The mixture was cooled to 20° C. and then to 5° C., at which temperature it was held for approximately an hour. The mixture was filtered and the product was washed with cold diisopropylether (200 mL, 5° C.). The damp solid was dried in vacuo, at 35° C., for approximately twenty-five hours, to give the title compound as a white, crystalline solid (51.4 g, 66% yield).

$^1$H NMR (400 MHz, CD$_3$OD): δ 7.50 (d, J=9.5 Hz, 2H), 7.27 (t, J=8.3 Hz, 1H), 4.36 (t, J=5.8 Hz, 2H), 3.83 (t, J=3.5 Hz, 2H), 3.15 (t, J=6.2 Hz, 2H), 2.99 (d, J=11.5 Hz, 2H), 2.84 (d, J=11.3 Hz, 2H), 2.76 (t, J=6.0 Hz, 2H), 2.66-2.50 (m, 4H), 2.37 (t, J=6.3 Hz, 2H), 1.36 (s, 9H).

Crystallisation of the title compound can be carried out, if necessary, using either of the following methods.

Method 1

To tert-butyl (2-{7-[2-(4-cyano-2-fluorophenoxy)ethyl]-9-oxa-3,7-diazabicyclo-[3.3.1]non-3-yl}ethyl)carbamate (25 g) was added diisopropyl ether (125.00 mL) and isopropanol (12.50 mL), at 20° C., 450 RPM. This mixture was heated to 65° C. over one hour and thirty minutes, and held at this temperature for fifteen minutes before being cooled to 20° C. over ninety minutes. The mixture was held at 20° C. for thirty minutes. The mixture was seeded, this caused immediate crystallisation. The mixture was heated to 40° C. over forty minutes. The mixture was cooled to 20° C. over one hour and forty minutes. The mixture was heated to 40° C. over forty minutes. The mixture was cooled to 20° C. over one hour and forty minutes. The mixture was heated to 40° C. over forty minutes. The mixture was cooled to 20° C. over one hour and forty minutes. The mixture was held 20° C., for approximately 10 hours. The mixture was cooled to 5° C. over thirty minutes. The mixture was held at 5° C. for five minutes before being filtered and washed with cold diisopropyl ether (50 mL, 5° C.). The damp solid was dried in vacuo at 35° C., for approximately twenty-four hours to give the crystallised title compound a white crystalline solid (21 g, 84%).

$^1$H-NMR (300 MHz, CD$_3$OD): δ 7.64-7.46 (m, 2H), 7.40-7.25 (m, 1H), 4.49-4.35 (m, 2H), 3.95-3.84 (m, 2H), 3.27-3.14 (m, 2H), 3.04 (d, J=9.8 Hz, 2H), 2.96-2.76 (m, 4H), 2.74-2.53 (m, 4H), 2.50-2.37 (m, 2H), 1.42 (s, 9H).

Alternative solvent systems for the crystallisation of the title compound include IPE/MIBC (in ratios from 100:5 to 100:15).

Method 2

To tert-butyl (2-{7-[2-(4-cyano-2-fluorophenoxy)ethyl]-9-oxa-3,7-diazabicyclo-[3.3.1]non-3-yl}ethyl)carbamate (50 g) was added 385 mL of premixed diisopropyl ether (500 mL) and isopropanol (50 mL), at 20° C., 300 RPM. This mixture was heated to 65° C. at 0.3° C./min, and held at this temperature for 30 minutes before being cooled to 39° C. at 0.3° C./min. The mixture was seeded (0.5 g solid) and held at 39° C. for either 2 hours or 30 minutes. The mixture was cooled to 5° C. at 0.3° C./min. The mixture was held at 5° C., for approximately 14 hours, for convenience, before being filtered and washed with diisopropyl ether (50 mL). (If desired the wash with diisopropyl ether can be omitted.) The damp solid was dried in vacuo at 40° C., for approximately twenty-four hours to give the crystallised title compound a white crystalline solid.

Yield: 41 g (from a procedure using a 2 hour hold at 39° C. and a diisopropyl ether wash), 82%; or 38 g (from a procedure using a 30 minute hold at 39° C. and omitting a diisopropyl ether wash), 76%.

Example 3 tert-Butyl (3-{7-[2-(4-cyano-2-filuorophenoxyethyl]-9-oxa-3,7-diazabicyclo-[3.3.1]non-3-yl}propyl)carbamate Alternative A A suspension of 3-fluoro-4-[2-(9-oxa-3,7-diazabicyclo [3.3.1]non-3-yl)ethoxy]-benzonitrile hydrochloric acid salt (5 g, 0.0137 mol; see Preparation D above), tert-butyl (3-bromopropyl)carbamate (4.24 g, 0.0178 mol; see Preparation I above) and potassium carbonate (7.57 g, 0.0548 mol) in dry acetonitrile (100 mL) was stirred at 60° C. overnight under a nitrogen atmosphere. The reaction mixture was filtered through Celite® and solvent concentrated under reduced pressure. The residue was purified by column chromatography over silica gel, using 5% methanol in dichloromethane as eluent, to give 5.8 g of the title compound as yellow oil.

Alternative B tert-Butyl[3-(9-oxa-3,7-diazabicyclo[3.3.1]non-3-yl)propyl]carbamate (0.28 g, 0.98 mmol; see Preparation A above), 4-(2-bromoethoxy)-3-fluorobenzonitrile (0.3 g, 1.12 mmol; see Preparation D(v) above) and $K_2CO_3$ (0.25 g, 1.8 mmol) were mixed in acetonitrile (10 mL) and stirred at 60° C. under a nitrogen atmosphere overnight. The reaction mixture was filtered and the solvent removed from the filtrate under reduced pressure. The residue was purified by column chromatography over silica gel, using 4% methanol in dichloromethane as eluent, to yield 0.35 g of the title compound as a pale yellow solid.

$^1$H NMR (300 MHz, CDCl$_3$) δ 7.31-7.22 (2H, dd), 7.00 (1H, m), 6.75 (1H, s), 4.26 (2H, t), 3.89 (2H, s), 3.2-2.2 (14H, m), 1.6 (2H, bs), 1.32 (9H, s).

Accurate mass: $[C_{23}H_{33}N_4O_4F+H]^+=449.25$ (within 5 ppm of the elemental compositions)

Example 4 tert-Butyl (3-{7-[3-(4-cyano-2-fluorophenoxypropyl]-9-oxa-3,7-diazabicyclo-[3.3.1]non-3-yl}propyl)carbamate A suspension of 3-fluoro-4-[3-(9-oxa-3,7-diazabicyclo [3.3.1]non-3-yl)propoxy]-benzonitrile (2.4 g, 7 mmol; see Preparation E above), tert-butyl (3-bromopropyl)-carbamate (1.84 g, 7.7 mmol; see Preparation I above) and dry $K_2CO_3$ (2.9 g, 21 mmol) in dry acetonitrile (24 mL) was stirred at 60° C. overnight under a nitrogen atmosphere. The reaction mixture was filtered through Celite® and the filtrate was concentrated under reduced pressure. The residue was purified by column chromatography over silica gel, using 7 to 8% methanol in DCM as eluent, to yield 1.45 g of the title compound as a colourless, gummy liquid.

Accurate mass:$[C_{24}H_{35}N_4O_4F+H]^+=463.27$ (within 5 ppm of the elemental compositions)

Example 5 tert-Butyl (3-{7-[3-(4-cyanophenoxypropyl]-9-oxa-3,7-diazabicyclo[3.3.1]non-3-yl}propyl)carbamate Alternative A The title compound was made in analogy with Example 8 below, using 4-[3-(9-oxa-3,7-diazabicyclo[3.3.1]non-3-yl) propoxy]benzonitrile in place of 4-[2-(9-oxa-3,7-diazabicyclo[3.3.1]non-3-yl)ethoxy]benzonitrile (see WO 01/28992).

Alternative B

4-[3-(9-Oxa-3,7-diazabicyclo[3.3.1]non-3-yl)propoxy] benzonitrile hydrochloric acid salt (5.4 g, 15.0 mmol; see WO 01/28992), tert-butyl (3-bromopropyl)-carbamate (3.57 g, 15 mmol; see Preparation I above) and $K_2CO_3$ (8.29 g, 60.0 mmol) were mixed in acetonitrile (200 mL) and water (5 mL). The reaction mixture was refluxed for 2.5 h. The solids were filtered off and the solvents were evaporated. The crude product was dissolved in dichloromethane, washed with water, dried with $MgSO_4$ and evaporated, giving 6.4 g of a red oil. The oil was divided in two fractions and was purified by chromatography on silica gel (Horizon™, flash system from Biotage™, column: Flash 40+M, 40×150 mm. using methanol saturated with ammonia in dichloromethane as eluent) to provide the title compound as an oil.

Yield: 3.65 g.

$^{13}$C NMR (125 MHz, CDCl$_3$): δ 162.25, 158.29, 133.93, 119.17, 114.99, 103.77, 78.8, 68.59, 66.99, 59.51, 56.61, 56.34, 55.80, 41.25, 28.82, 26.52, 25.8.

Alternative C

To tert-Butyl[3-(7-benzyl-9-oxa-3,7-diazabicyclo[3.3.1] non-3-yl)propyl]-carbamate (94.07 g, 250.51 mmol; see Example 11 below) was added a pre-mixed suspension comprising 5% palladium on carbon (9.43 g, 5% rel. wt., ca. 60% water wet paste), ethanol (500 mL), water (10 mL) and citric acid (14.46 g, 75.26 mmol). The resulting mixture was hydrogenated at 4 bar and room temperature for 18 hours. TLC (1:1 dichloromethane:Solvent X, potassium permanganate stain, X=80:18:2 chloroform:methanol: 35% aqueous ammonia) showed that the reaction was complete. The catalyst was removed by filtration and washed with ethanol (100 mL). The resulting filtrate and catalyst washing was added to 3-(4-cyanophenoxy)propyl bromide (60.18 g, 250.65 mmol; see, for example, WO 01/28992) and 1 M aqueous sodium carbonate (115 mL). This provided a mixture that was then heated at reflux for 4 hours. Further 3-(4-cyano-phenoxy) propyl bromide (12.04 g, 50.15 mmol) was added, and the mixture refluxed for a further 3 hours. TLC (1:1 dichloromethane:X) showed that the reaction was complete. The reaction mixture was concentrated in vacuo to give a yellow oil. The residue was partitioned between toluene (400 mL) and 10% w/w citric acid (600 mL) and the resulting biphasic mixture stirred at room temperature for 20 minutes. Further 10% w/w citric acid (500 mL) was added and the mixture stirred for 30 minutes. A third portion of 10% w/w citric acid (500 mL) was added. After being stirred together at room temperature for a further 10 minutes, the phases were separated. Toluene (750 mL) and 5 M sodium hydroxide were added to the retained aqueous phase. After being stirred together at room temperature for 15 minutes, the phases were again separated. Further 5 M sodium hydroxide (100 mL) was added, and stirring at room temperature was then undertaken for 10 minutes. The phases were separated once more and the organic phase retained, dried (MgSO$_4$), filtered and concentrated in vacuo to provide the sub-title compound as a pale yellow oil (95.50 g, 214.81 mmol), 86%). Residual toluene was removed from the product by twice re-dissolving in ethyl acetate (600 mL) and then concentrating in vacuo (this reduced the residual toluene level to 0.32 wt %).

$^1$H NMR (300 MHz, DMSO-d$_6$): δ 7.74 (dd, J=6.9, 1.9 Hz, 2H), 7.06 (dd, J=6.9, 2.1 Hz, 2H), 4.11 (t, J=6.4 Hz, 2H), 3.81 (s, 2H), 3.31 (s, 2H), 3.01 (d, J=5.8 Hz, 3H), 2.96 (d, J=11.5 Hz, 2H), 2.83 (d, J=11.1 Hz, 2H), 2.36 (t, J=6.9 Hz, 2H), 2.22 (m, 4H), 1.90 (t, J=6.6 Hz, 2H), 1.49 (t, J=5.9 Hz, 2H), 1.36 (s, 9H).

After being allowed to stand at ambient temperature for approximately 2 weeks (at which point the oily product had partially crystallised), the title compound was obtained in crystalline form by utilising the following procedure.

The oil/crystal mixture was dried under reduced pressure (at RT) for approximately 2 hours. At this point, crystals started to grow at the bottom of the product mixture, and a solid mass covered with oil was formed. The solid material was crushed with a spatula and the mixture of oil and solid was then dried under reduced pressure at RT overnight, after which the entire product mixture had crystallised. The crystalline material was ground to reduce particle size and was then further dried under reduced pressure (at RT) for approximately 2.5 days (a weekend). This provided 87.1 g of the title compound in crystalline form (a white powder having a melting point of 55° C.). Analysis (by $^{13}$C NMR and HPLC and comparison to a deliberately synthesised sample of 4-(3-hydroxypropoxy)-benzonitrile) indicated that this material contained ~1% of an impurity (4-(3-hydroxypropoxy)benzonitrile).

Example 6 tert-Butyl (2-{7-[2-(4-cyanophenoxy)ethyl]-9-oxa-3,7-diazabicyclo[3.3.1]non-3-yl}ethyl)methylcarbamate Oxalyl chloride (0.544 g, 0.4 mmol) was added at –78° C. to a solution of DMSO (0.7 g, 0.9 mmol) in dry dichloromethane (10 mL). The resulting mixture was stirred for 15 min before tert-butyl (2-hydroxyethyl)methylcarbamate (0.5 g, 0.3 mmol; prepared by reaction of 2-methylaminoethanol with di-tert-butyl dicarbonate under standard conditions, using DCM as solvent), dissolved in dry dichloromethane, was added dropwise at –78° C. Stirring was continued for 3 h at the same temperature, before triethylamine was added (at –78° C.) and the reaction mixture was warmed to –30° C. The reaction was quenched with citric acid solution and extracted with dichloromethane. The organic layer was washed with brine and dried over sodium sulfate. Solvent evaporation yielded (0.35 g) of crude aldehyde (tert-butyl (2-oxoethyl) methylcarbamate).

The crude aldehyde was then taken in DCM (10 mL). 4-[2-(9-Oxa-3,7-diazabicyclo[3.3.1]non-3-yl)ethoxy]benzonitrile (0.221 g, 0.8 mmol; see WO 01/28992), followed by acetic acid (0.182 g, 0.3 mmol), was added. After stirring for 1 h, NaBH$_3$CN (0.188 g, 0.3 mmol) was added. The reaction mixture was stirred at RT overnight, quenched with water and extracted with dichloromethane. The organic layer was washed with water and brine and dried over sodium sulfate. Solvent evaporation under reduced pressure, followed by purification by column chromatography over silica gel using 2.5% methanol in dichloromethane as eluent, yielded 80 mg of the title compound as a pale yellow, gummy liquid.

$^1$H NMR (300 MHz, CDCl$_3$): δ 7.58 (2H, dd), 7.00 (2H, dd), 4.33 (2H, t) 4.20 (2H, bs), 3.79 (2H, b), 3.58 (2H, m), 3.35 (2H, d), 3.23 (2H, d), 3.1 (6H, m), 2.92 (3H, s), 1.41 (9H, s).

Example 7 tert-Butyl (2-{7-[3-(4-cyanophenoxy)-2-fluoropropyl]-9-oxa-3,7-diazabicyclo[3.3.1]non-3-yl}ethyl) carbamate To a solution of DAST (0.73 g, 0.0043 mol) in dichloromethane (10 mL) was added tert-butyl (2-{7-[(2S)-3-(4-cyanophenoxy)-2-hydroxypropyl]-9-oxa-3,7-diazabicyclo[3.3.1]non-3-yl}ethyl)carbamate (1.50 g, 0.0033 mol; see Preparation R above), in (10 mL) of dichloromethane, dropwise under a nitrogen atmosphere at –65° C. The reaction mixture was slowly brought to RT and stirred at this temperature for 2 h (monitored by HPLC). The reaction mixture was quenched with NaHCO$_3$ (aq.) and extracted with dichloromethane. The organic layer was washed with water and brine and then dried over sodium sulfate. Solvent was evaporated under reduced pressure and the residue was purified by column chromatography over silica gel, using methanol-dichloromethane as the eluent, to yield 0.40 g of the title compound as a brownish, gummy solid.

Example 8

(3-{7-[2-(4-Cyanophenoxyethyl]-9-oxa-3,7-diazabicyclo[3.3.1]non-3-yl}-propyl)carbamic acid tert-butyl ester A suspension of 4-[2-(9-oxa-3,7-diazabicyclo[3.3.1]non-3-yl)ethoxy]benzonitrile (6.5 g, 0.02 mol; see WO 01/28992), tert-butyl (3-bromopropyl)carbamate (6.0 g, 0.025 mol; see Preparation I above) and dry K$_2$CO$_3$ (13.08 g, 0.0946 mol) in 40 mL of dry acetonitrile was stirred at 60° C. overnight under a nitrogen atmosphere. The reaction mixture was filtered through Celite® and the filtrate was concentrated under reduced pressure. The residue was purified by column chromatography over silica gel, using 20% ethyl acetate in petroleum ether as eluent, to yield 3.5 g of the sub-title compound as a liquid.

Example 9

{3-[7-(4-Cyanobenzyl)-9-oxa-3 7-diazabicyclo [3.3.1]non-3-yl]propyl}carbamic acid tert-butyl ester A suspension of 4-(9-oxa-3,7-diazabicyclo[3.3.1]non-3-yl-methyl)benzonitrile hydrochloride (6.8 g, 0.021 mol; see Preparation J above), tert-butyl (3-bromopropyl)carbamate (3.93 g, 0.017 mol; see Preparation I above) and dry K$_2$CO$_3$ (8.24 g, 0.059 mol) in 27 mL of dry acetonitrile was stirred at 60° C. overnight under a N$_2$ atmosphere. The reaction mixture was filtered through Celite® and the filtrate was concentrated under reduced pressure to give 7.5 g of the sub-title compound as pale a liquid.

Example 10 tert-Butyl {2-[7-(4-cyanobenzyl)-9-oxa-3,7-diazabicyclo[3.3.1]non-3-yl]ethyl}-carbamate Potassium carbonate (3.82 g, 27.6 mmol) was added to a mixture of tert-butyl[2-(9-oxa-3,7-diazabicyclo[3.3.1]non- 3-yl)ethyl]carbamate (5.00 g, 18.4 mmol; see WO 02/83690 and WO 2004/035592) and 4-(bromomethyl)benzonitrile (3.61 g, 18.4 mmol) in acetonitrile (150 mL). The mixture was heated to reflux overnight, cooled to room temperature, filtered and then evaporated. The residue was dissolved in dichloromethane (100 mL), washed with water and dried over $MgSO_4$. Purification by preparative HPLC gave 7.04 g (78%) of the title compound as a salt with one equivalent of acetic acid and one equivalent of formic acid.

$^1$H NMR (500 MHz, $CD_3OD$) δ 8.49 (1H, bs), 7.77 (2H, d), 7.58 (2H, d), 4.15 (2H, m), 3.75 (2H, s), 3.69 (2H, m), 3.46 (2H, t), 3.33 (2H, m), 3.16 (2H, t) 3.09 (2H, m), 2.76 (2H, m), 1.96 (3H, s), 1.44 (9H, s).

Example 11 tert-Butyl[3-(7-benzyl-9-oxa-3,7-diazabicyclo[3.3.1] non-3-yl)propyl]carbamate

Alternative A

To 3-benzyl-9-oxa-3,7-diazabicyclo[3.3.1]nonane dihydrochloride (25.08 g, 86.12 mmol; see Preparation O above) was added 2.5 M sodium hydroxide (115 mL). 3-(tert-Butyloxycarbonylamino)propyl 2,4,6-trimethylbenzenesulfonate (32.35 g, 90.50 mmol; see Preparation L above) and toluene (65 mL) were then added and the reaction mixture heated at 65° C. for 12 hours. The phases were separated at 65° C. and the lower (aqueous) layer discarded. The organic phase was re-heated to 65° C. and then extracted with 10% w/w aqueous citric acid (125 mL). The phases were separated and the upper (organic) phase discarded. To the aqueous citric acid phase was added isopropyl acetate (150 mL) and 5 M sodium hydroxide (75 mL). The resulting mixture was stirred at room temperature for 15 minutes. The phases were separated and the lower (aqueous) phase discarded. The resulting organic phase was dried ($MgSO_4$), filtered and the solvent removed in vacuo to give the title compound as a colourless oil (29.13 g, 77.60 mmol, 90%).

$^1$H NMR (300 MHz, $CDCl_3$): δ 7.31 (m, 5H), 3.85 (s, 2H), 3.51 (s, 2H), 3.32 (q, J=9.1 Hz, 2H), 2.95 (dd, J=38.9, 11.2 Hz, 4H), 2.45 (td, J=10.8, 3.6 Hz, 4H), 2.32 (t, J=5.9 Hz, 2H), 1.64 (s, 3H), 1.44 (s, 9H).

Alternative B

To 3-benzyl-9-oxa-3,7-diazabicyclo[3.3.1]nonane dihydrochloride (116.77 g, 400.97 mmol; see Preparation O above) was added 2.5 M sodium hydroxide (430 mL). A solution of 3-(tert-butyloxycarbonylamino)propyl bromide (95.25 g, 400.00 mmol) in toluene (240 mL) was added and the reaction mixture heated at 65° C. for 12 hours. The phases were separated and the lower (aqueous) layer discarded. The organic phase was extracted with 10% w/w aqueous citric acid (475 mL). The phases were separated and the upper (organic) phase discarded. To the aqueous citric acid phase was added isopropyl acetate (750 mL) and 5 M sodium hydroxide (200 mL). The resulting mixture was stirred at room temperature for 15 minutes. The phases were separated and the lower (aqueous) phase discarded. The resulting organic phase was dried ($MgSO_4$), filtered and the solvent removed in vacuo to give the title compound as a pale orange oil (123.31 g, 328.38 mmol, 82%).

$^1$H NMR (300 MHz, DMSO-$d_6$): δ 7.25 (m, 5H), 3.81 (s, 2H), 3.43 (s, 2H), 3.32 (s, 1H), 3.13 (q, J=5.8 Hz, 2H), 2.85 (t, J=11.0 Hz, 4H), 2.36 (dd, J=11.2, 3.2 Hz, 2H), 2.25 (m, 5H), 1.56 (quintet, J=5.9 Hz, 2H), 1.37 (s, 9H).

Alternative C

3-Benzyl-9-oxa-3,7-diazabicyclo[3.3.1]nonane dihydrochloride (1.5 g, 0.005 mol; see Preparation O above) was dissolved in dry acetonitrile (20 mL). $K_2CO_3$ (3.5 g, 0.025 mol) was then added and the suspension was stirred at RT for 10 min, before tert-butyl (3-bromopropyl)carbamate (1.4 g, 0.006 mol; see Preparation I above) was added and the reaction mixture stirred at 60° C. for 15 h under a nitrogen atmosphere. The reaction mixture was cooled to RT, filtered through a Celite® bed and the filtrate was concentrated under reduced pressure. The residue was purified by flash column chromatography over silica gel using 3% methanol in dichloromethane as eluent to yield (1.12 g, 58%) of the title compound as a brown solid.

Example 12

[3-(7-Benzyl-9-oxa-3,7-diazabicyclo[3.3.1]non-3-yl)-propyl]carbamic acid tert-butyl ester, 4-chlorobenzenesulfonic acid salt To 3-bromopropylamine hydrobromide (139.32 g, 636.40 mmol) was added a solution of di-tert-butyl dicarbonate (112.46 g, 510.13 mmol) in MIBK (800 mL) and 2.5 M sodium hydroxide (310 mL). The resulting mixture was stirred for 1 hour at room temperature. The reaction was monitored by TLC (9:1 isohexane:ethyl acetate, potassium permanganate stain). Water (345 mL) was added and the mixture stirred for 10 minutes. The phases were separated and the lower (aqueous) phase discarded. To the retained organic phase was added 3-benzyl-9-oxa-3,7-diazabicyclo[3.3.1] nonane dihydrochloride (148.43 g, 509.68 mmol; see Preparation O above) and 2.5 M sodium hydroxide (660 mL). This mixture was heated at 65° C. for 7 hours. At 65° C., the phases were separated and the lower (aqueous) phase discarded. The organic phase was re-heated to 65° C. and extracted with 10% w/w aqueous citric acid (562 mL). The phases were separated and the upper (organic) phase discarded. To the resulting aqueous phase was added MIBK (800 mL) and 5 M sodium hydroxide (230 mL) containing approximately 10% w/v sodium chloride (22.84 g). The resulting mixture was stirred at room temperature for 15 minutes. The phases were separated and the lower (aqueous) phase discarded. The organic phase was azeo-dried by removal of solvent (300 mL) by distillation under reduced pressure (keeping the temperature below 70° C.). The mixture was clarified by filtration whilst still hot and the residue washed with MIBK (115 mL). The temperature was adjusted to 60° C. and a solution of purified (see J. Am. Pharm. Assoc. 239-241 (1949)) 4-chlorobenzenesulfonic acid (99.24 g, 515.20 mmol) in MIBK (225 mL) was added over 90 minutes. The reaction mixture was then cooled to room temperature causing the product to crystallize from solution. The mixture was cooled to 5° C., the product was collected by filtration and the cake washed with MIBK (225 mL). The product was dried as far as possible on the filter, then oven dried in vacuo (50° C., 24 h) to give the title compound as a white solid (257.44 g, 453.13 mmol, 89%).

$^1$H NMR (300 MHz, DMSO-$d_6$): δ 7.61 (d, J=8.7 Hz, 2H), 7.46-7.35 (m, 7H), 7.10 (t, J=5.7 Hz, 1H), 4.15 (s, 2H), 3.70 (s, 2H), 3.40 (d, J=12.1 Hz, 3H), 3.07 (d, J=11.9 Hz, 4H), 2.97 (q, J=6.3 Hz, 2H), 2.84 (t, J=7.1 Hz, 2H), 2.76 (d, J=11.9 Hz, 2H), 1.70 (quintet, J=6.7 Hz, 2H), 1.45 (s, 9H).

Example 13 tert-Butyl (3-{7-[3-(4-cyanophenoxypropyl]-9-oxa-3 7-diazabicyclo[3.3.1]non-3-yl}propyl)carbamate, L-tartaric acid salt To [3-(7-Benzyl-9-oxa-3,7-diazabicyclo[3.3.1]non-3-yl) propyl]carbamic acid tert-butyl ester, 4-chlorobenzenesulfonic acid salt (50.20 g, 88.36 mmol; see Example 12 above) was added a mixture of propan-2-ol (150 mL) and water (50 mL), followed by 5% palladium on carbon (2.53 g, 5% rel. wt., ca. 60% water wet paste). The resulting mixture was hydrogenated at 2.5 bar and immediately heated to 50° C. Once the reaction had taken up the required amount of hydrogen, it was cooled to room temperature. TLC (1:1 dichloromethane:Solvent X, potassium permanganate stain, X=80:18:2 chloroform:methanol:35% aqueous ammonia) showed that the reaction was complete. The catalyst was removed by filtration and washed with propan-2-ol (75 mL). To the resulting filtrate and catalyst washing was added 1 M aqueous sodium carbonate (115 mL). The resulting mixture was heated to 55° C. and 3-(4-cyanophenoxy)propyl 4-toluenesulfonate (30.71 g, 92.67 mmol; see Preparation N above) was added. This provided a mixture that was then heated at reflux for 4 hours. TLC (1:1 dichloromethane:X) showed the reaction was complete. Solvent (236 mL) was removed by distillation under reduced pressure, keeping the temperature below 50° C. Toluene (220 mL) and 1 M sodium hydroxide (100 mL) were added and the resulting mixture was cooled to room temperature before further toluene (30 mL) and 1 M sodium hydroxide (50 mL) were added. The phases were separated and 10% w/w citric acid (250 mL) was added to the retained organic. After being stirred together at room temperature for 15 minutes, the phases were again separated. To the retained aqueous phase was added isopropyl acetate (550 mL) and 5 M sodium hydroxide (150 mL). Stirring at room temperature was then undertaken for 10 minutes. The phases were separated once more and the organic phase retained and washed with 20% w/w sodium chloride solution (50 mL). Solvent (100 mL) was removed from the organic phase by distillation under reduced pressure, keeping the temperature below 50° C. The remaining mixture was filtered whilst hot to remove insoluble material, which was then washed through with isopropyl acetate (50 mL). (At this stage, if desired, tert-butyl (3-{7-[3-(4-cyanophenoxy)-propyl]-9-oxa-3,7-diazabicyclo[3.3.1]non-3-yl}propyl)carbamate in neutral form can be isolated by concentration of the resulting filtrate.) The solution was re-heated to 50° C. before L-tartaric acid (13.42 g, 88.52 mmol), dissolved (by warming) in ethanol (150 mL), was added over the course of 30 minutes. The resulting mixture was cooled to room temperature, causing crystallisation of the product from solution. The solution was cooled to 5° C., the product collected by filtration and the filter cake washed with isopropyl acetate (150 mL). The product was dried as far as possible on the filter, then oven dried in vacuo (40° C., 24 h) to give the sub-title compound as a white solid (44.00 g, 73.99 mmol, 84%).

$^1$H NMR (400 MHz, CD$_3$OD): δ 7.65 (dd, J=6.9, 1.8 Hz, 2H), 7.06-7.02 (m, 2H), 4.38 (s, 2H), 4.19 (s, 2H), 4.14 (t, J=6.0 Hz, 2H), 3.51 (d, J=12.3 Hz, 2H), 3.27 (s, 1H), 3.11 (t, J=5.9 Hz, 4H), 3.02 (t, J=7.9 Hz, 2H), 2.90 (d, J=11.8 Hz, 2H), 2.64 (t, J=6.2 Hz, 2H), 2.24 (dd, J=10.1, 5.8 Hz, 2H), 1.74 (t, J=6.0 Hz, 2H), 1.45 (s, 9H).

$^1$H NMR (400 MHz, D$_2$O): δ 7.75 (d, J=9.0 Hz, 2H), 7.11 (d, J=8.7 Hz, 2H), 4.53 (s, 2H), 4.30 (s, 2H), 4.24 (t, J=5.6 Hz, 3H), 3.57 (d, J=12.6 Hz, 2H), 3.40 (d, J=12.3 Hz, 2H), 3.12 (d, J=12.3 Hz, 2H), 3.01 (t, J=7.2 Hz, 4H), 2.94 (t, J=6.2 Hz, 3H), 2.63 (t, J=7.2 Hz, 2H), 2.21 (quintet, J=6.5 Hz, 2H), 1.66 (q, J=6.7 Hz, 2H), 1.43 (d, J=10.8 Hz, 9H).

Example 14 tert-Butyl (3-{7-[3-(4-cyanophenoxy)propyl]-9-oxa-3,7-diazabicyclo[3.3.1]non-3-yl}propyl)carbamate, hydrobromic acid salt

[3-(7-Benzyl-9-oxa-3,7-diazabicyclo[3.3.1]non-3-yl)propyl]carbamic acid tert-butyl ester (123.31 g, 328.38 mmol; see Example 11 above) was dissolved in a pre-mixed solution of ethanol (620 mL), water (13 mL) and citric acid (19.14 g, 99.62 mmol). 5% Palladium on carbon (12.36 g, 10% rel. wt.) was then added. The reaction mixture was hydrogenated at room temperature and 4 bar pressure overnight. The reaction was checked for completion by TLC (1:1 dichloromethane: Solvent X, potassium permanganate stain, X=80:18:2 chloroform:methanol: 35% aqueous ammonia). The catalyst was removed by filtration and washed with ethanol (150 mL). The resulting filtrate and washings were then added to 3-(4-cyanophenoxy)-1-bromopropane (94.52 g, 393.67 mmol) and 1 M aqueous sodium carbonate (150 mL). This mixture was then heated at reflux for 5 hours. The reaction was checked for completion by TLC (1:1 dichloromethane:X). The reaction mixture was filtered at room temperature and concentrated in vacuo to give a pale yellow oil. To the residue was added toluene (500 mL) and 20% w/v aqueous citric acid (1000 mL). The resulting biphasic mixture was stirred at room temperature for 30 minutes, and then the phases were separated. To the retained aqueous phase was added ethyl acetate (700 mL) and 5 M aqueous sodium hydroxide (500 mL), and the mixture stirred at room temperature for 15 minutes. The phases were separated and the organic phase retained, dried (MgSO$_4$), filtered and concentrated in vacuo to give the title compound as a pale yellow oil (144.09 g, 274.16 mmol, 83%). This oil was triturated with diisopropyl ether (600 mL), at which point which the oil solidified. The mixture was heated to reflux, and propan-2-ol (70 mL) was added. The mixture was then cooled to room temperature, after which the product was collected by filtration and the cake washed with diisopropyl ether (100 mL). The product was suction dried as far as possible on the filter, then oven dried in vacuo (40° C., 16 h) to give the title compound as a white crystalline solid (95.54 g, 181.78 mmol, 56%).

Melting point=110-116° C.
Elemental analysis
Actual: Bromide 11.9% w/w, Sulfate 0.6% w/w.
Calculated for C$_{24}$H$_{37}$N$_4$O$_4$Br: Bromide 15.4% w/w, Sulfate 0.0% w/w.

$^1$H NMR (300 MHz, CD$_3$OD): δ 7.72-7.64 (m, 2H), 7.11-7.05 (m, 2H), 4.26-4.13 (m, 4H), 3.61-3.50 (m, 2H), 3.39-3.28 (m, 3H), 3.21-2.99 (m, 6H), 2.98-2.85 (m, 2H), 2.72-2.61 (m, 2H), 2.33-2.20 (m, 2H), 1.83-1.71 (m, 2H), 1.48 (s, 9H).

Example 15 tert-Butyl (2-{7-[2-(4-cyano-2-fluorophenoxyethyl]-9-oxa-3,7-diazabicyclo-[3.3.1]non-3-yl}ethyl)carbamate, fumarate salt Alternative A
tert-Butyl (2-{7-[2-(4-cyano-2-fluorophenoxy)ethyl]-9-oxa-3,7-diazabicyclo-[3.3.1]non-3-yl}ethyl)carbamate (580 mg, 1.33 mmol; see Example 2 above) and fumaric acid (155 mg, 1.33 mmol) were combined in acetone (20 mL). Crystals were obtained by slow evaporation of solvent from the resulting solution. The crystals were collected and dried under reduced pressure to give 717 mg (98%) of white crystals of the title compound containing residual solvent (4% w/w as determined by $^1$H NMR measurements).

$^1$H-NMR (500 MHz, CD$_3$OD): δ 7.56 (m, 1H), 7.54 (m, 1H), 7.31 (m, 1H), 6.67 (s, 2H), 4.45 (t, 2H), 4.18 (m, 2H), 3.66 (m, 2H), 3.40 (t, 2H), 3.36 (m, 2H), 3.27 (m, 2H), 3.11 (t, 2H), 3.04 (m, 4H), 1.39 (s, 9H).

Alternative B

To tert-butyl (2-{7-[2-(4-cyano-2-fluorophenoxy)ethyl]-9-oxa-3,7-diazabicyclo-[3.3.1]non-3-yl}ethyl)carbamate (15 g) was added isopropyl acetate (150 mL). To this was added fumaric acid (4.00 g) and propan-2-ol (30 mL). The resulting mixture was heated to 80° C., over one hour, and held at this temperature for one hour before cooling to 20° C. over four hours. The reaction mixture was then held at 20° C. for approximately ten hours before being further cooled to 5° C., over half an hour, and then held at 5° C. for fifteen minutes. The mixture was filtered and washed with cold isopropyl acetate (40 mL, 5° C.). The damp solid was dried in vacuo at 35° C., for approximately twenty-four hours to give the title compound as a white, crystalline solid (16.2 g, 85%).

$^1$H-NMR (300 MHz, CD$_3$OD): δ 7.67-7.52 (m, 2H), 7.33 (t, J=8.6 Hz, 1H), 6.70 (s, 2H), 4.48 (t, J=5.4 Hz, 2H), 4.29-4.11 (m, 2H), 3.77-3.61 (m, 2H), 3.51-3.22 (m, 4H), 3.21-2.98 (m, 4H), 1.42 (s, 9H), 1.17 (d, J=6.1 Hz, 4H).

Example 16 tert-Butyl (2-{7-[2-(4-cyano-2-fluorophenoxyethyl]-9-oxa-3 7-diazabicyclo-[3.3.1]non-3-yl}ethyl)carbamate, maleate salt tert-Butyl (2-{7-[2-(4-cyano-2-fluorophenoxy)ethyl]-9-oxa-3,7-diazabicyclo-[3.3.1]non-3-yl}ethyl)carbamate (400 mg, 0.92 mmol; see Example 2 above) and maleic acid (107 mg, 0.92 mmol) were combined in acetone (10 mL). Crystals were obtained by slow evaporation of solvent from the resulting solution. The crystals were collected and dried under reduced pressure to give 410 mg (81%) of the title compound as white crystals.

$^1$H-NMR (500 MHz, CD$_3$OD): δ 7.54 (m, 2H), 7.30 (m, 1H), 6.23 (s, 2H), 4.45 (t, 2H), 4.18 (m, 2H), 3.68 (m, 2H), 3.40 (t, 2H), 3.37 (m, 2H), 3.28 (m, 2H), 3.11 (t, 2H), 3.05 (m, 4H), 1.39 (s, 9H).

Example 17

The following compounds were prepared, from appropriate intermediates (such as those described hereinbefore), according to or by analogy with methods described herein:
(i) tert-butyl (3-{7-[3-(2,4-dicyanophenoxy)propyl]-9-oxa-3,7-diazabicyclo-[3.3.1]non-3-yl}propyl)carbamate;
(ii) tert-butyl ((2R)-3-{7-[(2S)-3-(4-cyanophenoxy)-2-hydroxypropyl]-9-oxa-3,7-diazabicyclo[3.3.1]non-3-yl}-2-fluoropropyl)carbamate;
(iii) tert-butyl (3-{7-[(2S)-3-(4-cyanophenoxy)-2-hydroxypropyl]-9-oxa-3,7-diaza-bicyclo[3.3.1]non-3-yl}propyl)methylcarbamate;
(iv) tert-butyl (3-{7-[3-(4-cyanophenoxy)propyl]-9-oxa-3,7-diazabicyclo[3.3.1]-non-3-yl}propyl)methylcarbamate;
(v) tert-butyl (3-{7-[2-(4-cyanophenoxy)ethyl]-9-oxa-3,7-diazabicyclo[3.3.1]non-3-yl}propyl)methylcarbamate;
(vi) tert-butyl (2-{7-[2-(4-cyanophenoxy)ethyl]-9-oxa-3,7-diazabicyclo[3.3.1]non-3-yl}ethyl)methylcarbamate;
(vii) tert-butyl (2-{7-[3-(4-cyanophenoxy)propyl]-9-oxa-3,7-diazabicyclo[3.3.1]-non-3-yl}ethyl)methylcarbamate;
(viii) tert-butyl (3-{7-[3-(4-cyano-2,6-difluorophenoxy)propyl]-9-oxa-3,7-diaza-bicyclo[3.3.1]non-3-yl}propyl)carbamate;
(ix) tert-butyl (2-{7-[2-(4-cyano-2,6-difluorophenoxy)ethyl]-9-oxa-3,7-diaza-bicyclo[3.3.1]non-3-yl}ethyl)carbamate;
(x) tert-butyl (2-{7-[3-(4-cyano-2,6-difluorophenoxy)propyl]-9-oxa-3,7-diaza-bicyclo[3.3.1]non-3-yl}ethyl)carbamate;
(xi) tert-butyl (2-{7-[3-(4-cyano-2-fluorophenoxy)propyl]-9-oxa-3,7-diaza-bicyclo[3.3.1]non-3-yl}ethyl)carbamate;
(xii) tert-butyl (2-{7-[(2S)-3-(4-cyano-2,6-difluorophenoxy)-2-hydroxypropyl]-9-oxa-3,7-diazabicyclo[3.3.1]non-3-yl}ethyl)carbamate;
(xiii) tert-butyl (2-{7-[(2S)-3-(4-cyano-2-fluorophenoxy)-2-hydroxypropyl]-9-oxa-3,7-diazabicyclo[3.3.1]non-3-yl}ethyl)carbamate;
(xiv) tert-butyl (3-{7-[2-(4-cyanophenoxy)ethyl]-9-oxa-3,7-diazabicyclo[3.3.1]-non-3-yl}propyl)carbamate;
(xv) tert-butyl[2-(7-{2-[(4-cyanobenzyl)oxy]ethyl}-9-oxa-3,7-diazabicyclo-[3.3.1]non-3-yl)ethyl]carbamate;
(xvi) tert-butyl (2-{7-[3-(4-cyanophenoxy)-2-fluoropropyl]-9-oxa-3,7-diaza-bicyclo[3.3.1]non-3-yl}ethyl)carbamate;
(xvii) tert-butyl (2-{7-[2-(4-cyanophenyl)ethyl]-9-oxa-3,7-diazabicyclo[3.3.1]-non-3-yl}ethyl)carbamate;
(xviii) tert-butyl (2-{7-[(2S)-3-(4-cyanophenoxy)-2-methoxypropyl]-9-oxa-3,7-diazabicyclo[3.3.1]non-3-yl}ethyl)carbamate;
(xix) tert-butyl (2-{7-[(2S)-3-(4-cyanophenoxy)-2-hydroxypropyl]-9-oxa-3,7-diazabicyclo[3.3.1]non-3-yl}ethyl)methylcarbamate;
(xx) tert-butyl[2-(7-{3-[(4-cyanophenyl)sulfonyl]propyl}-9-oxa-3,7-diaza-bicyclo[3.3.1]non-3-yl)ethyl]carbamate;
(xxi) tert-butyl[2-(7-{2-[2-(4-cyanophenyl)ethoxy]ethyl}-9-oxa-3,7-diaza-bicyclo[3.3.1]non-3-yl)ethyl]carbamate;
(xxii) tert-butyl (3-{7-[(25S)-3-(4-cyanophenoxy)-2-hydroxypropyl]-9-oxa-3,7-diazabicyclo[3.3.1]non-3-yl}propyl)carbamate;
(xxiii) tert-butyl (2-{7-[3-(4-fluorophenoxy)-2-hydroxypropyl]-9-oxa-3,7-diaza-bicyclo[3.3.1]non-3-yl}ethyl)carbamate;
(xxiv) tert-butyl (2-{7-[3-(4-chlorophenoxy)-2-hydroxypropyl]-9-oxa-3,7-diaza-bicyclo[3.3.1]non-3-yl}ethyl)carbamate;
(xxv) tert-butyl[2-(7-{2-[2-(4-cyanophenoxy)ethoxy]ethyl}-9-oxa-3,7-diaza-bicyclo[3.3.1]non-3-yl)ethyl]carbamate;
(xxvi) tert-butyl (2-{7-[2-(4-bromo-2-fluorophenoxy)ethyl]-9-oxa-3,7-diaza-bicyclo[3.3.1]non-3-yl}ethyl)carbaamate; and
(xxvii) tert-butyl (2-{7-[3-(2,4-dicyanophenoxy)propyl]-9-oxa-3,7-diaza-bicyclo[3.3.1]non-3-yl}ethyl)carbamate.

Example 18 tert-Butyl (3-{7-[3-(4-cyano-2-hydroxyohenoxypropyl]-9-oxa-3,7-diazabicyclo-[3.3.1]non-3-yl}propyl)carbamate To a stirred mixture of tert-butyl {3-[7-(3-hydroxypropyl)-9-oxa-3,7-diazabicyclo[3.3.1]non-3-yl]propyl}carbamate (0.030 g; 0.087 mmol; see Preparation T above), 3,4-dihydroxybenzonitrile (0.012 g; 0.087 mmol) and triphenylphosphine (0.025 g; 0.096 mmol) in DCM (2 mL) was added diisopropyl azodicarboxylate (0.019 g; 0.096 mmol) dissolved in DCM (1 mL). The resulting mixture was stirred overnight at room temperature and then for another 24 hours at 40° C. The mixture was then concentrated in vacuo. The crude product was purified by chromatography on silica gel (SP4™, flash system from Biotage™. Column: Flash 12+M, 9 g. A: DCM, B: DCM/MeOH(NH$_3$-satd.) 80:20. Eluent system: 1.15% B over 48 mL. 2. Linear gradient from 15 to 30% B over 156 mL. 3.30% B over 48 mL. 4. Linear gradient from 30 to 40% B over 156 mL. Fraction volume: 12 mL. Product in fractions 25-32), which afforded 10 mg (24.9%) of the title compound.

$^1$H NMR (500 MHz, CDCl$_3$): δ 7.18 (2H, m), 6.85 (1H, m), 6.70 (1H, s, broad), 4.13 (2H, m), 3.90 (2H, m), 3.20 (2H, m), 3.10 (2H, m), 2.92 (2H, m), 2.59-2.48 (6H, m), 2.34 (2H, m), 2.06 (2H, m), 1.60 (2H, m), 1.46 (9H, s)

Example 19

Title compounds of the above Examples were tested in Test A above and were found to exhibit D$_{10}$ values greater than 5.5. Indeed, the compounds of Examples 2 and 5 were found to have D$_{10}$ values of 6.3 and 6.8, respectively.

Example 20

Title compounds of the above Examples were tested in Test B above and were found to exhibit pIC$_{50}$ values of greater than 4.5. Indeed, the compounds of Examples 2 and 5 were found to have pIC$_{50}$ values of 5.0 and 6.19, respectively.

ABBREVIATIONS

Ac=acetyl
API=atmospheric pressure ionisation (in relation to MS)
aq.=aqueous
br=broad (in relation to NMR)
Bt=benzotriazole
t-BuOH=tert-butanol
CI=chemical ionisation (in relation to MS)
mCPBA=meta-chloroperoxybenzoic acid
d=doublet (in relation to NMR)
DAST=diethylaminosulfur trifluoride
DBU=diazabicyclo[5.4.0]undec-7-ene
DCM=dichloromethane
dd=doublet of doublets (in relation to NMR)
DMAP=4-dimethylaminopyridine
DMF=N,N-dimethylformamide
DMSO=dimethylsulfoxide
EDC=1-[3-(dimethylamino)propyl]-3-ethylcarbodiimide
Et=ethyl
EtOAc=ethyl acetate
eq.=equivalents
ES=electrospray (in relation to MS)
FAB=fast atom bombardment (in relation to MS)
FBS=foetal bovine serum
h=hour(s)
HCl=hydrochloric acid
HEPES=4-(2-hydroxyethyl)-1-piperazineethanesulfonic acid.
HPLC=high performance liquid chromatography
IMS=industrial methylated spirits
IPA=iso-propyl alcohol (propan-2-ol)
m=multiplet (in relation to NMR)
Me=methyl
MeCN=acetonitrile
MeOH=methanol
MIBK=methyl isobutyl ketone
min.=minute(s)
m.p. melting point
MS=mass spectroscopy
NADPH=nicotinamide adenine dinucleotide phosphate, reduced form
OAc=acetate
Pd/C=palladium on carbon
q=quartet (in relation to NMR)
RT=room temperature
s=singlet (in relation to NMR)
t=triplet (in relation to NMR)
TEA=triethylamine
THF=tetrahydrofuran
tlc=thin layer chromatography
TMSI=trimethylsilyl iodide Prefixes n-, s-, i-, t- and tert- have their usual meanings: normal, secondary, iso, and tertiary.

The invention claimed is:

1. A compound selected from:
   (a) tert-butyl (3-{7-[2-(4-cyano-2,6-difluorophenoxy)ethyl]-9-oxa-3,7-diazabicyclo[3.3.1]non-3-yl}propyl)carbamate;
   (b) tert-butyl (2-{7-[2-(4-cyano-2-fluorophenoxy)ethyl]-9-oxa-3,7-diazabicyclo[3.3.1]non-3-yl}ethyl)carbamate;
   (c) tert-butyl (3-{7-[2-(4-cyano-2-fluorophenoxy)ethyl]-9-oxa-3,7-diazabicyclo[3.3.1]non-3-yl}propyl)carbamate;
   (d) tert-butyl (3-{7-[3-(4-cyano-2-fluorophenoxy)propyl]-9-oxa-3,7-diazabicyclo[3.3.1]non-3-yl}propyl)carbamate;
   (e) tert-butyl (3-{7-[3-(4-cyanophenoxy)propyl]-9-oxa-3,7-diazabicyclo[3.3.1]non-3-yl}propyl)carbamate;
   (f) tert-butyl (2-{7-[2-(4-cyanophenoxy)ethyl]-9-oxa-3,7-diazabicyclo[3.3.1]non-3-yl}ethyl)methylcarbamate;
   (g) tert-butyl (2-{7-[3-(4-cyanophenoxy)-2-fluoropropyl]-9-oxa-3,7-diazabicyclo[3.3.1]non-3-yl}ethyl)carbamate;
   (h) (3-{7-[2-(4-cyanophenoxy)ethyl]-9-oxa-3,7-diazabicyclo[3.3.1]non-3-yl}-propyl)carbamic acid tert-butyl ester;
   (i) {3-[7-(4-cyanobenzyl)-9-oxa-3,7-diazabicyclo[3.3.1]non-3-yl]propyl}-carbamic acid tert-butyl ester;
   (j) tert-butyl {2-[7-(4-cyanobenzyl)-9-oxa-3,7-diazabicyclo[3.3.1]non-3-yl]ethyl}-carbamate;
   (k) tert-butyl[3-(7-benzyl-9-oxa-3,7-diazabicyclo[3.3.1]non-3-yl)propyl]-carbamate;
   (l) tert-butyl (3-{7-[3-(2,4-dicyanophenoxy)propyl]-9-oxa-3,7-diazabicyclo[3.3.1]non-3-yl}propyl)carbamate;
   (m) tert-butyl ((2R)-3-{7-[(2S)-3-(4-cyanophenoxy)-2-hydroxypropyl]-9-oxa-3,7-diazabicyclo[3.3.1]non-3-yl}-2-fluoropropyl)carbamate;
   (n) tert-butyl (3-{7-[(2S)-3-(4-cyanophenoxy)-2-hydroxypropyl]-9-oxa-3,7-diazabicyclo[3.3.1]non-3-yl}propyl)methylcarbamate;
   (o) tert-butyl (3-{7-[3-(4-cyanophenoxy)propyl]-9-oxa-3,7-diazabicyclo[3.3.1]non-3-yl}propyl)methylcarbamate;
   (p) tert-butyl (3-{7-[2-(4-cyanophenoxy)ethyl]-9-oxa-3,7-diazabicyclo[3.3.1]non-3-yl}propyl)methylcarbamate;
   (q) tert-butyl (2-{7-[2-(4-cyanophenoxy)ethyl]-9-oxa-3,7-diazabicyclo[3.3.1]non-3-yl}ethyl)methylcarbamate;
   (r) tert-butyl (2-{7-[3-(4-cyanophenoxy)propyl]-9-oxa-3,7-diazabicyclo[3.3.1]non-3-yl}ethyl)methylcarbamate;
   (s) tert-butyl (3-{7-[3-(4-cyano-2,6-difluorophenoxy)propyl]-9-oxa-3,7-diazabicyclo[3.3.1]non-3-yl}propyl)carbamate;
   (t) tert-butyl (2-{7-[2-(4-cyano-2,6-difluorophenoxy)ethyl]-9-oxa-3,7-diazabicyclo[3.3.1]non-3-yl}ethyl)carbamate;
   (u) tert-butyl (2-{7-[3-(4-cyano-2,6-difluorophenoxy)propyl]-9-oxa-3,7-diazabicyclo[3.3.1]non-3-yl}ethyl)carbamate;

(v) tert-butyl (2-{7-[3-(4-cyano-2-fluorophenoxy)propyl]-9-oxa-3,7-diazabicyclo[3.3.1]non-3-yl}ethyl)carbamate;

(w) tert-butyl (2-{7-[(2S)-3-(4-cyano-2,6-difluorophenoxy)-2-hydroxypropyl]-9-oxa-3,7-diazabicyclo[3.3.1]non-3-yl}ethyl)carbamate;

(x) tert-butyl (2-{7-[(2S)-3-(4-cyano-2-fluorophenoxy)-2-hydroxypropyl]-9-oxa-3,7-diazabicyclo[3.3.1]non-3-yl}ethyl)carbamate;

(y) tert-butyl (3-{7-[2-(4-cyanophenoxy)ethyl]-9-oxa-3,7-diazabicyclo[3.3.1]non-3-yl}propyl)carbamate;

(z) tert-butyl[2-(7-{2-[(4-cyanobenzyl)oxy]ethyl}-9-oxa-3,7-diazabicyclo[3.3.1]non-3-yl)ethyl]carbamate;

(aa) tert-butyl (2-{7-[3-(4-cyanophenoxy)-2-fluoropropyl]-9-oxa-3,7-diazabicyclo[3.3.1]non-3-yl}ethyl)carbamate;

(ab) tert-butyl (2-{7-[2-(4-cyanophenyl)ethyl]-9-oxa-3,7-diazabicyclo[3.3.1]non-3-yl}ethyl)carbamate;

(ac) tert-butyl (2-{7-[(2S)-3-(4-cyanophenoxy)-2-methoxypropyl]-9-oxa-3,7-diazabicyclo[3.3.1]non-3-yl}ethyl)carbamate;

(ad) tert-butyl (2-{7-[(2S)-3-(4-cyanophenoxy)-2-hydroxypropyl]-9-oxa-3,7-diazabicyclo[3.3.1]non-3-yl}ethyl)methylcarbamate;

(ae) tert-butyl[2-(7-{3-[(4-cyanophenyl)sulfonyl]propyl}-9-oxa-3,7-diazabicyclo[3.3.1]non-3-yl)ethyl]carbamate;

(af) tert-butyl[2-(7-{2-[2-(4-cyanophenyl)ethoxy]ethyl}-9-oxa-3,7-diazabicyclo[3.3.1]non-3-yl)ethyl]carbamate;

(ag) tert-butyl (3-{7-[(2S)-3-(4-cyanophenoxy)-2-hydroxypropyl]-9-oxa-3,7-diazabicyclo[3.3.1]non-3-yl}propyl)carbamate;

(ah) tert-butyl (2-{7-[3-(4-fluorophenoxy)-2-hydroxypropyl]-9-oxa-3,7-diazabicyclo[3.3.1]non-3-yl}ethyl)carbamate;

(ai) tert-butyl (2-{7-[3-(4-chlorophenoxy)-2-hydroxypropyl]-9-oxa-3,7-diazabicyclo[3.3.1]non-3-yl}ethyl)carbamate;

(aj) tert-butyl[2-(7-{2-[2-(4-cyanophenoxy)ethoxy]ethyl}-9-oxa-3,7-diazabicyclo[3.3.1]non-3-yl)ethyl]carbamate;

(ak) tert-butyl (2-{7-[2-(4-bromo-2-fluorophenoxy)ethyl]-9-oxa-3,7-diazabicyclo[3.3.1]non-3-yl}ethyl)carbamate;

(al) tert-butyl (2-{7-[3-(2,4-dicyanophenoxy)propyl]-9-oxa-3,7-diazabicyclo[3.3.1]non-3-yl}ethyl)carbamate; and (am) tert-butyl (3-{7-[3-(4-cyano-2-hydroxyphenoxy)propyl]-9-oxa-3,7-diazabicyclo[3.3.1]non-3-yl}propyl)carbamate, and salts thereof.

2. tert-Butyl (2-{7-[2-(4-cyano-2-fluorophenoxy)ethyl]-9-oxa-3,7-diazabicyclo[3.3.1]non-3-yl}ethyl)carbamate or a salt and/or solvate thereof.

3. tert-Butyl (2-{7-[2-(4-cyano-2-fluorophenoxy)ethyl]-9-oxa-3,7-diazabicyclo[3.3.1]non-3-yl}ethyl)carbamate, fumaric acid salt.

4. tert-Butyl (2-{7-[2-(4-cyano-2-fluorophenoxy)ethyl]-9-oxa-3,7-diazabicyclo[3.3.1]non-3-yl}ethyl)carbamate, maleic acid salt.

5. Crystalline tert-butyl (2-{7-[2-(4-cyano-2-fluorophenoxy)ethyl]-9-oxa-3,7-diazabicyclo[3.3.1]non-3-yl}ethyl)carbamate characterised by the presence, in X-ray powder diffraction measurements, of peaks at 2-Theta values of about 4.280, 8.513, 11.259, 14.120, 17.570 and 22.583 degrees.

6. Crystalline tert-butyl (2-{7-[2-(4-cyano-2-fluorophenoxy)ethyl]-9-oxa-3,7-diazabicyclo[3.3.1]non-3-yl}ethyl)carbamate as claimed in claim 5, which
(I) when characterised by thermogravimetric analysis, displays a weight loss of less than 0.1% up to 110° C., and/or
(II) when characterised by differential scanning calorimetry, at a heating rate of 10° C. per minute in a closed cup with a pinhole under flowing nitrogen, displays a melting temperature (Tm) having an onset at about 90° C. and/or an associated endotherm of melting of about 79 J/g.

7. Crystalline tert-butyl (2-{7-[2-(4-cyano-2-fluorophenoxy)ethyl]-9-oxa-3,7-diazabicyclo[3.3.1]non-3-yl}ethyl)carbamate characterised by the presence, in X-ray powder diffraction measurements, of peaks at 2-Theta values of about 8.012, 9.459 and 16.820 degrees.

8. Crystalline tert-butyl (2-{7-[2-(4-cyano-2-fluorophenoxy)ethyl]-9-oxa-3,7-diazabicyclo[3.3.1]non-3-yl}ethyl)carbamate as claimed in claim 7, which:
(I) when characterised by thermogravimetric analysis, displays a weight loss of less than 0.2% up to 110° C., and/or
(II) when characterised by differential scanning calorimetry, at a heating rate of 10° C. per minute in a closed cup with a pinhole under flowing nitrogen, displays a melting temperature (Tm) having an onset at about 90° C. and/or an associated endotherm of melting of about 89 J/g.

9. Crystalline tert-hutyl (2-{7-[2-(4-cyano-2-fluorophenoxy)ethyl]-9-oxa-3,7-diazabicyclo[3.3.1]non-3-yl}ethyl)carbamate, fumaric acid salt, which:
(I) when characterised by thermogravimetric analysis, displays a weight loss of about 1.4% up to 110° C., and/or
(II) when characterised by differential scanning calorimetry, at a heating rate of 10° C. per minute in a closed cup with a pinhole under flowing nitrogen, displays a melting temperature (Tm) having an onset at about 120° C.

10. Crystalline tert-butyl (2-{7-[2-(4-cyano-2-fluorophenoxy)ethyl]-9-oxa-3,7-diazabicyclo[3.3.1]non-3-yl}ethyl)carbamate, maleic acid salt, which:
(I) when characterised by thermogravimetric analysis, displays a weight loss of about 1.2% up to 110° C., and/or
(II) when characterised by differential scanning calorimetry, at a heating rate of 10° C. per minute in a closed cup with a pinhole under flowing nitrogen, displays a melting temperature (Tm) having an onset at about 90° C.

11. Crystalline tert-butyl (3-{7-[3-(4-cyanophenoxy)propyl]-9-oxa-3,7-diazabicyclo[3.3.1]non-3-yl}propyl)carbamate characterised by the presence, in X-ray powder diffraction measurements, of peaks at 2-Theta values of about:
(a) 10.640; or
(b) 10.940, 11.064, 11.643, 12.166, 13.226, 15.644, 15.944, 16.928, 18.586, 19.124, 20.358 and 21.824.

12. Crystalline tert-butyl (3-{7-[3-(4-cyanophenoxy)propyl]-9-oxa-3,7-diazabicyclo[3.3.1]non-3-yl}propyl)carbamate as claimed in claim 11, which:
(i) when characterised by thermogravimetric analysis, displays a weight loss of less than 0.2% up to 110° C., and/or
(ii) when characterised by differential scanning calorimetry, at a heating rate of 10° C. per minute in a closed cup with a pinhole under flowing nitrogen, displays a melting temperature (Tm) having an onset at
(I) for the crystalline material of claim 11(a), about 48° C. or (II) for the crystalline material of claim 11(b), about 66° C.

13. Crystalline tert-butyl (3-{7-[3-(4-cyanophenoxy)propyl]-9-oxa-3,7-diazabicyclo[3.3.1]non-3-yl}propyl)carbamate, tartaric acid salt characterised by the presence, in X-ray powder diffraction measurements, of peaks at 2-Theta values of about:
(a) 5.346, 7.175, 8.222, 16.126, 16.458, 16.721, 18.670, 19.723, 19.996, 21.442, 21.599 and 22.505;
(b) 5.059;
(c) 5.111, 10.195, 16.280 and 19.958; or
(d) 5.315, 8.304, 16.553, 16.718, 18.627, 18.785, 19.976 and 21.849.

14. Crystalline tert-butyl (3-{7-[3-(4-cyanophenoxy)propyl]-9-oxa-3,7-diazabicyclo[3.3.1]non-3-yl}propyl)carbamate, tartaric acid salt as claimed in claim 13, which:
(i) for the crystalline material of claim 13 (a)
(I) when characterised by thermogravimetric analysis, displays a weight loss of about 1.0% up to 110° C., and/or
(II) when characterised by differential scanning calorimetry, at a heating rate of 10° C. per minute in a closed cup with a pinhole under flowing nitrogen, displays a melting temperature (Tm) having an onset at about 134° C.;
(ii) for the crystalline material of claim 13 (b)
(I) when characterised by thermogravimetric analysis, displays a weight loss of about 1.8% up to 60° C., and/or
(II) when characterised by differential scanning calorimetry, at a heating rate of 10° C. per minute in a closed cup with a pinhole under flowing nitrogen, displays a melting temperature (Tm) having an onset at about 90° C.;
(iii) for the crystalline material of claim 13 (c), when characterised by differential scanning calorimetry, at a heating rate of 10° C. per minute in a closed cup with a pinhole under flowing nitrogen, displays a melting temperature (Tm) having an onset at about 86° C.

15. Crystalline tert-butyl (3-{7-[3-(4-cyanophenoxy)propyl]-9-oxa-3,7-diazabicyclo[3.3.1]non-3-yl}propyl)carbamate, hydrobromic acid salt, which:
(I) when characterised by thermogravimetric analysis, displays a weight loss of about 1.9% up to 110° C., and/or
(II) when characterised by differential scanning calorimetry, at a heating rate of 10° C. per minute in a closed cup with a pinhole under flowing nitrogen, displays a melting temperature (Tm) having an onset at about 114° C.

16. A process for the preparation of a compound of formula I,

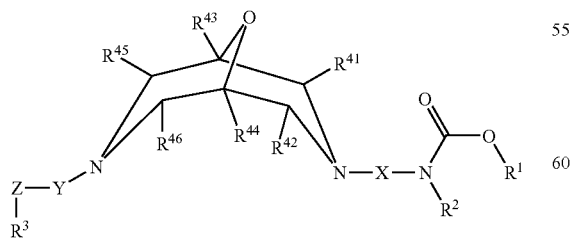

wherein
$R^1$ represents $C_{1-6}$ alkyl optionally substituted by one or more groups selected from halo and aryl;
$R^2$ represents H or $C_{1-4}$ alkyl (which latter group is optionally substituted by one or more halo atoms);
X represents $C_{2-4}$ n-alkylene optionally substituted by one or more groups selected from $C_{1-4}$ alkyl and halo;
Y represents $C_{1-6}$ n-alkylene, which alkylene group is
(a) optionally interrupted by —O—, —C(O)—, —S(O)$_{0-2}$—, —N($R^{5a}$)-$J^1$-, -$J^1$-N($R^{5b}$)— or —N(-$J^2$-$R^{5c}$),
(b) optionally substituted by one or more groups selected from halo and methyl and/or by a single $C_{1-6}$ alkyl group that is substituted by one or more groups selected from halo, —O-G-$R^{6a}$, -$J^1$-N($R^{6b}$)$R^{6c}$, —N($R^{6d}$)-$J^2$-$R^{6e}$ and —N($R^{6f}$)C(NH)NH$_2$, and/or
(c) optionally substituted, on a C-atom that is not attached to another heteroatom (N—, O— or S-atom), by a substituent selected from —O-G-$R^{6a}$, -$J^1$-N($R^{6b}$)$R^{6c}$—, —N($R^{6d}$)-$J^2$-$R^{6e}$, and —N($R^6$)C(NH)NH$_2$;
$J^1$ and $J^2$ independently represent, independently at each occurrence —C(O)—, —S(O)$_2$— or —OC(O)—, in which latter group the C(O) moiety is attached to the N-atom to which the group $J^1$ or $J^2$ is linked, or
$J^1$ may alternatively represent a direct bond, or
$J^2$ may alternatively represent —[C(O)]$_{1-2}$—N($R^{6g}$)—, in which latter group —N($R^{6g}$)— is attached to $R^{5c}$ or $R^{6e}$;
G represents a direct bond, —C(O)— or —C(O)O—, in which latter group the C(O) moiety is attached to the O-atom to which the group G is linked;
$R^{5a}$ and $R^{5b}$ independently represent H or $C_{1-6}$ alkyl;
$R^{5c}$ and $R^{6a}$ to $R^{6g}$ represent, independently at each occurrence, $C_{1-6}$ alkyl (optionally substituted by one or more groups selected from halo, aryl and Het$^1$), aryl or Het$^2$, or
$R^{6a}$ to $R^{6d}$, $R^{6f}$ and $R^{6g}$ represent, independently at each occurrence, H, or
$R^{5c}$ or $R^{6e}$, when $J^2$ represents —C(O)—, may alternatively represent H;
Het$^1$ and Het$^2$ independently represent five- to twelve-membered heterocyclic groups containing one or more heteroatoms selected from oxygen, nitrogen and/or sulfur, which groups are optionally substituted by one or more groups selected from —OH, oxo, halo, cyano, nitro, $C_{1-6}$ alkyl, $C_{1-6}$ alkoxy, aryl, aryloxy, —N($R^{7a}$)$R^{7b}$, —C(O)$R^{7c}$, —C(O)O$R^{7d}$, —C(O)N($R^{7e}$)$R^{7f}$, —N($R^{7g}$)C(O)$R^{7h}$, —S(O)$_2$N($R^{7i}$)$R^{7j}$ and —N($R^{7k}$)S(O)$_2$$R^{7m}$;
Z represents a direct bond, —O—, —C(O)—, —S(O)$_{0-2}$—, —S(O)$_2$—N($R^{7n}$)— or —N($R^{7p}$)—S(O)$_2$—;
$R^{7a}$ to $R^{7p}$ independently represent $C_{1-6}$ alkyl or aryl, or
$R^{7a}$ to $R^{7k}$, $R^{7n}$ and $R^{7p}$ independently represent H;
$R^3$ represents phenyl or Het$^a$, which latter two groups are optionally substituted by one or more $R^8$ groups;
Het$^a$ represents a five- to twelve-membered heterocyclic group containing one or more heteroatoms selected from oxygen, nitrogen and/or sulfur;
$R^8$ represents —OH, cyano, halo, nitro, $C_{1-6}$ alkyl (optionally terminated by —N(H)C(O)O$R^{9a}$, $C_{1-6}$ alkoxy, —N($R^{10a}$)$R^{10b}$, —C(O)$R^{10c}$, —C(O)O$R^{10d}$, —C(O)N($R^{10e}$)$R^{10f}$, —N($R^{10g}$)C(O)$R^{10h}$, —N($R^{10i}$)C(O)N($R^{10j}$)$R^{10k}$, —N($R^{10m}$)S(O)$_2$$R^{9b}$, —S(O)$_2$N($R^{10n}$)$R^{10p}$, —S(O)$_2$$R^{9c}$, —OS(O)$_2$$R^{9d}$, —Si($R^{9e}$)$_3$ or aryl;
$R^{9a}$ to $R^{9e}$ represent, independently at each occurrence, $C_{1-6}$ alkyl or phenyl, which latter group is optionally substituted by one or more groups selected from —OH, halo, cyano, $C_{1-4}$ alkyl and $C_{1-4}$ alkoxy;
$R^{10a}$ and $R^{10b}$ independently represent H, $C_{1-6}$ alkyl or together represent $C_{3-6}$ alkylene, resulting in a four- to seven-membered nitrogen-containing ring;

$R^{10c}$ to $R^{10p}$ independently represent H or $C_{1-6}$ alkyl; and $R^{41}$ to $R^{46}$ independently represent H or $C_{1-3}$ alkyl;

wherein each aryl group, unless otherwise specified, is optionally substituted; which process comprises:

(a) reaction of a compound of formula II,

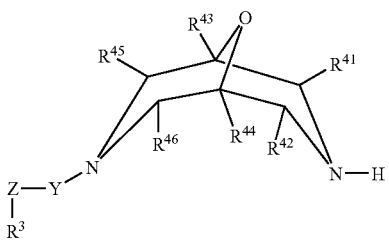

wherein $R^3$, $R^{41}$ to $R^{46}$, Y and Z are as defined above, with a compound of formula III,

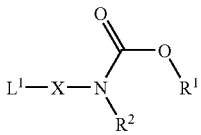

wherein $L_1$ represents a leaving group and X, $R^1$ and $R^2$ are as defined above;

(b) reaction of a compound of formula IV,

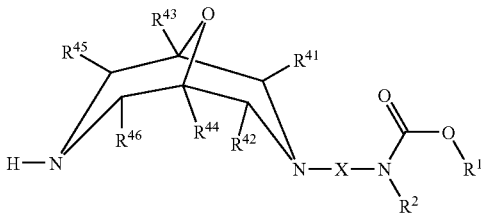

wherein $R^1$, $R^2$, $R^{41}$ to $R^{46}$ and X are as defined above, with a compound of formula V,

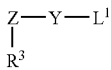

wherein $L^1$ is as defined above and $R^3$, Y and Z are as defined above;

(c) for compounds of formula I in which the group X comprises a $CH_2$ moiety at the point of attachment to the oxabispidine N-atom, reaction of a compound of formula II, as defined above, with a compound of formula VI,

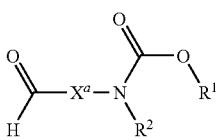

wherein $X^a$ represents $C_{1-3}$ n-alkylene optionally substituted by one or more groups selected from $C_{1-4}$ alkyl and halo, and $R^1$ and $R^2$ are as defined above, followed by reduction in the presence of a reducing agent;

(d) for compounds of formula I in which the group Y comprises a $-CH_2CH(OH)CH_2-$ moiety (wherein a $CH_2$ group forms the point of attachment to the oxabispidine N-atom), reaction of a compound of formula IV, as defined above, with a compound of formula VII,

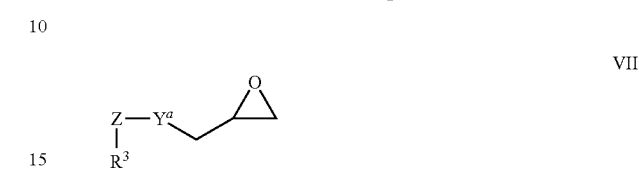

wherein $Y^a$ represents a direct bond or $C_{1-3}$ n-alkylene, which alkylene group is (1) optionally interrupted by $-O-$, $-C(O)-$, $-S(O)_{0-2}-$, $-N(R^{5a})-J^1-$, $J^1-N(R^{5b})-$, or $-N(-J_2-R_{5c})-$, (2) optionally substituted by one or more groups selected from halo and methyl and/or by a single $C_{1-6}$ alkyl group that is substituted by one or more groups selected from halo, $-O-G-R^{6a}$, $-J^1-N(R^{6b})R^{6c}$, $-N(R^d)-J^2-R^{6e}$ and $-N(R^{6f})C(NH)NH_2$, and/or (3) optionally substituted, on a C-atom that is not attached to another heteroatom (N—, O— or S-atom), by a substituent selected from $-O-G-R^{6a}$, $-J^1-N(R^{6b})R^{6c}-$, $-N(R^{6d})-J^2-R^{6e}$, and $-N(R^{6f})C(NH)NH_2$, and $R^3$, $R^{5a}$ to $R^{5c}$, $R^{6a}$ to $R^{6f}$, $J^1$, $J^2$, G and Z are as defined above;

(e) for compounds of formula I in which Z represents O, reaction of a compound of formula VIIa,

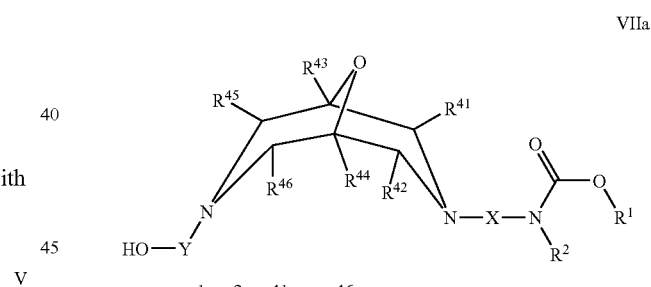

wherein $R^1$, $R^2$, $R^{41}$ to $R^{46}$, X and Y are as defined above, with a compound of formula IX,

$R^3$—OH        IX wherein $R^3$ is as defined above, under Mitsunobu conditions;

(f) for compounds of formula I in which X or Y represents an alkylene group that is substituted by halo, substitution of a corresponding compound of formula I in which X or Y represents an alkylene group that is substituted by OH, using an appropriate halogenating agent;

(g) conversion of one $R^8$ group to another, wherein $R^8$ is as defined above;

(h) introduction of one or more (further) $R^8$ groups;

(i) for acid addition salts of compounds of formula I, reaction of a corresponding compound of formula I with an acid; or (j) deprotection of a protected derivative of formula I.

* * * * *